(12) United States Patent
Gjerde

(10) Patent No.: US 11,097,207 B2
(45) Date of Patent: Aug. 24, 2021

(54) COLUMNS FOR ISOLATION, DETECTION AND USE OF BIOLOGICAL CELLS

(71) Applicant: Douglas T. Gjerde, Saratoga, CA (US)

(72) Inventor: Douglas T. Gjerde, Saratoga, CA (US)

(73) Assignee: Douglas T. Gjerde

(*) Notice: Subject to any disclaimer, the term of this patent is extended or adjusted under 35 U.S.C. 154(b) by 144 days.

(21) Appl. No.: 16/292,271

(22) Filed: Mar. 4, 2019

(65) Prior Publication Data

US 2019/0358562 A1    Nov. 28, 2019

Related U.S. Application Data

(63) Continuation of application No. 15/901,674, filed on Feb. 21, 2018, now Pat. No. 10,220,332, which is a continuation-in-part of application No. 15/098,275, filed on Apr. 13, 2016, now Pat. No. 10,107,729, which is a continuation-in-part of application No. 14/806,571, filed on Jul. 22, 2015, now Pat. No. 9,920,294, which is a continuation-in-part of application No. PCT/US2015/024374, filed on Apr. 3, 2015, and a continuation-in-part of application No. 14/563,994, filed on Dec. 8, 2014, now Pat. No.
(Continued)

(51) Int. Cl.
| | |
|---|---|
| *B01D 15/22* | (2006.01) |
| *C07K 1/22* | (2006.01) |
| *B01D 15/38* | (2006.01) |
| *G01N 1/34* | (2006.01) |
| *B01D 15/18* | (2006.01) |
| *G01N 1/40* | (2006.01) |
| *B01D 15/14* | (2006.01) |
| *G01N 35/04* | (2006.01) |

(52) U.S. Cl.
CPC ........... *B01D 15/22* (2013.01); *B01D 15/14* (2013.01); *B01D 15/1807* (2013.01); *B01D 15/3809* (2013.01); *C07K 1/22* (2013.01); *G01N 1/34* (2013.01); *G01N 1/405* (2013.01); *B01L 2200/0647* (2013.01); *G01N 2035/0434* (2013.01)

(58) Field of Classification Search
None
See application file for complete search history.

(56) References Cited

U.S. PATENT DOCUMENTS 8,377,715 B2 *  2/2013  Suh .................. C12N 15/101
                                                    436/177

OTHER PUBLICATIONS

Doran, Pauline M; Bailey, James E; "Effects of Immobilization on Growth, Fermentation Properties, and Macromolecular Composition of *Saccharomyces cerevisiae* Attached to Gelatin" Biotechnology and Bioengineering, 28, 73-87, 1986 (Year: 1986).*

* cited by examiner

*Primary Examiner* — David W Berke-Schlessel
(74) *Attorney, Agent, or Firm* — Sue S. Kalman

(57) ABSTRACT

This invention relates to devices and methods for purifying, detecting and using biological cells. A variety of cell types including viable tumor, stem, immune and sperm cells can be purified from a complex biological sample using a column, including a pipette tip column. Methods of the invention can aid research, diagnosis and treatment of cancer. Purified viable cells can be detected on the column or eluted from the column and detected. Cells on a column can be used as a stationary phase for liquid chromatography. Cells may be removed, recovered and analyzed.

18 Claims, 22 Drawing Sheets

Beads packed into flow-through column capture living cells on surface

Related U.S. Application Data

9,637,719, and a continuation-in-part of application No. PCT/US2014/016637, filed on Feb. 15, 2014.

(60) Provisional application No. 62/061,636, filed on Oct. 8, 2014, provisional application No. 61/974,950, filed on Apr. 3, 2014, provisional application No. 61/913,190, filed on Dec. 6, 2013, provisional application No. 61/832,501, filed on Jun. 7, 2013, provisional application No. 61/858,054, filed on Jul. 24, 2013, provisional application No. 61/873,828, filed on Sep. 4, 2013, provisional application No. 61/913,154, filed on Dec. 6, 2013, provisional application No. 61/765,541, filed on Feb. 15, 2013.

Antibody Interaction with Cell Surface Markers or Antigens

14A

14B

COLUMNS FOR ISOLATION, DETECTION AND USE OF BIOLOGICAL CELLS

FIELD OF THE INVENTION

This invention relates to columns and methods for purifying, detecting and using biological cells. A variety of cell types can be purified from a complex biological sample using a column. The method can be performed quickly and viable cells can be recovered. Purified viable cells can be detected on the column or eluted from the column and detected. Cells on a column can be used as a stationary phase for liquid chromatography. Cells may be interrogated, removed, recovered, analyzed and used.

BACKGROUND OF THE INVENTION

Since the first observations of cells as the "fundamental unit" of all living organisms, ranging from unicellular microbes such as *Escherichia coli* or *Saccharomyces cerevisiae* to multicellular, highly differentiated plants and animal, scientists have invested considerable effort in developing methods for isolating and investigating cells. Some populations of broadly similar cells can be obtained in large numbers by controlled fermentation in the case of microbes, or by tissue isolation in fluids such as spermatozoa or classes of blood cells in mammals, or laterally by cell culture technologies.

Magnetic beads are a popular format for capturing and purifying cells. In this technology, a suspension of beads is mixed with a suspension of cells. The magnetic beads can contain a tag or chemical entity selective for cells or for a particular cell type within the sample. After the cells become associated with the magnetic beads, a magnet is used to collect the magnetic beads with the associated cells. The magnetic beads may be resuspended several times with wash solutions to remove unbound cells. Finally, a solution can be used to release the cells from the beads and a magnet separates the magnetic beads from the cells.

However, magnetic beads have a number of drawbacks. First, they can negatively impact cell viability. Cell damage or death can occur when magnetic beads (with cells attached) are captured by a magnet. During this magnetic capture process, cells can be damaged or killed by crushing or squeezing as the beads are pressed together. This magnetic capture process must be performed several times endangering the cells. Second, magnetic bead methods have lengthy processing times and physically batter the cells which can result in cell clumping and death. Other common problems encountered with magnetic bead methods include low cell yield and impure cell populations.

There exists a need for a column technology that rapidly captures high concentrations of cells, particularly viable cells and then recovers the cells at high purity for research, detection and for other uses.

In the instant invention, it was discovered that cells can be captured on a column. In some embodiments, the captured cells remain viable and viable cells can be eluted from the column. Remarkably, cell capture can be performed by flowing the cells back and forth through a column. Previously, it was shown that small analytes such as proteins could be captured on a column using back and forth flow however, it was quite surprising that cells could withstand this treatment and remain viable.

The columns and methods described herein can be used to purify a desired cell type from a heterogeneous biological sample. Alternatively, contaminants can be captured and the desired cell type can flow through the column.

Captured cells can be manipulated on the column using a number of different strategies. In a second invention described herein, living cells captured on a column solid phase can be used as a stationary phase for liquid chromatography. After cell capture, the cells attached to the column can serve as a stationary phase and reagents, analytes or biomolecules can be passed through the column. In some embodiments, these reagents or biomolecules can be passed through the column using back and forth flow. The interaction of these entities with the stationary phase can be examined. If it is desired, the stationary phase comprised of cells, the cell-based stationary phase may be recovered and analyzed.

SUMMARY OF THE INVENTION

In the present invention, cells can be purified from a biological sample using a column. A sample comprised of cells is passed through the column that contains a solid phase and the cells within the sample can be captured on the solid phase. The cells in the sample can be of any type and from any source. For example, the sample can contain cells from a biological fluid such as blood or a tissue. In some embodiments of cells are intact and viable.

The sample can be passed through the column using unidirectional or bidirectional flow. In certain embodiments, the sample is passed through the column multiple times. The solid phase can be a chromatography medium such as a gel resin or an impermeable resin. Cells from a biological sample are captured on the column solid phase and following capture, the column can be washed to remove material that is not specifically bound to the column medium. In some embodiments, cells can be recovered by passing an eluent through the column. These recovered cells can be intact and viable.

The column is comprised of a column body and can contain one or two frits. The frits process the pore size large for cells to pass through but small enough to retain the solid phase. In those embodiments in which the column contains two frits, the column body, top frit and bottom frit define a media chamber. The solid phase lies within the media chamber and can be comprised of beads or particles. In certain embodiments, the solid phase is a loosely packed bed of medium that contains one or more unrestricted flow paths. In other embodiments, the solid phase is a fluidized bed. Equilibration, sample, wash, labeling and elution solutions can be passed through the unrestricted flow paths within the column bed.

The volume of the sample can be larger than the bed volume and in some embodiments, the sample volume is even larger than the column volume. The sample can be passed through the column in a flowing stream. The sample does not require incubation on the column.

Cells can be captured using a variety of strategies including affinity, ion exchange, hydrophobic interaction, reverse phase, normal phase, hydrophilic interaction and ion pairing. The solid phase can be further comprised of a capture entity capable of capturing cells present in the biological sample. Nonlimiting examples of capture entities include antibodies, antibody fragments, aptamers, lectins, proteins, peptides, polypeptides, nucleic acids, metals and combinations of these. In some embodiments, the capture entity is attached to the solid phase via a linker. In other embodiments, the capture entity is cross-linked to the column medium. In still other embodiments, the capture entity can be introduced into the column subsequent to column packing.

One advantage of manipulating cells with a column process is the use of active movement. Active movement can be described as the use of pumps to drive cells to travel in a flowing stream to and from the column solid phase, tubing, column connections, fittings and frits by a fluid pumping action. Active movement can be performed using either unidirectional flow or bidirectional flow. The term active movement is also used to describe the pumping of reagents to immobilized cells.

To keep cells viable, it is important to purify them quickly. In some embodiments, rapid flow rates are used and the cell purification can be performed in 3 hours or less. In certain embodiments, cells can be isolated, purified, detected or used in less than one hour, less than 45 minutes, less than 30 minutes or even less than 15 minutes.

In certain embodiments, captured cells can be tagged, labeled or otherwise interrogated on the column. After tagging or interrogation, cells can be eluted, lysed, counted or further manipulated on the column. When cells are lysed on column, their contents can be eluted and analyzed, e.g., by PCR. Alternatively, the solid phase with cells attached can be removed from the column.

In some embodiments, an enrichment can be performed. In these embodiments, the desired cells pass through the column while contaminants are captured.

In still other embodiments, cells captured on the column may serve as a stationary phase. A variety of entities can be introduced into the column in a mobile liquid phase and interact with the cell-based stationary phase. A variety of methods can be performed including partitioning, displacement, gradient and breakthrough chromatography. Flow can be unidirectional or bidirectional. Nonlimiting examples of these entities include biomolecules, analytes, reagents, cells, viruses, drugs, enzymes, nucleic acids, antibodies, antibody fragments, proteins carbohydrates, glycoproteins, vitamins and combinations of these. These entities can interact or be retained by the cell-based stationary phase and these interactions may be measured. Analyte reagents that interact with the stationary phase may be recovered and measured. In certain embodiments, the cells may be removed from the column and analyzed after their interaction with introduced entities.

The invention described herein also includes a variety of columns for use with cells. In some embodiments, the column is a pipette tip column or syringe. In other embodiments, the columns have a conventional format. In still other embodiments, the columns can be integrated into a multiwell plate. The columns can be sterile. Also described herein are a variety of methods for purifying cells using the columns of the invention. These methods can be automated and a plurality of columns can be operated in parallel.

In certain embodiments, the columns are part of a closed system or liquid-sealed system. In these embodiments, the columns themselves can be considered bidirectional. Either end of the column can serve as an inlet or an outlet (see FIGS. 14 through 18).

The methods of the invention are quite versatile; many cell types can be isolated and a wide variety of applications are possible. The applications include diagnostics, drug development, vaccine development, drug discovery, metabolic research and therapeutics.

BRIEF DESCRIPTION OF THE DRAWINGS

FIG. 1A depicts an aspiration step. FIG. 1B depicts an expulsion step. FIG. 1C depicts the elution of cells from the column shown in FIG. 1B.

In FIG. 2A, clear unrestricted flow paths are present during the aspiration. FIG. 2B depicts cell trapping during expulsion.

FIG. 3A depicts an aspiration step and FIG. 3B depicts an expulsion.

DETAILED DESCRIPTION OF THE INVENTION

Figures 1A, 1B, 1C:
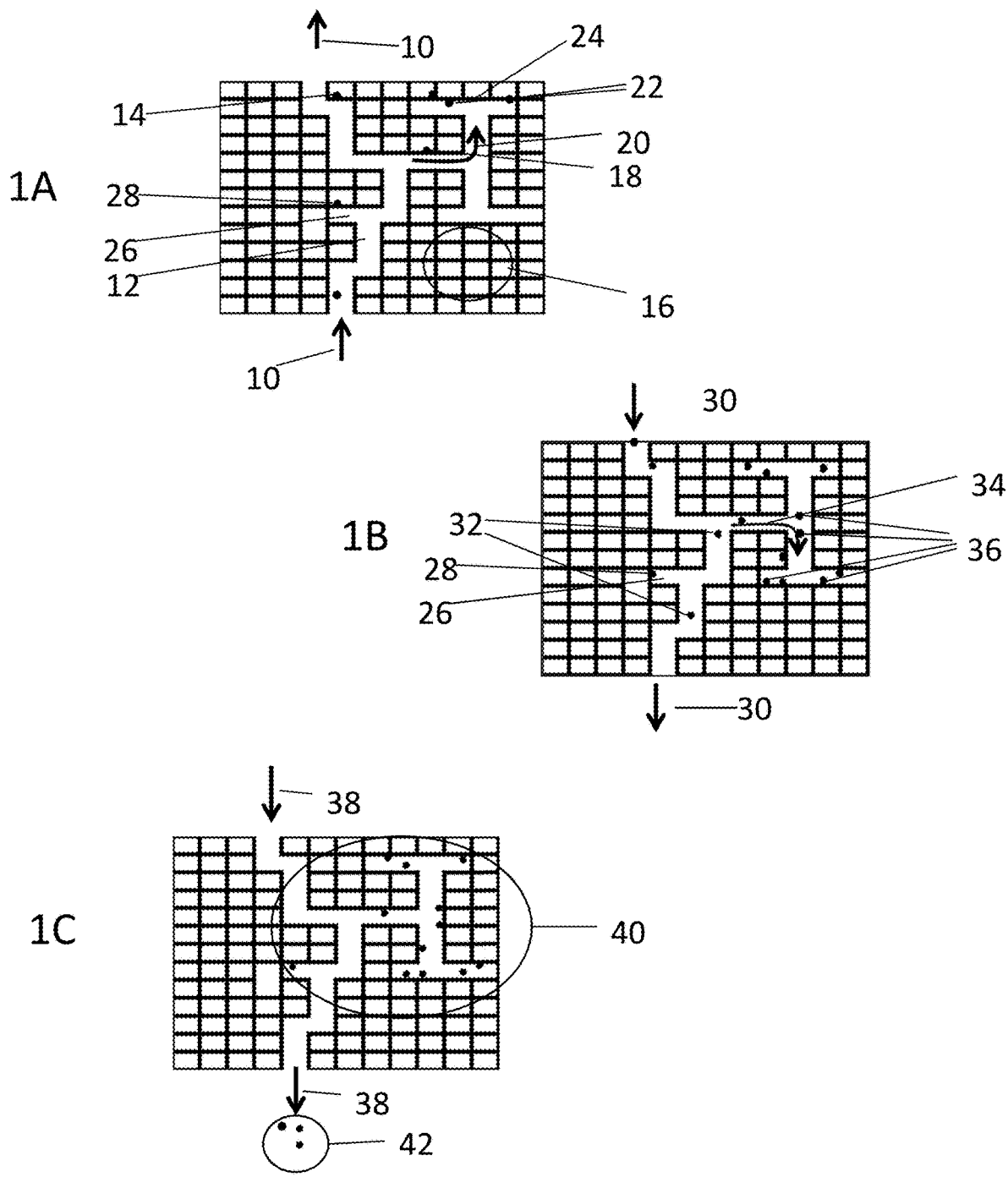
FIGS. 1A, 1B and 1C. Stylistic depictions of flow paths, nooks and traps in a column.

In the methods of the invention, whole cells are captured using a column that contains a bed of medium. In some embodiments, viable cells are isolated from the column. Cells are defined herein as structures that occur as functional units of life (such as in unicellular organisms, e.g. bacteria, protozoa, etc.), or as structural or fundamental units in a biological tissue specialized to perform a particular function in multicellular organisms (e.g. plants and animals). Self-replication is not a necessary property of cells as defined herein; the definition includes entities such as viruses, parasites and exosomes. In certain embodiments, the invention is limited to self-replicating or membrane-bound cells.

Cells are quite fragile and can rupture easily when exposed to a variety of physical conditions such as encountering an object, shear force, turbulence or incorrect solute concentration, temperature and many other conditions. Mechanical cell lysis can be induced by a collision of the cells with micro beads. In fact, this is a common method for cell lysis. However, even a little damage, just one breach of the cell membrane is enough to cause catastrophic damage to a cell. Viable cells can die in vitro simply from incorrect storage, processing, transport, exposure to incorrect temperature (heat or cold), pH, medium, vessel, lack of oxygen, lack of nutrients, buildup of waste gases, collision with a sharp edge or a small channel, etc. Yet, in order to purify cells quickly with a column process, it is important that cells are passed through a column rapidly to be able to capture, wash and recover cells as quickly as possible. This is especially true when the volume from which the cells are being captured is large.

Even though it is important to pass cells through a column quickly, prior art columns have not been able to do this (Braun, R., et al., Journal of Immunological Methods 1982 54, 251-258, Bonnafous et al., J. Immunol. Methods 1983 Mar. 11; 58 (1-2): 93-107 and Ohba, H., et al, Cancer Letters (2002) 184, 207-214). In a few cases, cells have been captured on a column using an incubation process where a small sample is applied to the column and then the sample/column is held or incubated in order to capture cells onto the column. Remarkably and in contrast to the prior art, the instant method of passing cells through the column rapidly without harm may also help or facilitate the improved capture of the cells from flowing samples and large samples.

It is remarkable that intact cells and even viable cells can be captured and purified using the columns and methods of the invention. It is surprising that cells can remain intact even after subjecting them to the methods of the invention. In certain embodiments, cells purified via the instant invention are subjected to a repeated back and forth flow battering motion through a fritted column containing a bed of medium and in some cases, tubing and pumps. That is, cells can be passed rapidly through a column containing a bed of medium. Furthermore, it is surprising that cells can be manipulated and reacted while captured on the column. The cells can remain attached to the column while undergoing tagging or other reactions. The cells may be used as a stationary phase for liquid chromatography. Analyte reagents may interact with the attached cell stationary phase. Finally, the liquid chromatography stationary phase may be removed and recovered. It is remarkable that the stationary phase cells may be recovered in a living, viable state for further use or analysis.

The use of whole cells is an excellent format for cell-based assays for a number of reasons. First, it's possible to work with viable cells, which are closer to an in vivo environment than working with for example, cell extracts, where labile co-factors may be lost or with a single protein, where key functional interactions with other molecules may be absent. In whole cells, targets such as cell surface proteins or protein complexes are likely to be intact and in their native state with respect to folding, etc. Interactions between cells can be studied in some embodiments. Cell signaling pathways can be targeted.

In addition, using cells with column processes has a number of advantages. A plurality of columns can be operated in parallel and their operation can be automated. Columns can be sterilized and operated in a sterile environment such as a laminar flow hood. Column processes are relatively gentle; there is no shaking, spinning or exposure to magnets. The kinetics of drug-target interactions can be examined in a column as described below. Cells, molecules or compounds can be added to columns serially to examine the results of each addition. Cells can be isolated quickly on the columns of the invention which aids in the retention of viability.

Column processes with cells give an increased signal to noise ratio when compared to other cell-based assays. Due to the large surface area of the beads, cells can be concentrated at the capture step to increase signal. Wash steps remove non-specifically bound material, reducing noise in a more consistent and complete manner. As a result, these processes are more sensitive because of reduced noise and yield better statistical data because of the increased signal.

Another method to improve the sensitivity and signal to noise ratio is to improve the detectability of the cell. This is performed by reacting and attaching a detecting reagent to the cell while the cell is attached to the column. By performing the tagging process in this manner, the reaction can be done more completely, which increases the sensitivity, and reproducibly, which reduces the noise, both of which increase the signal to noise coming from the cells.

As described above, the columns of the invention contain a bed of medium onto which the cells are captured. The bed can be comprised of beads or particles held in the column by at least one frit below the bed. In many embodiments, the bed is retained in the column with two frits; one below the bed and one above the bed. It is quite surprising that cells can pass through the frit(s) and the bed of medium and maintain their integrity and in some cases, even their viability.

Consider the physical environment of a liquid sample comprised of cells passing through the frit and bed of medium within a column. The channels through which a cell might flow are not open or linear. Instead, the flow path consists of a variety of interwoven channels, each with varying and perhaps restrictive diameters, and many possible dead-ends marked by repeated turns, bends, winding and twisting. This tortuous path environment is advantageous for the capture of small molecule analytes because the fluid (containing the analyte) receives extensive exposure to the column matrix. However, a cell travelling through this environment could easily be trapped which can kill, damage and/or prevent the cell from being recovered. Adding one or two frits to the column makes the flow path even more tortuous and restrictive. Of course, physically trapping cells within the column matrix is an undesirable outcome quite distinct from targeted cell capture strategies such as affinity binding. Cells that become physically trapped cannot be recovered with an eluent or desorption solvent. Furthermore, if cells are trapped, even temporarily, they could readily rupture or die. This trapping phenomenon was referred by Bonnafous et al. (supra) and teaches away from successful purification of cells by the instant invention.

The columns of this invention have very low back pressures. The columns are packed and constructed to produce these very low backpressures. The columns of the invention have lower backpressures even compared to columns having low back pressure screen frits similar used in previous column technology in which smaller column bed sizes and column body sizes were used (see U.S. Pat. No. 7,837,871). However, the backpressure of the columns of the invention is significantly lower than these earlier columns. In addition, the columns are packed in such a way that the flow of cells through the column flow paths is less restricted and does not harm the cells.

FIGS. 1A and 1B illustrate the surprising nature of the invention. They are a stylistic depiction of the many potential hazards and pitfalls that could be encountered by cells travelling through a column using bidirectional flow. FIG. 1A depicts an aspiration step in which the flow direction 10 is upward. The matrix of the material (e.g., a polymer) is depicted by closed squares 16. Cells cannot penetrate matrix 16. The flow path through a column bed contains many potential nooks and traps for cells. A clear unrestricted flow path 12 enters and exits the bed. Some cells (e.g., 14) may be captured by the column in flow path 12. As the flow proceeds, many or most of the cells 18 enter dead-end flow paths 20 to trap the cells 22 in dead-end or restricted passages 24. There are also nooks (e.g., 26) just off flow path 12 that may trap cell 28.

FIG. 1B depicts the fate of cells resulting from back and forth flow through the column. The flow direction 30 is in a downward direction, reversed from upward direction 10 shown in FIG. 1A. Although increased residence time may allow a greater number of cells 32 to be captured, especially from a flowing stream, this reversal of the flow direction 34 can also exacerbate the undesired trapping of many cells 36. It should be noted that cell 28 remains trapped in nook 26.

Figure 2A:
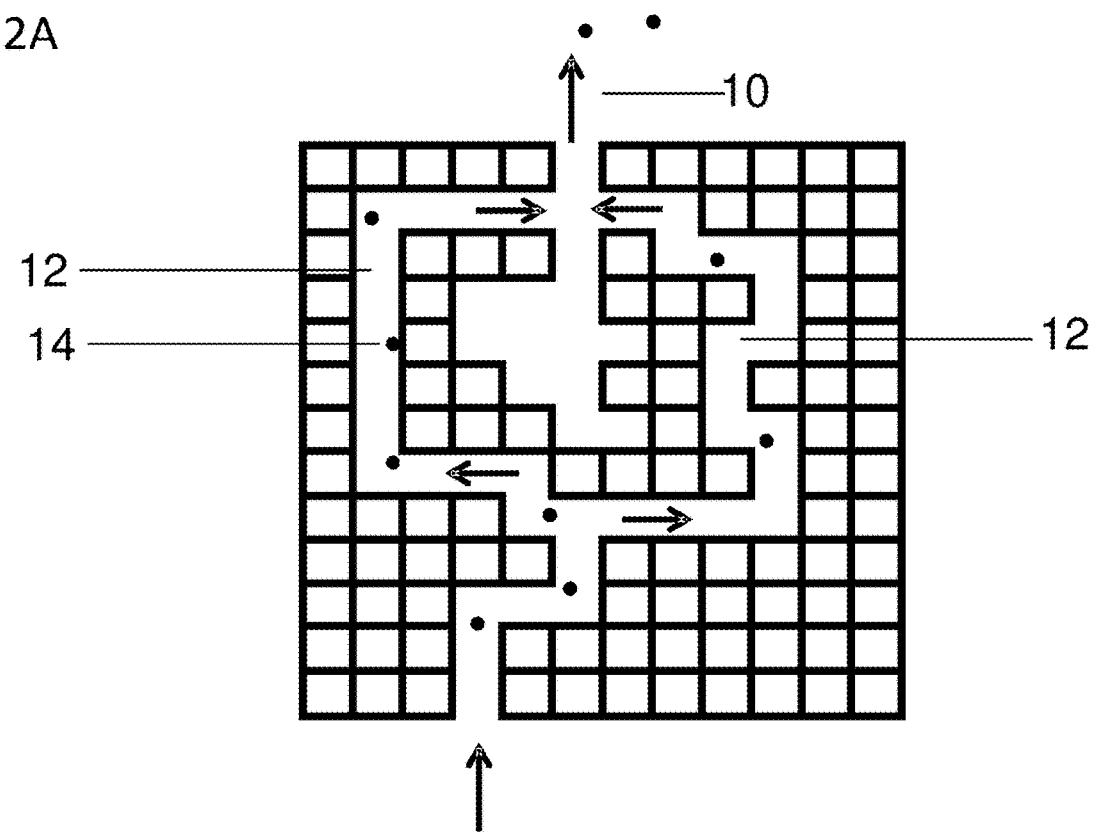
FIGS. 2A and 2B are stylistic depictions of a column that shows how flow paths can be unconstrained in one flow direction, but constrained in the opposite flow direction.
Figure 2B:
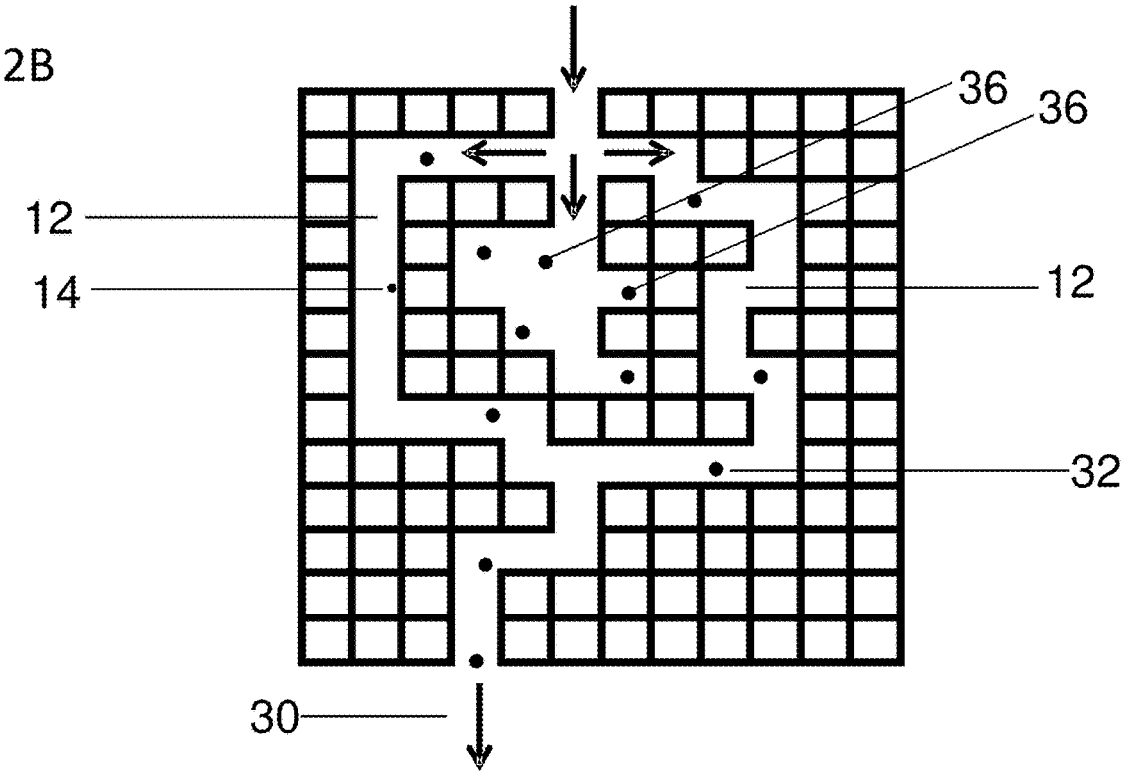

FIGS. 2A and 2B depict the trapping and elution of cells from a column. The recovery of cells from a column is attempted with a downward flow direction 38. Most of the cells 40 remain irreversibly trapped. A few cells 42 may be recovered but may or may not be intact. In addition to the risk of cell trapping, a person of skill in the art would expect the column environment or materials to be inhospitable to cells. It is desirable to recover intact and even viable cells. Intact cells are defined herein as cells having no holes or ruptures in their membrane. The column materials or surfaces, such as the frit or column walls might be incompatible with the cell integrity or viability. Protrusions present in the column wall, bed or frit could easily damage or rupture cells.

Figure 3A:
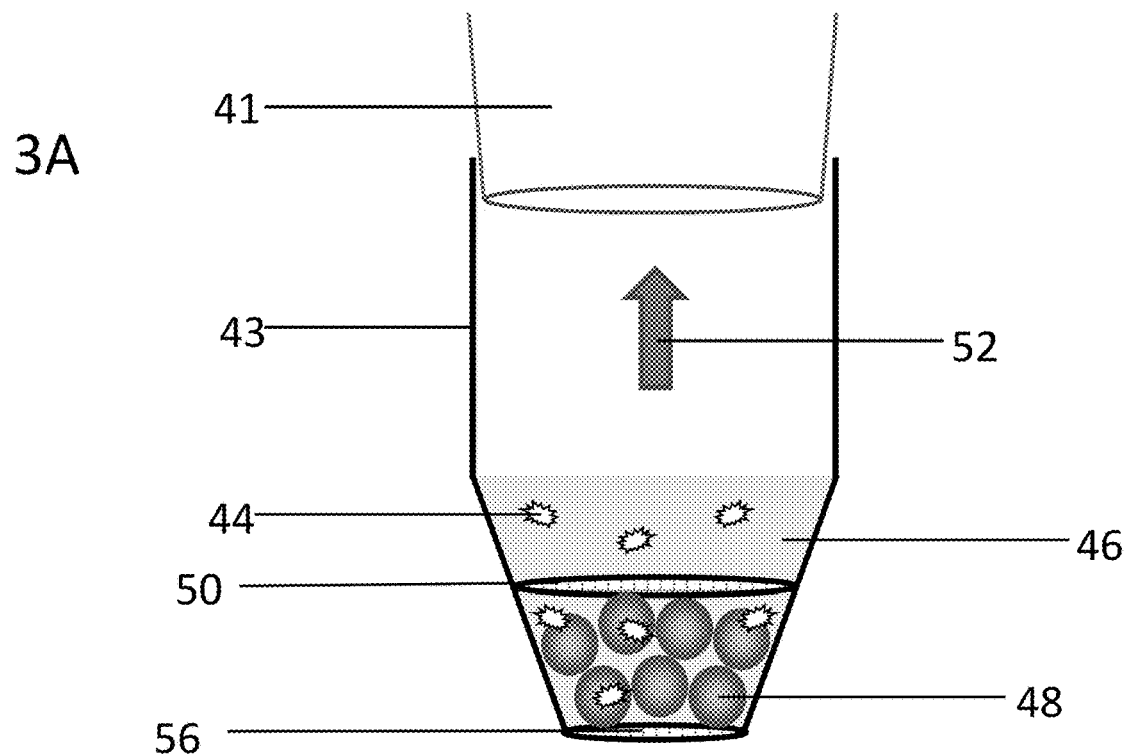
FIGS. 3A and 3B are depictions of a column and method of the invention.
Figure 3B:
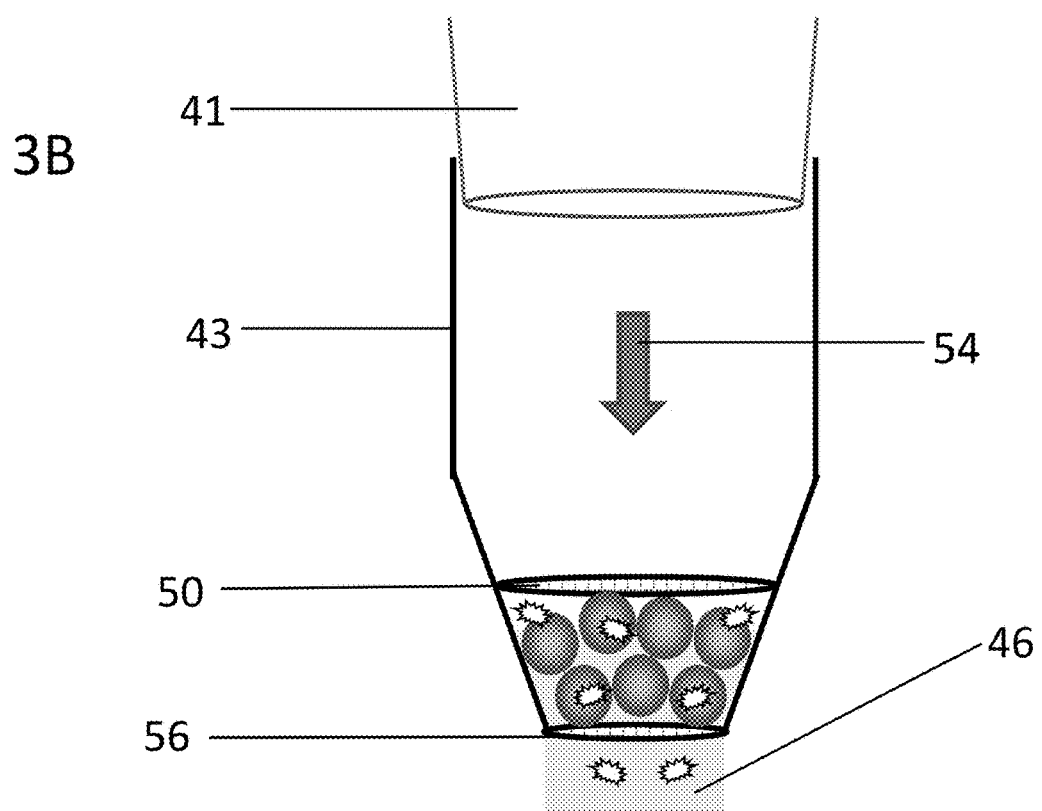

FIGS. 3A and 3B depict a column and method of the invention. Because the column is packed according to the methods of the invention and because the column comprises the frits described herein, it is not subject to the pitfalls described above and shown in FIGS. 1A, 1B and 2A, 2B. Cells in a liquid sample are passed through the column using back and forth flow. In these embodiments, the upper end of column 43 is operatively engaged with pump 41 and sample 46 containing cells 44 is aspirated and expelled through the lower end of the column. During the aspiration step, the sample travels in direction 52, upwards, in through lower frit 56 into the bed of beads 48 and then continues through upper frit 50 (FIG. 3A). During expulsion, the sample 46 travels back downward in direction 54, through upper frit 50, into the bed of medium, through lower frit 56, and exits the bottom of the column (FIG. 3B). These aspirations and expulsions can be repeated multiple times, the desired result being that intact cells are captured by the medium.

However, columns of the invention capture cells in a reversible process. A vast majority of cells either flow through the column or are reversibly captured. Almost no cells are captured in restrictive channels or dead-end channels. The process of cell capture is reversible and the cells are recoverable.

Almost no cells are damaged as they flow through the column, even repeatedly. Intuitively, it seems that the flow paths resulting from back and forth flow would be even more perilous for cells than unidirectional flow, especially when the goal is recovery of intact, stable or viable cells. Cells pass through the column bed and frit(s) multiple times from both directions, increasing the probability of cell damage or death.

This invention provides devices and methods for isolation of cells using a column format. One advantage of the column format is the ability to control the chemical and physical environment of the cell. After cells are captured, reagents can be passed through the column and interact with the captured cells.

The cells can be eukaryotic or prokaryotic. The term, cells as used he will rein is not limited to self-replicating entities. Included in the definition are viruses, exosomes and parasites.

In certain embodiments, the isolated cells are viable. In some applications, the maintenance of cell viability is less important. For example, cells purified on the column may be counted, labeled, analyzed by proteomics, RNA and DNA sequencing, PCR or other biochemical assays.

The Sample

The starting sample is usually a heterogeneous mixture from which cells are purified. The sample can be from any biological source and can contain viable cells. For example, cells can be captured from biological fluids such as whole blood, blood, urine, saliva, spinal fluid or semen, tissues such as nerve, muscle, blood, lymphoid, epithelial, connective, brain or tumor tissue and other samples such as fecal (stool) or hair. In certain embodiments, sample preparation steps are performed prior to the isolation of cells on a column. For example, when cells are captured from blood, the blood can be fractionated by centrifugation and only the buffy coat loaded on the column. Alternatively, whole blood can be diluted or loaded directly on the column. In certain embodiments, the devices and methods can be used for the analysis of solutions containing cells from crime scene samples (e.g. blood or sperm).

In some samples, cells are free and exist individually in solution. There are other samples, such as tissues in which cells are aggregated or form cell-cell adhesions. In addition, there are cells that start off as tissues but then slough off to form free cells. Circulating tumor cells for example exist in blood and may form an adhesion to other places in the body. Sample preparation techniques exist that can mechanically or chemically disrupt and dissociate cells in order to form single cell suspensions. These methods are gentle and in wide use. Kits are available that use enzymatic digestion in combination with mechanical disruption and the option of heat. There are products available from Miltenyi Biotec and Roche Life Sciences for example.

Cells isolated using methods and devices of the invention are not limited to a particular cell type; cells captured by the methods of the invention can be eukaryotic or prokaryotic cells. Eukaryotic cells can be from protozoa, chromists, plants, fungi or animals such as mammals, amphibians, birds, fish, reptiles and invertebrates. Cells can be engineered or wild type.

A non-limiting list of cells that can be isolated by the columns of the invention includes human cells, parasite cells, viruses, epithelial cells, hormone secreting cells, sensory transducer cells, neuron cells, glial cells, lens cells, metabolic cells, storage cells, barrier function cells such as lung, gut, exocrine glands and urogenital tract, kidney cells, extracellular matrix cells, contractile cells, blood and immune system cells, germ cells, nurse cells, interstitial cells, activated B-cells, mature B-cells, cytotoxic T-cells, helper T-cells, activated T-cells, natural killer (NK) cells, monocytes and macrophages, activated macrophages, endothelial cells, smooth muscle cells, dendritic cells, mast cells, fibroblasts (stromal), epithelial cells, adipocytes, stem cells including lab-grown stem cells, radial glia, granulocytes, platelets, erythrocytes, circulating tumor cells, Alexander cells, sperm cells, astroglia, B Lymphoblast, B Lymphocyte, basophil, cortical neurons, cutaneous T cells, lymphocytes, embryonic cells, enterocytes, epithelial cells, transformed cells, immortalized cells, large T antigen, epithelial neuroendocrine, erythroblast, fetal, fibroblast, gecko glial cells, glioblastoma, Hela cells, histocyte, human papillomavirus, hybridoma: e.g., helper T lymphocyte, keratinocyte, killer cell, large cell, lymphoblast, lymphoblast B lymphocyte, lymphoblast Human Immunodeficiency virus, lymphocyte, medulloblastoma, megakaryoblast, melanocyte, melanoma, monoblast, myeloblast, neuroblast, neuroendocrine, osteoblast, pluripotent stem cell, pre-B lymphoblast, promyeloblast, retinoblastoma, Schwann cell, squamous cell, T lymphoblast, T lymphocyte, T-cell.

Cells isolated can be from any tissue. A non-limiting list of tissue type examples follows. lung, ascites, bone marrow, bone, brain, cervix, colon, connective tissue, duodenum, eye, kidney: skin, kidney, liver, lung, lung: pleural effusion, mammary gland, ovary: ascites, ovary, pancreas: lymph node, pancreas, peripheral blood, pharynx, placenta, prostate, retinal pigmented epithelium, skin, spleen, stomach: derived from metastatic pleural effusion, stomach, submaxillary salivary gland, testes, thyroid, tongue, urinary bladder, uterus, adrenal gland, airway epithelium, aorta, bladder, blood, bone marrow, brain, breast, breast derived from metastatic site: pleural fluid, bronchiole, bronchus, carcinoma, cecum, cord blood, cornea, ectocervix, embryo, embryonic kidney, endocervix, endometrium, epithelium, esophagus, eye, fetus, foreskin, gingival biopsy, heteromyeloma, intestine, kidney, lung adenocarcinoma, lymph node, lymph node derived from metastatic site: peritoneal effusion, mammary gland, marrow, mesencephalon, mesothelium, muscle, nasal septum, nervous, palatal, palatal mesenchyme, pancreas, peripheral blood, peritoneal effusion, peritoneum, peritonial effusion, pharynx: derived from metastatic site: pleural effusion, pleura, prostate, rectum, retina, retroperitoneal embryonal tumor, retroperitoneum, skin: derived from metastatic axillary node, skin: derived from metastasis on skin of thigh, small intestine, somatic cell hybrid, stomach, submaxillary, synovium, testis, thymus, thyroid, tonsil, trachea, trunk, umbilical vein, ureter, uterine, vagina, vascular, vein, vertebral epitheloid carcinoma and vulva.

Cells of a particular organ type or part of the body can be loaded onto a column. These include cells from the heart, liver, kidney, bone marrow, gut or from a spectrum of human tissues, including the circulatory, endocrine, gastrointestinal, immune, integumentary, musculoskeletal, nervous, reproductive, respiratory, urinary systems and other types. The cells may be from a specific individual or from the general population. Columns with these cells may be operated alone or in concert with other columns containing cells from other organs or biological systems. The columns can be operated in the chromatographic system in parallel or in series to mimic biological functions. Reagents can be introduced into the columns to determine the interaction of the reagents and the effect on the cells or to study or use the cells as organs.

The Columns

The columns of the invention are comprised of a column body and one or two frits. When two frits are utilized, the column body, top frit and bottom frit define a media chamber which contains a solid phase or bed of medium.

Columns can be made in a wide range of sizes. Column bodies can range from a 10 µL (e.g. a pipette tip) to a 200-mL column. Of course, larger columns can be used to process larger liquid volumes. For example, a 20-ml column containing 1 ml of resin can accommodate approximately 19 ml of a biological liquid sample. Column bed volumes can have a lower limit in the range of 1 µL to 50 µL and an upper limit in the range of 10 µL to 200 mL.

Conventional large and/or long columns usually have higher backpressure than smaller columns. This problem is compounded when the columns are operated with low pressure pumps. Pumps such as syringe pumps or pipette pumps apply positive pressure (head pressure) or vacuum to the column to force the flow of fluid through the column. The pressures applied are low and pumping fluids through large columns is limited. As a result, it is more difficult to pump sample and buffers through large bed column resulting in slower flow rates and longer separation times. This can be a problem for capturing and recovering cells. Longer residence times in a column can harm the quality of the cells recovered and could prevent the recovery of cells, particularly viable cells.

For a given column diameter, increasing the bed height increases the bed volume, which in turn, increases the column capacity for cell capture. A high capacity for cell capture is desirable. However, when pipette tips are used as the column body, there are limits to the possible bed volume that can be used.

In some embodiments of the invention, the columns have a wider diameter and a shorter bed. Such columns will be referred to herein as shorter bed columns. Shorter bed columns of the invention have different properties than the longer bed columns. For example, they can have a different geometry than the smaller columns. Specifically, the ratio of the column diameter to the resin bed height can be greater in the shorter bed columns. These shorter bed columns have a smaller bed height to diameter ratio than conventional columns. Shorter bed columns possess a bed height to diameter ratio of less than 4, less than 3.5, less than 3, less than 2.5, less than 2, less than 1.8, less than 1.6, less than 1.4, less than 1.2, or less than 1. As the diameter of the column increases by a factor of two, the height decreases by a factor of four for a given volume of medium. For conventional chromatography columns, a shorter bed is undesirable because of the decreased number of plates in the column.

Column formats can vary significantly. In some embodiments, the columns are pipette tip columns. Pipette tip columns are defined herein as columns in which the upper end is capable of operative engagement with a pump. Pipette tip columns have an open lower end through which liquids can be aspirated and expelled. In most embodiments, pipette tip columns have a frit to retain media located at the open lower end and an optional frit above the bed. In those columns that possess a single, bottom frit, the bed media particles may become mobile at times during column operation.

Some column formats, including pipette tip columns are capable of dual flow or back and forth flow. When the upper end of the column is attached to a pump, liquids can be aspirated and expelled from the open lower end of the column. The closed or sealed system columns depicted in FIGS. 14 through 19 and described herein are capable of dual flow. Because of dual flow, some columns of the instant invention can be characterized as having two inlets and two outlets. That is, both ends of the column can serve as an inlet and an outlet.

In other embodiments, the column can be in a cartridge or a more conventional column. The column can have end fittings. In these embodiments, the column end fittings can connect to tubes that allow liquid to flow in and out of the column. The ends of the columns can contain frits to hold media in the column chamber. In other embodiments, the columns have inlet and outlet fittings attached to the ends. Tubing can be attached to these inlet and outlet fittings.

In certain embodiments, the columns can be integrated into a multi-well plate. In other embodiments, the column can be positioned within a syringe.

Column Packing

In conventional columns, chromatographic beads packed into a column bed generally orient themselves into a close pack orientation or alignment. Packed beds are three-dimensional but a close-packed bed can best be described first in uniform circles of two dimensions. There are two packing orientations possible: square packing and close packing. Square packing and close packing are well known technical terms for the packing of spheres, but a short explanation is included here. In square packing, circles line up with each other on both axes. Any one circle will touch four different points with four other circles, 90-degree points around the circle. Close packing is where each row of circles is offset by half the diameter of the circles. Any one circle will touch six other circles at six different points. It turns out that the area of the circles in square packing covers 78% of the total area. Close packing is denser and at a lower energy state. Circles in close packing cover 91% of the area. This leaves 9% of the area as interstitial space between the between the circles. For 90-micron diameter beads, the length of the space would be approximately less than 9 microns. This value is estimated because the interstitial space is not circular.

Now, extending this description to three dimensions and describing spheres, not circles, close-packed spheres have multiple layers of beads. In each layer, any one sphere is in contract with six other spheres. In three dimensions, spheres are layered. Each close-packed layer is offset by half the diameter of a sphere as the spheres fill the void spaces left by the previous layer. This layering process leaves two different types of interstitial void spaces between the spheres. One type of interstitial space is tetrahedral because the hole is formed by four touching spheres. The other type of interstitial void is called octahedral because the space is defined by six spheres touching each other in a plane. The octahedral interstitial void space is larger than the tetrahedral space. But generally, the volume of the spheres in a close-packed system occupies approximately 74% of the total volume.

Virtually all conventional columns are packed using compression. For example, see GE Healthcare Life Sciences publication 71-7098-00. Column beds are compressed by using force such as vacuum or pressure. Soft beads such as agarose, Sepharose, cellulose and other similar resins are packed under pressure. When these materials are packed under pressure, the touch beads will deform and squeeze into the interstitial void spaces. With conventional affinity columns, this squeezing can reduce the total bed volume by as much as 15-20%.

Previously disclosed columns were not tightly packed (e.g. U.S. Pat. No. 8,057,668), lightly packed or packed using a light-force packing method (e.g. US2016-0017272). Lightly packed columns were packed under very low pressures, e.g. 3-12 psi. However, even under these low-pressure conditions, the volume of the bed can be reduced by 10% or more, thereby substantially reducing the interstitial void spaces between the beads.

In many embodiments, the columns of the invention do not have bed compression. That is, the bed is quite loosely packed such that the beads are not pressed together. The use of compression results in flow constrictions or dead-end flow spaces that physically trap cells. In certain embodiments, the bed of medium is a fluidized bed.

When compressible beads are used, the bed of medium has a packing density. The packing density of the bed can be measured as a ratio of the volume of beads without compression divided by the same number of beads after the bed has been compressed. As the volume of the column bed is decreased by compression for the same number of beads, the packing density increases. A bed that has been compressed 10% has a volume packing density of 1.00/0.90 which equals 1.11. A bed that has been compressed 20% has a volume packing density of 1.00/0.80 which equals 1.25. A bed that has not been compressed is 1.00/1.00 which equals 1.00. Columns of the invention that contain compressible beads have a volume packing density in the range of 1.00 to 1.05.

Packing columns using pressure leads to constrictions in the path or channel through which the analyte must travel. It was discovered that although bed compression was low with the previously described, light-force packed columns, the bed was still compressed and the beads were deformed, restricting the flow of cellular analytes through the column. These constrictions can reduce the diameter of the flow path at multiple points in any flow channel within the column bed. These constrictions are not harmful for protein analytes because they are small and flow easily into the bead matrix. However, cells have dimensions greater than 0.01 micron, 0.05 micron, 0.1 micron, 0.5 micron, 1 micron, 5 micron, 10 micron, 20 micron, 30 micron, 40 micron or larger.

Cells pass through the column bed in flow channels. These flow channels can be considered tunnels through the bed of medium, the diameters of which are sufficiently large for cells to pass through. Due to the relatively large size of cellular analytes, it is crucial that the diameter of the flow channels is sufficiently large such that cells do not become physically trapped within the column matrix.

Irregular shapes or a large particle size distribution can negatively impact cell capture. For example, beads made from harder substrates such as those based on silica do not compress. However, silica beds can have a distribution of sizes. Small beads can fill the interstitial spaces filling the void. Generally, in conventional chromatography, this is desirable because this reduces the void spaces/dead volumes of a column which in turn reduces the band broadening of an analyte peak traveling through the column. But this is undesirable in columns of the instant invention because these irregular and smaller particles may obstruct flow paths and trap and/or damage the cell. The sharp edges of silica and other hard materials can also trap or damage the cells. In the instant invention, irregular shapes and a large particle size distribution can have a negative effect with all types of media including compressible beads.

The space between the resin particles is also important. This space can increase with loose, non-compressed packing of the column. This space may provide flow channels suitable for capture, washing and recovery of cells without trapping the cells. In many embodiments, the columns can contain a stationary phase or a loosely packed bed in which the beads are not compressed and the flow path will not be restricted. Using this method, the resin can pack and form channels in such a way that cells can move through the resin with reduced chance of damage by physical trapping and an increased chance of targeted capture.

In the instant invention, cell capture was improved by loosely packing the columns in a way that results in relatively large flow channels lacking constrictions or dead-ends. Columns of the invention are characterized by their unrestricted flow paths that allow passage of intact, viable, living cells through the column. Unconstrained flow paths are defined herein as flow channels that allow cells to pass freely through the column bed without becoming physically trapped or damaged. Unconstrained flow paths must extend through the column media and the frit or frits. The columns of the invention are comprised of one or more unrestricted flow paths. In certain embodiments, the columns of the invention contain multiple unrestricted flow paths.

Throughout the length of the column bed, the flow channels should not have constrictions with diameters smaller than those of the cell. In the columns of the invention, all (or substantially all) of the flow channels must have large diameter flow paths that extend through the entire length of the column. Even one constriction in a flow path can cause cells to be trapped.

The columns of the invention contain very few flow paths that restrict the passage of cells. That is, the vast majority of flow channels in the column bed are unconstrained. The percentage of constrained flow channels is less than 2%, less than 1%, less than 0.5%, less than 0.1% or even 0%.

It is surprising that the columns of the invention have an absence of restricted or constrained flow paths. For example, blood cells having a diameter range of 5 to 18 μMare not trapped by columns of the invention. These flow path diameters are very large compared to conventional column flow paths, which explains why at least some cells and frequently many cells are trapped by conventional columns.

Packing columns comprising open channels or unconstrained flow paths is highly counterintuitive and contrary to conventional wisdom because compression is used to prevent channeling during column operation. In conventional column chromatography, channeling is to be avoided at all costs because it causes peak broadening, but more importantly, channeling causes incomplete and poor interaction of analytes with the column stationary phase. When channeling occurs, the liquid mobile phase contacts only a small portion of the packed bed.

The column can be packed in such a way that the flow path diameter is larger than the cell diameter. Column packing can be customized based on the diameter of the cells of the sample. For example, if the cell diameter is 0.5 μm, the column will be packed in such a way that the flow channels are not smaller than 0.5 am. Similarly, if the cells are 5 μm in diameter, the column will be packed in such a way that the flow channels are greater than 5 μm.

Figure 20:
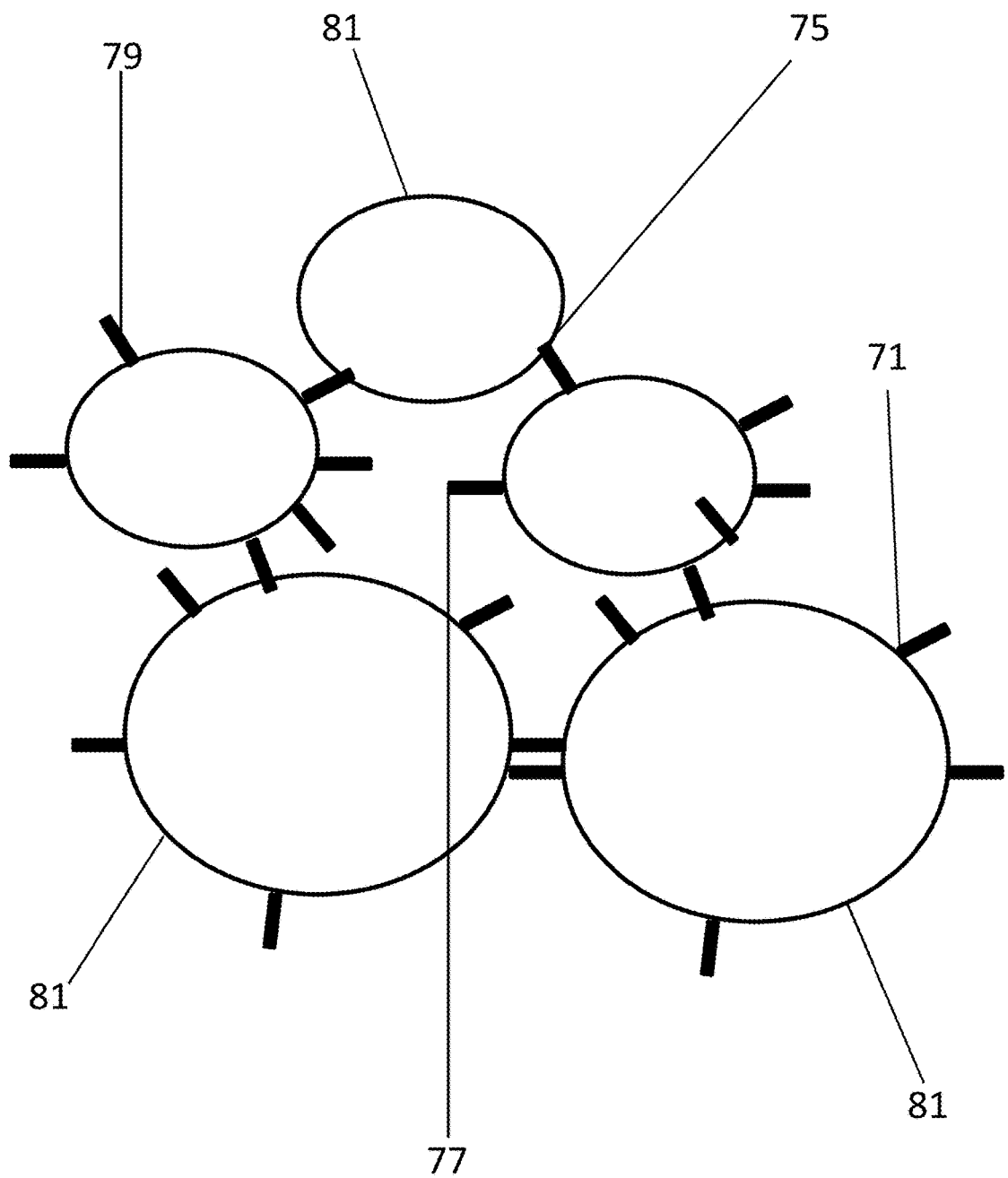
FIG. 20 is a stylized depiction of a medium comprised of surface structures.

In some embodiments, the medium comprises protrusions extending out from the surface. The surface structures or protrusions are part of the bead. A stylized depiction of a medium comprising surface structures is shown in FIG. 20. The circles 81 represent packing media beads or particles. The solid black rectangles 79 represent protrusions or surface structures extending up from the surface of the beads. Proximal end 71 of each protrusion lies at the surface of the bead. Protrusion distal end 75 is in contact with other beads while the distal end 77 is not in contact with other beads.

The purpose of these surface structures or protrusions is to provide physical space between the beads to prevent the medium from packing tightly together. In these embodiments, the beads normally have low or no compressibility. The beads may be organic, inorganic polymeric or any material onto which capture sites may be attached. The protrusions may be organic or inorganic.

The surface structures may have any shape. They may be round cylindrical, pyramidal, irregular etc. However, the surface structures or protrusions must be designed carefully so they do not harm the cells passing through the bed. The morphology must be smooth i.e. shaped in such a way so that cells can impact the protrusions without harming, damaging or killing the cells. The shape of the distal end of the protrusion is especially important. It must not be sharp or pointed or have a shape that will harm, damage or kill cells.

The average distance between the distal end of protrusions and the surface of the bead may be 0.5, 1, 2, 3, 4, 5, 6, 8, 10, 12, 15, 20, 25, 30, 40, 50 microns or more.

In certain embodiments, the protrusion may also be incorporated into a monolith structure as long as the smallest pores of the monolith to do trap and kill cells and the flow paths through the monolith are free of constrictions that trap or kill cells.

Figure 19:
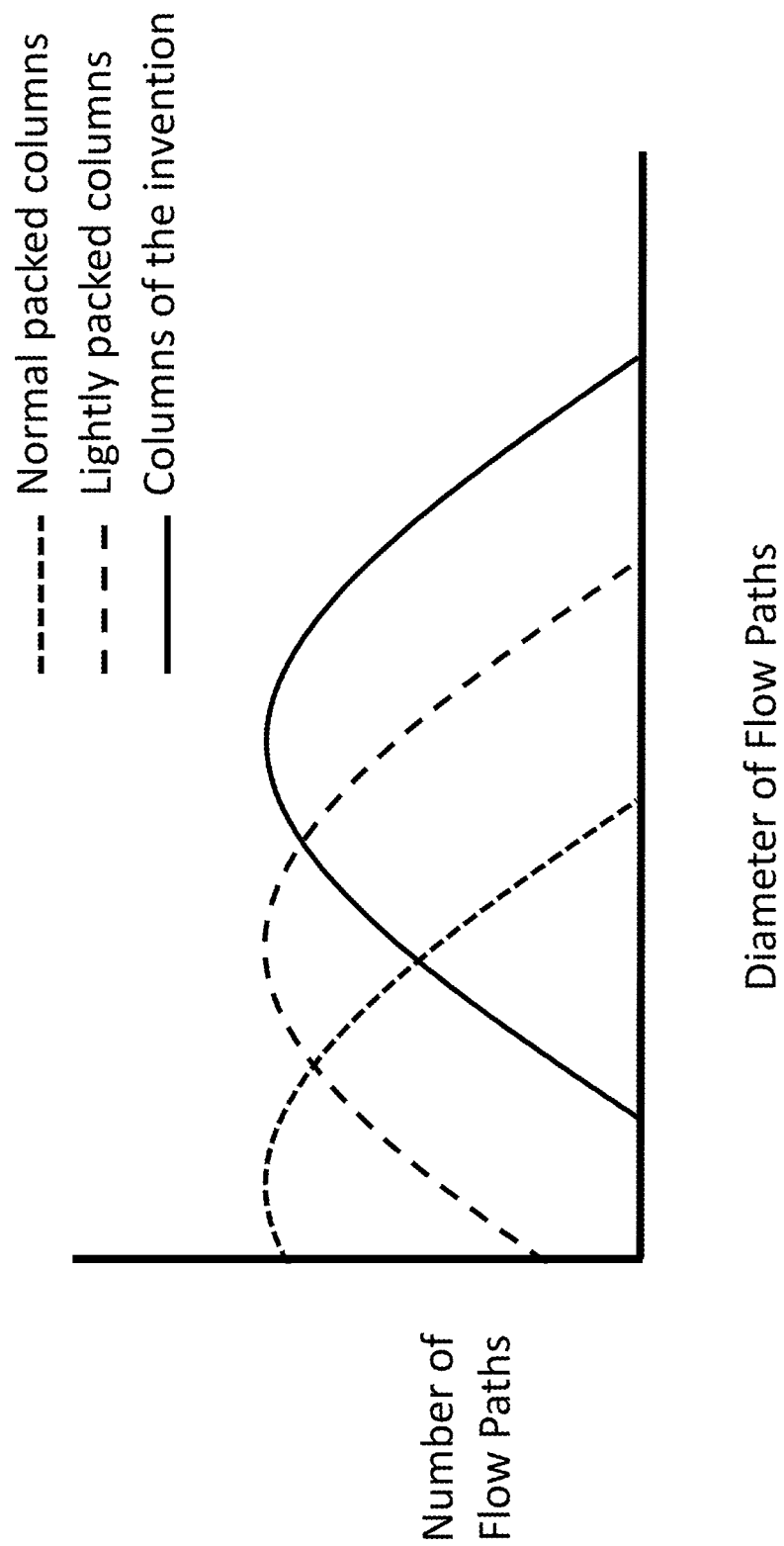
FIG. 19 is a graph that shows distributions of the flow path number and diameter for different column types.

FIG. 19 shows a relative comparison of the flow path number and diameter between normal columns, previously-disclosed lightly-packed columns and the columns of the instant invention. For each column type, the flow path diameters have a bell-shaped distribution. It is important to note that in the columns of the instant invention, the flow paths are unconstrained while the normal-packed and the lightly-packed columns contain constrained flow paths. It is also important to note that the normal-packed and the lightly-packed columns are often compressed or contain obstructions while the columns of the instant invention are not. Because the normal-packed and lightly-packed columns have smaller diameter flow paths and are often compressed or obstructed, they have fewer flow paths through which cells can successfully travel. Cells are more readily trapped in normal-packed or lightly-packed columns. In some embodiments, the average flow path diameter for the columns of the instant invention is greater than 5 μm, 6 μm, 7 μm, 8 μm, 9 μm, 10 μm, 15 μm, 20 μm, 25 μm, 30 μm, 40 μm, 50 μm, 60 μm, 80 μm, 100 μm, 120 μm, 150 μm, 200 μm or 300 μm. In other embodiments, the minimum flow path diameter is greater than 0.5 μm, 1 μm, 1.5 μm, 2 μm, 3 μm, 4 μm, 5 μm, 6 μm, 7 μm, 8 μm, 9 μm, 10 μm, 15 μm, 20 μm, 25 μm, 30 μm, 40 μm, or 50 μm. In these embodiments, no flow paths are completely obstructed to cells larger than the minimum flow path diameter. In certain embodiments, the flow path diameters are in the range of 0.5 μm to 45 μm, 1 μm to 30 μm, 5 μm to 20 μm, 8 μm to 15 μm or 9 μm to 12 μm.

The column bed has a huge number of flow channels, the vast majority of which are unconstrained. The larger the bed diameter, the more flow channels are present. Depending on the bed diameter, the number of flow channels can be on the order of tens of thousands, hundreds of thousands, millions or much, much more into the realm of astronomical numbers.

If the particles are uniform, then the average particle size can be decreased. Obstructions can be created from smaller particles lodging in the flow paths. If the particles are uniform, then the particles can be smaller while still maintaining the minimum diameter needed to produce unconstrained flow paths. Smaller particles can be advantageous because more surface area is available for cell capture.

The columns of the invention, the effective capacity can be dependent upon the accessible surface of the beads within the column bed. The effective capacity of a column should be distinguished from the actual capacity of the column, which is based on the total number of functional groups. As the beads become compressed and touch each other, some of the functional groups that are located on the surface of a bead may be inaccessible to cells flowing through the column and are not available for capture. Since columns of the invention contain beads that have limited or no compression, the effective capacity of the column approaches the theoretical capacity based on the total surface area of the media contained within the column. In some embodiments, the effective capacity is 60%, 70%, 80%, 85%, 90%, 95%, 98%, 99% or 100% of the theoretical capacity. This is another improvement of columns of the invention over previously-described columns.

The column packing of the invention can also be described functionally. Columns that are packed properly allow cells to pass through the bed without being trapped within the resin. In a column packed for use with cells (and lacking an affinity group for capture), at least 90% of the cells can pass through the column bed and frit(s) without being trapped. In some embodiments, at least 90%, at least 95%, at least 96%, at least 97%, at least 98% or at least 99% of the cells can pass through the column without being trapped. These numbers reflect the percentage of cells that can make it through the column in a single pass without being trapped. In a similar vein, unconstrained flow paths in columns for cells are characterized by trapping or damaging less than 1%, 2%, 3%, 4%, 5%, 6%, 7%, 8%, 9% or 10% of the cells passing through the column one time in one direction.

Most chromatography column hardware is designed to operate in a single direction of flow. However, pipette tip columns are unusual when compared with other chromatographic columns because the flow through the column is bidirectional. Non-compressed, loosely packed bed columns can be used with unidirectional or bidirectional flow.

It is quite unexpected that cells subjected to back and forth flow remain intact and viable. While it is difficult to pass cells through a column in a single direction however, it is even more difficult to subject cells to bidirectional flow. Flow paths can be unconstrained in one direction, but constrained flow paths can exist in the opposite flow path direction as shown in FIG. 2. In FIG. 2A, sample aspiration occurs in upward direction 10 and clear unrestricted flow paths 12 enter and exit the bed. Some cells (e.g., 14) may be captured by the column in flow path 12.

FIG. 2B depicts what happens when the flow is reversed. Flow direction 30 is in a downward direction, reversed from upward direction 10 shown in FIG. 2A. Although increased residence time (gained from the use of bidirectional flow) may allow a greater number of cells 32 to be captured, especially from a flowing stream, this reversal of the flow direction can also exacerbate the undesired trapping of many cells such as 36. It should be noted that the opening where the cells are trapped is small and it is difficult for the trapped cells to come out of the hole. This is especially true because the dead-end chamber may have little or no reverse flow.

It is desirable to recover intact and even viable cells. However, it is not possible to recover a large number of viable, living cells from a column having these trapping structures. Many or most of the cells remain irreversibly trapped. Or even if the cells are eluted, the residence time and column structure may damage many or most of the cells. That is, cells can pass freely through the column in one direction but may be trapped or damaged in the opposite direction of flow through the column. In some embodiments, the cell flow paths through the column are unconstrained in both directions of flow through the column.

Medium

The columns can be comprised of beads or particles. The bead size can be quite large, on the order of 100-900 microns or in some cases even up to a diameter of 3 mm. In other embodiments, the bead size is comparable to that used in conventional columns, on the order of 45-150 microns. The average particle diameters of beads used in the invention can be in the range of about 10 to 20 µm to several millimeters, e.g., diameters in ranges having lower limits of 10 µm, 20 µm, 30 µm, 40 µm, 50 µm, 60 µm, 70 µm, 80 µm, 90 µm, 100 µm, 150 µm, 200 µm, 300 µm, or 500 µm, and upper limits of 20 µm, 30 µm, 40 µm, 50 µm, 60 µm, 70 µm, 80 µm, 90 µm, 100 µm, 150 µm, 200 µm, 300 µm, 500 µm, 750 µm, 1 mm, 2 mm, or 3 mm.

Media for columns of the invention may have uniform bead sizes. If the media has a distribution of bead sizes, the smaller beads are still large enough to prevent the closure to cells of the interstitial spaces and flow paths to the cells. The average bead sizes are large, have diameters of greater than 15, 20, 30, 40, 50, 75, 100, 200, and 500 microns. Beads may have surface structure or bumps to prevent the beads from closing interstitial spaces and constraining flow channels for cells. The structure may be small beads, columns, etc. bonded to the beads.

In some embodiments, an impervious resin is used. There are several different ways in which a resin can be designated impervious. Resins can be impervious to cells, impervious to reagents, or impervious to solvents. These resins can be referred to as cell-impervious, reagent-impervious and solvent-impervious. These resins do not contain cell-trapping flow paths.

The cell-impervious resin can have a hydrophilic surface that is compatible with cells. Resins possessing a hydrophilic surface can be impervious only to solvents or impervious to both reagents and solvents.

In certain embodiments, the column resin is said to be cell-impervious. Cells cannot enter the resin matrix however, reagents and solvent may enter the matrix. Examples of cell-impervious media include agarose, organic polymers and silica. Reagents enter through the pores and may react with functional groups in the resin matrix. The solvent enters the matrix through pores and swells the resin.

In other embodiments, the resin is cell-impervious and reagent-impervious but solvent may enter the media matrix. Examples include media comprised of agarose, organic polymers and silicas that are highly cross-linked. The solvent enters the matrix through pores, causing the medium to swell however, swelling is limited. The pores are designed to be small and reagents such as aptamers, large organic molecule and cells do not enter the resin matrix.

Another factor that influences cell, solvent and reagent penetration is the polarity of the medium. Many media are polar and can be spongy. Polar media can hydrate and swell allowing solvents and reagents to penetrate while cells remain on the surface. The column media can be made more impervious by increasing the cross-linking. With a highly cross-linked medium, reagents may not be able to penetrate however solvents might still be able to enter the medium. Another strategy is to increase the polarity on the bead (or particle) surface while the interior remains nonpolar. Solvents will not be able to penetrate such a medium because they cannot form hydrogen bonds. Without solvent penetration, reagents will not be able to penetrate.

In some embodiments, the medium may be completely impervious. That is, the resin is cell-impervious, reagent-impervious and solvent-imperious. Examples include media comprised of agarose, organic polymers or silica in which the matrix does not contain ionic groups that can be hydrated and the crosslinking is high so that solvent swelling is limited or does not occur at all. The pores are small and solvents or reagents such as aptamers, large organic molecules and cells cannot enter the resin matrix.

Use of a resin impervious to cells can be an improvement because cells are large and in many cases, they cannot enter resin bead pores. Most prokaryotic cells range in size from 0.2 to 5.0 µm in diameter and most eukaryotic cells range in size from 1.0 to 100 µm in diameter. The reduction in non-usable surface area will decrease reagent costs as the capacity of the column is d and decreased. In some embodiments, resins are impervious to cells and reagents. The reagents will not travel to locations of the column that are unreachable by the cells and therefore lesser amounts of reagents are needed. The use of a resin with the rigid structure will also facilitate easier column packing procedures.

Example 18 describes the synthesis of a biotinylated silica resin. First, hydroxyl groups were added to the bead surface. Then, amine groups were produced by reacting silanol with the hydroxyl groups. In a third step, biotin is reacted with the amine groups.

In certain embodiments, the column medium is a hydrated gel resin. Gel resin is non-rigid and must be packed carefully. Also, in these embodiments, the resin may be coated with a high boiling point liquid prior to use as described in published U.S. Patent Application US20050045543.

In many embodiments, cells are captured on the surface of the beads and not in the interior however, in certain embodiments, this may not be the case. Cells can be captured in large pore media. The number of cells that can be captured depends on the diameter of shape of the cells and the available surface to which cells can be reversibly captured as a monolayer. Beads that are compressed restrict or eliminate the flow path through which cells can move without getting trapped. Compressed beads reduce the effective surface area of the bead which in turn, reduces the effective capacity of the resin to reversibly capture cells.

In certain embodiments, the column medium can be a monolith, a filter or a combination of materials. Monolith substrates for cells can have microporous through-pores which make up large, continuous and unconstrained flow paths. The monolith mesopores must be small enough that cells cannot enter and become trapped or damaged. Resin mesopores can have diameters in the range of 2 to 50 nm.

Column Frits

In certain embodiments of the invention, one or more frits are used to contain the bed of medium within a column. The frits of the invention are porous, since it is necessary for fluid to be able to pass through the frit. The frit pore size should be large enough to prevent plugging with cells or cell debris. That is, the frit pore size is large for cells to pass through but small enough to retain the solid phase or bed of medium. It is important that the frit does not provide dead-end or restricted-end flow paths that could potentially trap or damage cells. It is desirable that the frit have little or no affinity for liquids or cells with which it will come into contact during the column use.

In certain embodiments, one frit (e.g., a lower, or bottom, frit) extends across the open channel of the column body. The bottom frit is usually attached at or near the open lower end of the column however, other configurations are possible. A bed of separation medium is positioned inside the open channel and in contact with the bottom frit. In many embodiments, a top frit is employed, however it is not mandatory. In certain embodiments, there is a gap between the bed of medium and the top frit. This gap is referred to as a bed-frit gap.

Frits of various pores sizes and pore densities may be used provided the free flow of liquid is possible and the solid phase is held in place. However, the frits must have specific porosity characteristics. It is not only a matter of having sufficiently large pores. The pore shape is important as well. Pores cannot be destructive or restrictive to cells.

Frits of the invention preferably have pore openings or mesh openings of a size in the range of about 5-500 µm. In certain embodiments, the pore size is in the range of 10-200 µm, 33-150 µm, e.g., about 33-43 µm. Frit pore sizes of 20, 33, 37 and 43 µM pore size are acceptable. Of course, increasing the frit pore size can only be done if the packing material retained.

The frits of the invention can be made from any material that has the required physical properties as described herein. Examples of suitable materials include polymers, fiber, fabric, plastic (including sintered plastic), nylon, polyester, polyamide, polycarbonate, cellulose, polyethylene, nitrocellulose, cellulose acetate, polyvinylidine difluoride, polytetrafluoroethylene (PTFE), polypropylene, polysulfone, PEEK, PVC, metal and glass. However, any suitable material that meets the above functional requirements can be used for the frit.

Certain embodiments of the invention employ a membrane screen as the frit. The use of membrane screens can provide low resistance to flow and hence better flow rates, reduced back pressure and minimal distortion of the bed of medium. The membrane can be a woven or non-woven mesh of fibers that may be a mesh weave, a random orientated mat of fibers i.e. a "polymer paper", a spun bonded mesh, an etched or "pore drilled" paper or membrane such as nuclear track etched membrane or an electrolytic mesh.

Some embodiments of the invention employ a relatively thin frit. The frit or frits should be sufficiently thin such that cells will not become trapped or die within the frit during column operation. In most embodiments, the frit thickness is less than 6000 µm or less than 4000 µm (e.g., in the range of 20-4000 µm, 40-2000 µm, or 50-350 µm). In certain embodiments, the frits are less than 200 µm thick (e.g., in the range of 20-200 µm, 40-200 µm, or 50-200 µm), or less than 100 µm in thickness (e.g., in the range of 20-100 µm, 40-100 µm, or 50-100 µm). However, thicker frits can also be used in some embodiments, frits up to 1 mm, 2 mm, 3 mm, 4 mm, 5 mm and even 6 mm thick may be used if the pore size of the frit can be increased dramatically.

The frit can be attached to the column body by any means which results in a stable attachment. For example, the screen can be attached to the column body through press fit, welding or gluing.

Frit and Column End Design for Cells for Different Types of Chromatography

Partitioning and frontal breakthrough chromatography are performed using unidirectional flow while step gradient or displacement chromatography can be done using either unidirectional or bidirectional flow.

Since flow is unidirectional for partitioning and frontal/breakthrough chromatography, there are specific design considerations necessary for the frits and column ends. Specifically, the dead volume of the column end, flow distributor and the frit are critical for performing the separations without diffusion of the chromatographic analyte band and without trapping cells. In addition, in order to load the column, the column end flow diffusors and frits must accommodate back and forth flow without trapping the cells. Cells must be able to travel through the frits in either direction without getting trapped. Conventional liquid chromatographic column ends and frits are not compatible with cells because they will trap cells. Using a screen frit does not solve the problem because this frit is flexible and the bed may move with the reverse direction flow. This will cause the column bed to move into the column end flow distributor when the flow is reversed and could cause the cells to be damaged. The flow distributor must be deeper and compatible with cells (not damage them) to prevent this even though this design will result in band broadening.

The design described above can also be used for step gradient and displacement chromatography. In a liquid chromatographic format, the flow is likely to be unidirectional although the column flow could be used in unidirectional or bidirectional flow format and cell loading of the stationary phase is likely to be bidirectional. The dead volume of the column end and frit is not critical to performing the separations since there is no chromatographic analyte band to diffuse. Nevertheless, the frit and column end should not trap cells.

Sterile Columns and Systems

In certain embodiments, the columns, reservoirs, tubing and flow paths are sterile. In these embodiments, the columns materials can be assembled from sterile components in a sterile setting such as a clean room. Components can be sterilized by methods known in the art such as filtration, irradiation, chemicals and heat. In other embodiments, the columns are operated in a hood such as a laminar flow hood to maintain sterility. In some embodiments, the columns and methods of the invention are used with anaerobic conditions.

Alternatively, terminal sterilization can be performed. Terminal sterilization is defined herein as sterilization of the manufactured columns. In this embodiment, the columns and system can be sterilized prior to use. Once the system with column is made sterile, the system may be sealed to maintain sterility. Outside materials cannot enter the sealed system. There may be venting valve or other types of valves or membranes in the system but these would only allow the out flow of materials and not allow contamination of the system.

Column sterilization after manufacture can be performed by a number of methodologies. In one embodiment, columns can be assembled and then sterilized by autoclaving as described in the examples below. Alternatively, terminal sterilization treatment can be performed for example, by irradiation.

The column hardware, media and system can be sterilized. For example, water swollen gels and other column media may be sterilized. Impervious organic and inorganic column materials may be sterilized. Substrates based on silica and other inorganic materials may be sterilized.

Figure 21:
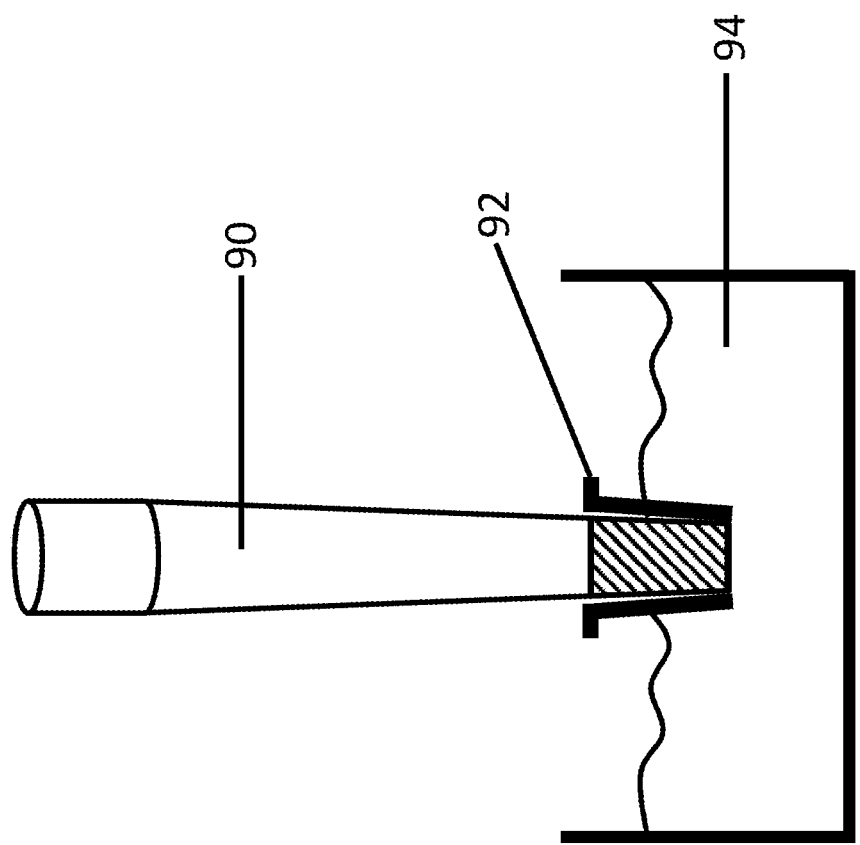
FIG. 21 is a depiction of a column partially covered by a removable casing.

In certain embodiments, the column can be covered or partially covered with a removable casing. In FIG. 21, column 92 is immersed in liquid 94. Liquid 94 can be a sample solution, a wash solution, an eluent or any other solution. Removable casing 90 covers the open lower end of the column 92. Removable casing 90 can be attached to the column 92 or it can be attached to the sample vial or well.

The column may be positioned in a vial, tube or microplate well using a depth controller so that only the end of the column is in the liquid and no liquid touches the outer sides of the column. This can be accomplished with or without a casing. In another embodiment, the column may be raised and lowered as liquid is expelled or aspirated to prevent liquid from contacting the outside of the column.

Removable casing 90 prevents cells from adhering to the exterior of the column. For example, if cells from a heterogeneous sample solution adhere to the exterior of the column, they may not be the particular cells desired from the column purification. Instead, they may be contaminants. These contaminating cells may not wash off during the column wash steps. The casing can be removed prior to column washing or column elution. Casing 90 can be sterile or sterilizable.

Column Operation

In the methods of the invention, a sample containing cells is passed through a bed of medium or solid phase within a column. The cells are captured on the column medium while other sample constituents pass through the column. In certain embodiments, only a particular subset of the cells within the sample are captured. The column with captured cells is washed and the purified cells can be released from the column or manipulated on the column.

Although it is not required, liquids can flow through the columns in both directions. This type of column operation is referred to as back and forth flow, bidirectional flow or dual flow. In some embodiments, liquids are aspirated and expelled through the lower end of the column. In these embodiments, a pump, such as a liquid handling robot is operatively engaged with the upper end of the column and liquids (such as the sample, wash and eluent) are aspirated and expelled through the lower end of the column. Multiple aspirate expel steps are often used with back and forth flow. Back and forth flow can also be used with conventional columns such as those used in a liquid chromatograph.

In other embodiments, dual flow can be performed without direct engagement of the column with a pump. This configuration is illustrated in FIGS. 14 through 18.

In other embodiments, unidirectional flow is used to pass liquids through the column. In these embodiments, fluids are added to the upper end of the column and flow is in a downward direction through the column and out the lower end. In some embodiments, the unidirectional flow is used to pass liquids from one end of the column to the other end. In some embodiments, the inlet and outlet of the column may be interchanged.

The sample can be passed through the column with the use of a pump, a vacuum or even gravity. Pumps include those used in liquid chromatograph instruments such as piston pumps and pressure type pumps, as well as pipettes, syringe, peristaltic, pressure, syringe pump or liquid handing robot, or any pumping device that can impart positive and negative pressures to liquids or gases above the liquid that can force the liquid through the column.

When unidirectional flow is used, liquids can be passed through the column multiple times. That is, the flow-through can be collected and loaded onto the column again.

The method can be performed in an automated or semi-automated fashion. In some embodiments, the method can be performed manually using a hand-held pipette or a syringe. The term "semi-automated" is defined as a process by which some steps are performed under electronic control while other steps, such as moving the column from well to well are performed manually. For example, a semi-automated method could be performed using the electronic E4 pipette (Mettler-Toledo International Inc.) which is comprised of firmware and software. The semi-automated process can be performed using a single channel electronic pipette or in parallel using a multichannel pipette.

The term "automated" is defined as a process by which sample processing is performed by a robotic system controlled by a computer program. In these embodiments, the timing for each processing step and programming of the pumping device can be programmed such that the purification can be performed in a walkaway fashion. This automation process may be performed with columns in parallel. Even though backpressures are low and the capture, wash and purification of cells is a difficult process, columns of the invention may be operated in parallel with automation.

Because of the very demanding design and performance requirements of capturing the cells in a reversible fashion, columns of the invention may have different flow properties than conventional columns. For example, the backpressure of the column may be very low. However, the backpressure may increase as the column becomes loaded with cells that have been captured. Nevertheless, automated methods can be used successfully to purify and recover live cells with column, methods and apparatus of the invention.

Often, it is desirable to process a biological sample having a large volume. Sample volumes larger than the column bed volume or even larger than the entire column volume can be processed using back and forth flow. In some embodiments, back and forth flow is performed by repeated aspiration and expulsion of the sample. It is surprising that repeated aspiration and expulsion can be performed without harming the cells within the sample. Alternatively, large sample volumes can be loaded onto the columns through the open upper end and collected from the open lower end. Sample loading can be performed repeatedly as described above.

In some embodiments, the biological sample comprises a flowing stream. In these embodiments, the cells are captured by the column from a stream that is pumped into the column and flows through the column. In certain embodiments, the flowing stream is passed back and forth through the bed of medium. In these embodiments, the flowing stream can be passed back and forth through the bed of medium multiple times. Because the capture process is performed from a flowing stream, samples larger than the bed volume of the column can be passed through the column.

Columns of the invention are capable of capturing cells from large sample volumes, i.e. samples larger than one bed volume or one column volume. In some embodiments, the sample comprises a flowing stream. This is in contrast to previously-described columns which require small volume samples limited to one bed volume and smaller (Braun et al., Bonnafous et al. and page Ohba et al. (supra)). In addition, Braun and Bonnafous teach that it is necessary to incubate the sample for several minutes before the separation process can begin. It appears that their columns required incubation time for the cells to become captured by the resin and therefore were not capable of capturing cells from a flowing sample. Without being bound by theory, it appears the cells had to diffuse or undergo orientation to the affinity site in order for the capture process to occur.

Intuitively, it seems that a slow flow rate would be advantageous for the capture of cells on a column. There are several reasons for this. First, the cell surface biopolymers (often proteins, carbohydrates or peptidoglycan) must have the correct orientation to be captured by the antibody (or another capturing group) on an affinity resin. Second, there must be sufficient time for the affinity group to bind and capture the cells. These two parameters improve as the flow rate is decreased. Furthermore, a slow flow rate would be gentler, lessening the chance of damage to the cells by the solid surface of the medium and/or column hardware.

However, even when slow flow rates are used, cells travel through the column at relatively high linear velocities. A high linear velocity would be expected to exacerbate the potential problems described in an above. For example, a cell could become lodged in a dead-end with greater force, making it more difficult to free the cell. While a cell travelling at a relatively slow velocity might slide or sidle around an obstacle, a cell travelling at a high velocity might be ruptured.

However, in the columns of the invention, rapid flow rates are possible. The use of rapid flow rates decreases separation time which positively impacts cell viability. Although the cells may be subjected to more frequent and harder collisions within the column body, they are able to survive even with repeated passes through the column and even with the use of back and forth flow. Even through rapid flow rates would be expected to decrease the opportunity for the cell capture, they allow capture of the cells without damage.

Columns of the invention can accommodate a variety of flow rates, and the invention provides methods employing a wide range of flow rates, oftentimes varying at different steps of the method. In various embodiments, the flow rate of liquid passing through the media bed falls within a range having a lower limit of 0.01 mL/min, 0.03 mL/min, 0.04 mL/min, 0.05 mL/min, 0.07 mL/min, 0.08 mL/min, 0.1 mL/min, 0.2 mL/min, 0.3 mL/min, 0.4 mL/min, 0.5 mL/min, 0.6 mL/min, 0.7 mL/min, 0.75 mL/min, 0.8 mL/min, 0.9 mL/min, 1 mL/min, 2 mL/min, 3 mL/min or 4 mL/min. The upper limit can be 0.1 mL/min, 0.2 mL/min, 0.3 mL/min, 0.4 mL/min, 0.5 mL/min, 1 mL/min, 2 mL/min, 4 mL/min, 6 mL/min, 10 mL/min, 20 mL/min, 30 mL/min, 40 mL/min, 50 mL/min or greater. Liquids passing through the column include an equilibration solution, a sample solution, a wash solution, an eluent and other solutions/reagents/analytes.

With columns that have a shorter bed length, it is possible to use smaller liquid volumes relative to the bed volume. For instance, in the smaller, previously-described columns a minimum of two bed volumes could be aspirated. But in the shorter bed columns, it is possible to aspirate one bed volume of liquid. But for columns of the invention, the shorter distance through the column presents a lower chance of damaging or killing the cell. For example, a column with a 12-mm diameter has a height of only 9 mm. A column with 14.5 mm diameter is 5.8 mm height. This compares to conventional pipette tip column based on a 1 mL tip volume of having a 4-mm diameter contains a column of in an 8-mm height, but having only a 100 μL bed volume, one tenth the volume of the larger columns described above.

Next, because of the large cross section area, the column can be made to operate with lower backpressure and lower chance of squeezing the bed restricting the flow paths for cells. It is possible to use smaller liquid volumes relative to the bed volume. For example, in the smaller, previously-described columns a minimum of two bed volumes could be aspirated. But in the shorter bed columns, it is possible to aspirate one bed volume of liquid.

Furthermore, higher flow rates can be used with the shorter bed columns. Columns that have a body size of at least 1 mL and a bed volume in the range of 100 µL to 50 mL can be operated using significantly faster flow rates than columns having a smaller column body and bed volume. Flow rates in the range 1 mL/min to 12 mL/min and faster can be used. In large column embodiments, the flow rate for passing liquids through the column can be within a range having a lower limit of 0.01 mL/min, 0.05 mL/min, 0.1 mL/min, 0.5 mL/min, 1 mL/min, 1.5 mL/min, 2 mL/min, 2.5 mL/min, 3 mL/min, 3.5 mL/min, 4 mL/min, 4.5 mL/min, 5 mL/min, 6.5 mL/min, 7 mL/min, 7.5 mL/min, 8 mL/min, 8.5 mL/min, 9 mL/min, 9.5 mL/min, 10 mL/min, 10.5 mL/min, 11 mL/min, 11.5 mL/min, 12 mL/min or greater. The upper limit of the flow rate can be in the range of 60 mL/min, 70 mL/min, 80 mL/min, 90 mL/min, 95 mL/min, 100 mL/min or greater.

As a result of the higher flow rates, the separation times are shorter and cells can be isolated and recovered in a very short time. In some embodiments, cells can be isolated from a biological sample in less than 45 minutes, less than 30 minutes, less than 25 minutes, less than 20 minutes, less than 15 minutes, less than 10 minutes or even less than 5 minutes.

Large columns may capture large numbers of cells with back and forth flow while keeping the cells alive. A column with 100 µL bed may capture and recover 1 million to 50 million cells. A column with a bed size between 1 mL and 10 mL may capture and recover 10 million to 500 million cells. Some shorter bed column sizes such a 1 mL, 2 mL, 3 mL, 4 mL and 5 bed columns can capture and recover living cells at the quantities of 100, 200, 300, 400, and 500 million or more. They may capture and recover 1, 2 and 5 billion or more living cells.

A faster flow rate reduces the time for purification which is advantageous for cell viability. On the other hand, a fast flow rate is more likely to damage the cells. Fast flow rates through columns of the invention reduce the time it takes to capture cells and these shortened capture times are beneficial for the maintenance of cell viability. Gently flowing cells through a column is in itself, dangerous to the cells. However, rapidly pushing cells through a column is even more perilous. Increasing the flow rate increases the possibility of killing the cells.

Bidirectional flow combined with rapid flow rates is even more dangerous for cells. The cells can be pushed past points of rugged morphology within the column medium and then suddenly and abruptly, the flow direction is reversed. The instant of precipitously reversing flow provides a shock to the cells. The possibility of this shock harming the cells increases as the flow rate increases. While increasing the flow is desirable for reducing capture time, damaging or killing the cells is of course, undesirable.

In columns of the invention, the flow rate of cells traveling through the column can be adjusted to decrease capture time. The total capture time can be less than 120 minutes, less than 100 minutes, less than 90 minutes, less than 80 minutes, less than 70 minutes, less than 60 minutes, less than 55 minutes, less than 50 minutes, less than 45 minutes, less than 40 minutes, less than 35 minutes, less than 30 minutes, less than 25 minutes, less than 20 minutes, less than 15 minutes, less than 10 minutes, less than 8 minutes, less than 7 minutes, less than 6 minutes, less than 5 minutes, less than 4 minutes, less than 3 minutes, less than 2 minutes, or less than 1 minute. In some embodiments, the capture time can be rapid, on the order of 2 to 10 minutes.

In this range of capture times, it is possible to maintain viability of the vast majority of the cells. For each pass through the column, it is possible to keep more than 90%, more than 95%, more than 97%, more than 98% or more than 99% of the cells alive.

After cells are purified from a column, a percentage of the viable cells present in the sample remain viable. Approximately 95%, 90%, 85%, 80%, 75%, 70%, 60%, 50%, 40%, 30%, 20% or 10% of the viable cells from the sample remain viable after purification.

It can be important to purify cells rapidly to maintain viability. Isolation of cells can be performed remarkably fast using the columns and methods of the invention. Cells can be isolated in less than 3 hours, less than 2½ hours, less than 2 hours, less than 90 minutes, less than 75 minutes, less than one hour, less than 50 minutes, less than 45 minutes, less than 40 minutes, less than 35 minutes, less than 30 minutes, less than 30 minutes, less than 25 minutes, less than 20 minutes, less than 15 minutes or less than 10 minutes. In other embodiments, cell purification can take longer, particularly when viability is not as important.

Columns of the invention have unconstrained flow paths that allow the cells to be captured from flowing streams. Capture is often a fast process and because of this, capture can be performed with a flowing sample. This is a great improvement over the previously-described columns because capture from a flowing stream allows the capture of samples from volumes that are larger than the bed volume and in some cases, larger than the column volume. In one embodiment, the flowing sample stream is aspirated and expelled back and forth through the column at least once. In many embodiments, the sample is passed back and forth through the column bed multiple times. There is no practical limit to the number of back and forth cycles although lengthy procedures may be harmful to the cells, particularly viable cells.

In order for a cell to be captured from a flowing stream, the following things must occur.
1) A cell must migrate, be directed or transferred to the capture site.
2) The cell must rotate and orient its position so that a marker, receptor or entity on the cell is in contact with a capture entity on the column media.
3) The capture reaction/interaction must occur.

The capture process can be slow, resulting in the capture of only a small fraction of the cells in the sample. Capture efficiency can be increased with back and forth flow. For methods of the invention, bidirectional flow of cells through the column effectively increases the time of possible capture of cells by the column without trapping or killing the cells. The residence time may vary depending on the flow rate of the fluid through the column. (The residence time is the total time in which the cells are flowing through the column during the capture process.) The total residence time for capture can be 1, 2, 3, 4, 6, 8, 10, 15, 20, 25, 30, 40, 50, 60, 80, 100, 120, 150, 200 or 300 minutes.

Cells can be captured from multiple sample aliquots processed in series or from multiple cycling from a large volume sample aliquot. Capture from a flowing stream may be performed with unidirectional or bidirectional flow. In some embodiments, the capture is performed using slow flow rates, 100-200 µL/min but the capture process is still successful with faster flow rates, up to 10 to 40 bed volumes/minute.

Cells traversing the column several times before being captured have a greater chance of becoming damaged or trapped. With each flow through of the sample through the column, 95%, 96%, 97%, 98%, 99%, 99.5%, 99.9%, 99.99% percent of the cells are either captured or travel through the column and are not trapped or injured. With each cycle, additional cells may be trapped. For example, if 99% of cells are unharmed with each pass through the column, this number is reduced to 99% of 99% or 98% with the second pass (or one complete back and forth cycle). With each additional cycle, the reduction is another 2%.

When a sample containing cells is passed through the column, at least a portion of the cells are captured by the material within the column. The sample may comprise a variety of cell types, e.g., blood and it may be desirable to capture only one cell type. In some cases, rare cells such as circulating tumor cells are captured on the column medium. In these cases, the cells captured can be a very small percentage of the total number of cells in the sample. In some embodiments, the number of cells captured can be relatively small.

In some embodiments, viable cells can be recovered from the column. In these embodiments, it is important to maintain the appropriate conditions for cell viability at all stages of the column process and additionally, following cell elution. Factors such as pH, buffering, viscosity, carbon dioxide concentration, temperature and osmolarity must be considered. For example, viable cells can be stored in sterile buffers such as phosphate buffered saline (Ca/Mg$^{++}$ free) or HEPES (N-2-hydroxyethylpiperazine-N'-2-ethanesulfonic acid) or others known in the art. These buffers can contain EDTA, HBSS (Hank's balanced salt solution), human serum, and fetal bovine serum and other constituents. One reference for such media is the UCSF Cell Culture Facility website.

Columns and methods of the invention keep cells alive by supplying the necessary chemical, biological, mechanical and environment conditions. Solutions surrounding the cells must have the appropriate gas content (oxygen), pH, viscosity, buffering and nutrients. It may be necessary to remove waste products. Because cells are fragile and can die readily, it is not always easy to determine the cause of cell death. Cell death can be due to mechanical battering or inhospitable environmental conditions.

However, viable cells are not required for all applications. For instance, it may be desirable to determine whether a particular cell type is present in a sample or to perform PCR on cells isolated using the columns and methods of the invention.

After the capture step, the columns can be washed with buffer or water to remove any material that is not specifically bound to the column medium. The wash liquid can be passed through the column by any means or rate described above for the sample. The volume of the wash liquid can be greater than that of the column. The wash step may be repeated once or several times.

Following the column wash, the cells can be eluted from the column by passing an eluent through the column. A variety of elution strategies are described below. However, when viable cells are desired, the eluent and elution conditions must be chosen carefully to avoid or minimize harm to the cells. The eluent can be passed through the column by any means described above for the sample. The elution step may be repeated once or several times. In certain embodiments, the eluent can be incubated on the column for a period of time to increase the efficiency of cell elution. After the purified cells are eluted from the column, they can be analyzed by any means desired.

Because the columns are packed to minimize cell trapping, they can be very efficient in isolating the desired cell type. It is possible to capture at least 50%, at least 60%, at least 70%, at least 80%, at least 85%, at least 90%, at least 95% and possible even 100% of the desired cells from a particular sample.

After cells are isolated, an assay may be performed to determine cell viability or to count the number of viable cells.

In the columns and methods of the invention, cells can be captured from rapidly flowing streams. As an example, for column with diameters ranging from 2 mm-4 mm, capture is from cells moving through the column at 0.05-20 mm/sec, 0.1-10 mm/sec, 0.2-5 mm/sec, 0.3-3 mm/sec, 0.4-2 mm/sec and 0.5-1 mm/sec. The linear velocity at 0.1-10 mm/sec corresponds to absolute flow rates of about 100 μL/min to 10 mL/min respectively. For the columns with diameters ranging from 4 mm-10 mm, capture can be from cells moving through the column at 0.005 mm/sec-30 mm/sec, 0.01 mm/sec-20 mm/sec, 0.05-20 mm/sec, 0.1-10 mm/sec, 0.2-5 mm/sec, 0.3-3 mm/sec, 0.4-2 mm/sec and 0.5-1 mm/sec. For some commonly used columns, the linear velocity at 0.1-10 mm/sec corresponds to absolute flow rates of about 500 μL/min to 5 mL/min respectively. As another example, for column with diameters ranging from 10 mm-15 mm, capture is from cells moving through the column at 0.05-20 mm/sec, 0.1-10 mm/sec, 0.2-5 mm/sec, 0.3-3 mm/sec, 0.4-2 mm/sec and 0.5-1 mm/sec. For these columns, linear velocity at 0.1-10 mm/sec corresponds to absolute flow rates of about 1 mL/min to 100 mL/min respectively. As yet another example, for column with diameters ranging from 15 mm-40 mm, capture is from cells moving through the column at 0.05-20 mm/sec, 0.1-10 mm/sec, 0.2-5 mm/sec, 0.3-3 mm/sec, 0.4-2 mm/sec and 0.5-1 mm/sec. For these columns, linear velocity at 0.1-10 mm/sec corresponds to absolute flow rates of 5 mL/min to 500 mL/min respectively. Columns of the invention of other diameters operate at linear and absolute flow rates corresponding relative to the examples given.

The following steps are example of a chromatographic procedure for purification of cells for recovery and detection.

1. Treat or activate column or cells to make the column suitable for cell capture.
2. Load cells onto column from a flowing stream.
3. Wash nonspecifically-bound materials from the column using a flowing stream.
4. Optionally, tag cells with a reagent that reacts with a group on the surface of the cell. The tag can react with a surface group or entity that is optionally different than the attachment group used to capture cells on the column.
5. Optionally, measure or quantify the cells attached to the column. Detection methods can include spectrophotometric, microscopic, infra-red, surface and transmission VIS/UV, fluorescence, chemiluminescence spectrophotometers.
6. Optionally, lyse cells or elute the components of the cells for analysis. The lysing may be done partially, or over a longer time period using gentle conditions to remove components of the cell for processing and/or analysis.
7. Remove and recover cells for analysis and/or further processing including growth, transformation, cell therapy or any further research and development.

Active Movement

The movement of reagents and cells in cell-based assays and magnetic bead assays is based on diffusion. Reagent and cells travel through solution by diffusion. This process is attractive because it is not disruptive to cells i.e. the processes treat cells gently. This is important because rapid changes in the chemical and physical environment of the cells can injure or kill the cells.

But with diffusion, fine control of the chemical environment can be difficult to attain because the addition and removal of reagents is slow and residual materials cannot be removed easily. It may be difficult to change reagents that are in contact with the cells or control changes in the buffer concentration or pH. The diffusion process can be slow and cells can die simply through natural causes.

We use the term active movement to describe the use of pumps to force cells, by a fluid pumping action, to travel in a flowing stream to and from the column medium or solid phase, tubing and column connections, fittings and frits. Active movement can be performed by unidirectional flow and bi-directional flow. The term active movement is also used to describe the pumping of reagents to immobilized cells.

The danger of active movement is killing cells by rapid changes to their environment. Cells can be trapped or injured by shearing forces produced by the rapid movement of cells or fluids moving to and past cells. One advantage of active movement is being able to perform an operation of cell manipulation rapidly. Another advantage is ability to have a rapid and fine control of the chemical environment surrounding the cells. These advantages also allow new manipulation and control of cells and reactions of cells with reagents. In addition, active movement allows the cells to be used as a stationary phase in a chromatographic column.

There are several types of cell active movement. These include:
1. Active movement of cells to and from a column, to the column medium and to capture functional groups, all without damage to the cells. This allows the opportunity of the column to capture live cells in a reversible form.
2. Active movement of reagents to live cells on the column to able to perform chemical reactions and interactions with the live cells. Rapid and fine control of the concentration of the reagents is possible while removing other reagents that may have side reactions. Even finer control is achieved with the use the cell-compatible, low dead volume frits and impervious column media. Through control of chemical or physical changes such as pH or concentration, interrogation of reagents and cells is performed. Reagents and interactions can be driven to completion rapidly and completely.
3. Active movement and recovery of biological products from the live cells on the column. The products may change depending on how the cells are treated or by changing the materials that may contact the cells. The products may be studied or used.
4. Active movement removal of non-specific materials (background cells and other nonspecific or undesired molecules) from cells of interest. This removal it possible to accurately distinguish between cells of interest and background cells to dramatically improve purity, detection, chemical interrogation, chemical reactions, etc.
5. Active movement of reagents to add and to remove analyte reagents from cell stationary phase column. Analyte reagents can be added and recovered rapidly from the cell stationary phase column for analysis or further operations under controlled chemical elution conditions.
6. Active movement of reagents to remove cells from column. Living cells can be recovered rapidly from the capture column for analysis or further operations under controlled chemical elution conditions. Removal can be complete and rapid. Cells can be detected on line for real-time quantification and interaction measurements.

Active movement is rapid but gentle and can help cells to remain alive. Living cells can be tagged on column under controlled chemical conditions. Living cells and reagents that interact with living cells can be interrogated on column under controlled chemical conditions.

Another aspect of active movement for living cell columns is the precise and accurate control of the flow of reagents through the column. The concentration of the reagents flowing to and from the cells on the column is controllable and predictable. The use of low dead volume frits and a column that does not contain dead spaces or spaces that trap liquids/materials helps to accomplish this. Another means for accomplishing precise and accurate control of the column flow is the use of a medium impervious to cells, solvents and reagents. With an impervious medium, reagent concentrations are not diluted (or changed unpredictably in concentration) by penetration of reagents or cells into the media matrix. Such changes in reagent concentration by reagent penetration are explained in the following section.

Impervious Resins and Strategies to Prevent Dilution of Reagents and Eluents

In some embodiments of the invention, reagents are introduced into a column using unidirectional flow. It was known that adding reagents in a unidirectional flow can be slow due to slow reaction kinetics. But it was discovered that an additional factor appeared to contribute to the slow reactions. Introduction of a reagent into a column forms the wave front of the reagent traveling through the column. It was discovered that for some embodiments of the columns of the invention, the wave front for a slug traveling through the column would travel more slowly than expected. Furthermore, the shape of the wave front was diffuse and the width of the wave front was broad. Cells could not be eluted quickly and effectively.

Next, it was discovered that the time necessary for adding reagents to a column was slower than expected. For example, adding an antibody capable of capturing a cell to an agarose solid phase required an appreciable time to react with all of the functional group sites. Also, effective elution of cells from a column required a large amount of eluting reagent and an appreciable amount of time and flow.

It was discovered that some reagents would enter the interior of the bead whereas the cells would penetrate very little or remain on the surface of the bead. Because of this, reagents were being sequestered or consumed in locations within in the columns where cells were not present. Thus, some portion of the reagents introduced into the column were consumed by the solid phase but did not serve any useful function with regard to capture of cells, reacting with cells or release of cells.

The degree of reagent sequestration depends on the type and size of reagent. Materials enter or penetrate columns of the invention to different degrees and depths, depending on the size of the reagent and the properties of the solid phase. Both reagents and solvents penetrate media such as agarose, Sepharose, cellulose and other water-swollen media. Solvents generally penetrate silica gel, dextran, swollen iron exchange media, polystyrene and acrylate. Reagents may or may not enter these substrates. Cells that enter these substrates may become trapped.

Furthermore, it was discovered that when a solution containing reagents was pumped into a column, the localized concentration of some reagent materials would change depending on whether or not the material entered the matrix of the column media. If the reagent entered the bead matrix, then the localized concentration of the reagent would decrease, especially relative to a reagent that did not enter the resin matrix. The degree to which the concentration decreased depended on the degree the reagent could enter the resin phase. The smallest reagents were diluted most while intermediate reagents were diluted to a lesser degree and the largest reagents, such as cells, usually did not decrease the localized concentration of the material introduced into the column.

It was discovered that the concentration profile of a material pumped through a column is a wave front that travels through the column as it is being pumped. The concentration profile of reagent that penetrates the resin matrix will decrease and be lower than the concentration profile of a reagent that does not penetrate the bead. That is, the wave front is delayed if the reagent penetrates the column medium.

Several methods for controlling the localized reagent concentration of reagents introduced to columns were developed. For the consideration of this discussion, the term reagent may refer to very large materials (e.g. cells, DNA, RNA), larger materials (e.g. antibodies, fragments of antibodies, lipids, nucleic acids, aptamers), smaller materials (e.g. buffer reagents, organic compounds, salts, bases, and acids) or very small materials (e.g. solvent molecules). The first method involves changing the reagent concentration in proportion to the degree of solid phase porosity. If any particular reagent penetrates the resin, then the concentration of that reagent must be increased in correspondence to the degree of penetration into the resin. That is, for reagents that penetrate the resin matrix, the concentration of the reagent can be increased to compensate for dilution of the reagent. When more than one reagent is involved, reagent concentrations can be adjusted relative to each other depending on whether or not a particular reagent (or material or molecule type) penetrates the resin matrix.

In some embodiments, it is necessary to increase the concentration of a reagent that penetrates the solid phase in order to maintain a uniform concentration of that reagent throughout the column. For example, for a reagent that penetrates the resin completely, the reagent concentration can be increased by up to almost 100%. because the resin matrix occupies approximately 50% of the column volume. If the reagent only penetrates 50%, then the concentration of reagent could be increased 50% to maintain the localized concentration of that reagent relative to a non-penetrating reagent.

A second method is to control and limit the penetration of reagents and solvent into regions of the media where cells do not reside. One way to accomplish this is to use a resin impervious to the specified reagent or solvent. For example, in certain embodiments, a resin can have very small pores that don't allow entry of most reagents. If it is desired to control or increase the concentration of any particular reagent as the wave front is passed through the column, then the column solid phase is chosen to be (or reacted to be made) impervious to that particular reagent. The reagent or solvent penetration into a medium substrate can be less than 50%, less than 20%, less than 10%, less than 5%, less than 1% or it is possible to have no penetration at all.

Reactions in which controlling reagent penetration into the substrate should be considered include 1) activating a column for capture, 2) capturing a cell from solution 3) washing non-specific materials away from a column containing captured cells, 3) reacting a label or tag with cells captured on a column, 4) washing unreacted label or tagging reagent from a column, 5) introducing an eluting reagent to release captured cells from a column, 6) introducing reagents to controllably lyse cells captured by a column, 7) introducing analyte reagents to a column containing a cell stationary phase and 8) eluting or displacing analyte reagents from a cell-based stationary phase column and other reagents used in a cell purification, cell detection and cell-based stationary phase chromatography.

Affinity resins have a gel-like, hydrophilic structure that swells in the presence of water or polar solvents. These resins have a polar and/or ionic matrix. As the polymers swell, the pores expand and enlarge. The swollen polymers contain pores that allow solvents and reagents to diffuse in and out of the resin. Resins are compatible with cells, at least in part, due to their polar/ionic/hydrated properties.

The swelling can be significant. For example, cellulose, agarose or Sepharose can swell to 5-10 times its original size. In the swelling process, pores are opened up producing beads with a pore diameter up to 500 angstroms and larger allowing biomolecules to migrate and diffuse into the bead along with the solvent.

In certain embodiments, the resin can be completely impervious to solvents and reagents. In these embodiments, the matrix is not hydrated however, the surface is polar and hydrated. The use of a completely impervious resin is quite unorthodox. To our knowledge, impervious resins have not been used with cells. It is not obvious to make an impervious, the surface of which could be harmful to the cells.

The advantage of impervious resins is that the concentrations of solvent and reagent can be controlled. Solvents and reagents are not diluted when they are applied to the column. The concentration of solvents and reagents can be applied to cells captured on the column. With an impervious resin, dilution of solvents and reagents occurs only from their entrance into the column interstitial spaces. After the initial introduction, dilution remains constant and the solvent/reagent concentrations are not affected by diffusion into the resin matrix. Because the reagent/solvent concentration is down, smaller amounts can be used for operations such as cell labeling or sell elution. Even the use of smaller absolute amounts of reagents/solvents, the concentration remains high.

In some embodiments of the invention, a polymer substrate is used that does not swell upon exposure to water. In substrates which do not swell in water (or solvent), buffer molecules, biomolecules and/or cells cannot enter the pores in the substrate. The substrate may be polystyrene, polyacrylate type, polyester, metal, or other olefin polymer or other polymer, or inorganic substrate materials. Inorganic polymers include polysiloxane and polyphosphazene, silicone, etc. Inorganic materials include aluminum oxide, zirconia, silica, etc. Organic polymers include low density polyethylene (LDPE), high density polyethylene (HDPE), polypropylene (PP), polyvinyl chloride (PVC), polystyrene (PS), nylon, nylon 6, nylon 6,6, Teflon (Polytetrafluoroethylene), thermoplastic polyurethanes (TPU), polytetrafluoroethylene (PTFE), polychlorotrifluoroethylene (PCTFE) and other polymers. When exposed to water, the particle size increase of these substrates is less than 5%, less than 4%, less than 3%, less than 2%, or less than 1%. Swelling may be controlled by adjusting the polarity of the interior of the substrate to be nonpolar or non-hydrophilic. When the polarity is adjusted, aqueous solutions cannot enter or hydrate the beads. In certain embodiments, the polarity of the surface of the medium can be increased while the interior of the beads remains nonpolar. This strategy will limit solvent and reagent penetration.

In other embodiments of the invention, the swelling of the substrate upon exposure to water may be greater, but still limited. In these cases, the interior of the bead or substrate may be more hydrophilic, but swelling is limited because the polymer beads are crosslinked or held together physically. In some embodiments, water may not enter the substrate. Buffer molecules, biomolecules and cells also may not enter the substrate. In some embodiments, some limited amount of water and buffer molecules may enter the substrate, but biomolecules and cells may not enter the substrate. When exposed to water, the particle size increase of these substrates is less than 50%, less than 40%, less than 30%, less than 20%, less than 10%, less than 5%, less than 4%, less than 3%, less than 2%, or less than 1%.

Another counterintuitive method for increasing the effectiveness of reagents was developed for columns of the invention. Consider a column in which cells are connected to a streptavidin resin via a biotinylated antibody. Cells can be eluted from such a column with biotin in a first order displacement reaction. A first order displacement reaction means that there is a one-to-one replacement of the eluent molecule to the biotinylated antibody holding the cell to the media. The reaction is an equilibrium reaction. The equilibrium of the reaction shifts as the biotin concentration is increased.

However, another way to increase the effectiveness of the elution reaction is to lower the capacity of the resin. With a lower capacity resin, a lower concentration of biotin can be used to drive the equilibrium reaction to same extent. In a related manner, if the same biotin concentration is used in a pervious (permeable) higher capacity resin versus a less pervious lower capacity resin, then the lower capacity resin will respond faster. The lower capacity resin will also respond to a greater extent with the same concentration of biotin because the equilibrium reaction will be shifted to more complete reaction. That is, a reaction can be driven to completion by adjusting either the resin capacity or the reagent concentration. More complete elution or displacement of the biotinylated antibody occurs with the effectively higher amount of reagent. Also, if the reagent is consumed in the reaction, as they are in displacement reactions, then the mass amount of the reagent needed is also lower with the lower capacity of the resin. How do we claim this?

Finally, there is another factor that controls the amount of each reagent needed and the effectiveness of reagents added to the column. The actual capacity of the resin is determined by the actual number of functional groups in a resin. This can be expressed for example as milliequivalents of functional group per mL of bed volume of a column or milliequivalents of functional groups per gram of resin, etc. But the effective capacity of a resin can be much different and often lower than the actual capacity. The effective capacity of the column is a measure of sites that function in capturing, processing, using and recovering cells in the column. The effective capacity does not include functional sites that do not capture cells. In some columns of the invention, the ratio of actual capacity to effective capacity is quite high because most of the sites are not accessible to the cells. In the columns of the invention, the ratio of actual capacity to effective capacity can be in the range of 1000 to 1 or 100 to 1. However, if the column does not contain functional groups that are impervious to cells, then the ratio is much lower, which can be desirable. In some columns of the invention, the ratios are much lower and require lower reagent concentrations. Desired ratios of actual capacity to effective capacity for cells for columns of the invention include 10 to 1, 5 to 1, 3 to 1, 2 to 1, 1.5 to 1, 1.2 to 1 and is 1.1 to 1, 1.05 to 1 and 1 to 1.

In some embodiments, an impervious resin is beneficial. By limiting placement of the functional groups to sites accessible to the cell, two things are accomplished. First, the capacity per unit volume or mass of the column resin is lowered making the reagents introduced into the column more effective per unit concentration. In some embodiments, improved columns of the invention have capacities in the range of 1000 cells per mL of column bed volume, 5000 cells per mL of column bed volume, 10,000 cells per mL of column bed volume, 20,000 cells per mL of column bed volume, 30,000 cells per mL of column bed volume, 40,000 cells per mL of column bed volume, 50,000 cells per mL of column bed volume, 60,000 cells per mL of column bed volume, 70,000 cells per mL of column bed volume, 80,000 cells per mL of column bed volume, 90,000 cells per mL of column bed volume, 100,000 cells per mL of column bed volume, 300,000 cells per mL of column bed volume, 500,000 cells per mL, 750,000 cells per mL, 1,000,000 cells per mL, 2,000,000 cells per mL, 5,000,000 cells per mL, 10,000,000 cells per mL, 20,000,000 cells per mL, 50,000,000 cells per mL, 100,000,000 cells per mL, 200,000,000 cells per mL or 500,000,000 cells per mL of column bed volume.

Second, the ratio of actual capacity to effective capacity for cells becomes lower. This also increases the effectiveness of reagents introduced into the column because they are interacting only with functional group sites that are accessible or useable by cells. In some embodiments, this means placing or having the sites on the surface of the bead or surface of the media. Still, from a standpoint of recovering as many purified cells as possible, it is desirable to increase the column capacity as much as possible. One way of accomplishing this is to increase the total surface area of a column by decreasing the bead diameters contained in the column. However, increasing the capacity by decreasing the bead size may not be possible because this may also increase the restrictions to flow with smaller spaces between the resin beads. Therefore, although it is counterintuitive, low capacity resins can be more desirable for this reason as well.

Depending on the cell size, the column media may be impervious to cells. The percentage of cells able to penetrate the column medium can be less than 10%, less than 5%, less than 1% or 0% (no penetration) into the resin matrix.

Temperature

The columns of the invention can be operated at any temperature. In some embodiments, the column is operated at low temperatures (e.g. in a cold room) while in other embodiments, the column can be operated at room temperature or at a temperature greater than room temperature. The optimum temperature for running the column will depend on parameters such as the application, the column medium and the cell type.

In some embodiments, the sample and the column are operated/maintained at a lower temperature such as 4° C. In other embodiments, the column is operated at a temperature in the range of −50° C. to 50° C., −40° C. to 40° C., −30° C. to 30° C., −20° C. to 20° C. or −10° C. to 10° C. In some embodiments, the sample and/or column are maintained/operated at higher temperatures up to 35° C., 37° C., 40° C., 45° C., 50° C., 55° C., 60° C., 65° C., 70° C. or higher. In some embodiments, the sample and/or column are maintained at sub-ambient temperatures or higher than ambient temperatures depending on the particular property studied or used.

The appropriate temperature may be used to help preserve cells. These can be sample cells, cells captured on the column or cells eluted from the column.

Temperature may also be used to change the nature of the cells being captured and control selectivity of the column to capture particular cells.

For example, incubation of red blood cells at 37° C. may affect the expression of some antigens, such as CD35 and CD11b. While temperature may not affect expression of CD15s, CD44, or CD62L, maintaining a temperature of 37° C. may accelerate apoptosis of neutrophils with subsequent shedding and decreased expression of CD16. Peripheral blood neutrophils prepared at 4° C. may express less CD35 and CD11b than those prepared at room temperature, suggesting release of some granular contents at higher temperatures. It has been found that changes in surface marker expression of CD11/CD18 occurred with temperature change, such as warming neutrophils from 4° C. to 37° C.

Capture

Various strategies and mechanisms can be used for cell capture on the column medium. For example, cells can be captured using affinity, ion exchange, hydrophobic interaction, reverse phase, normal phase, hydrophilic interaction or ion pairing.

In some embodiments, the column medium is comprised of a capture entity and cells are captured by virtue of their ability to bind or associate with the capture entity. The capture entity is defined herein as any component or functional group capable of cell capture. In some embodiments, the medium is comprised of multiple different capture entities. Capture entities can bind cell surface markers. Non-limiting examples of capture entities include antibodies, antibody fragments such as Fabs or Fv (scFv) fragments, bispecific antibodies, aptamers, adhirons, proteins (including combinations of proteins), peptides, polypeptides, drugs, hormones, steroids, lectins, ion exchange groups, carbohydrates, nucleic acids, organic molecules, ions, metals, metal complexes, organic functional group, hydroxyl reactive group, amine reactive group, ester reactive group, ketone reactive group, aldehyde reactive group, sulfur reactive group, phosphate reactive group, combinations of these and any chemical group that binds to, or associates with a cell.

Capture entities on the column medium can associate with cell surface markers. In certain embodiments, the capture entity can be tagged or labeled. Labels include fluorescent molecules, biotin, HIS tags, FLAG tags and others described herein. For example, a biotinylated antibody can bind a cell surface marker and cells can be captured using a streptavidin resin. Tags can be incorporated into the capture entity and/or the linker. Nonlimiting examples include biotin or biotin analogues, avidin, streptavidin, HIS tags, TAP tags, FLAG tags and fluorescent tags.

Antibodies can be monospecific or bispecific. A monospecific antibody can associate with a particular cell surface marker. A bispecific antibody is an artificial protein comprised of fragments from two different antibodies that can be used to capture two different cell types simultaneously.

In some embodiments, the column is comprised of more than one functional group or capture entity so that multiple cell surface markers can be captured simultaneously. In some embodiments, a column comprised of several capture entities can be used to capture several cell types at once. In other embodiments, a column comprised of more than one capture entity can bind different cell surface markers present on the same cell type.

Figure 5:
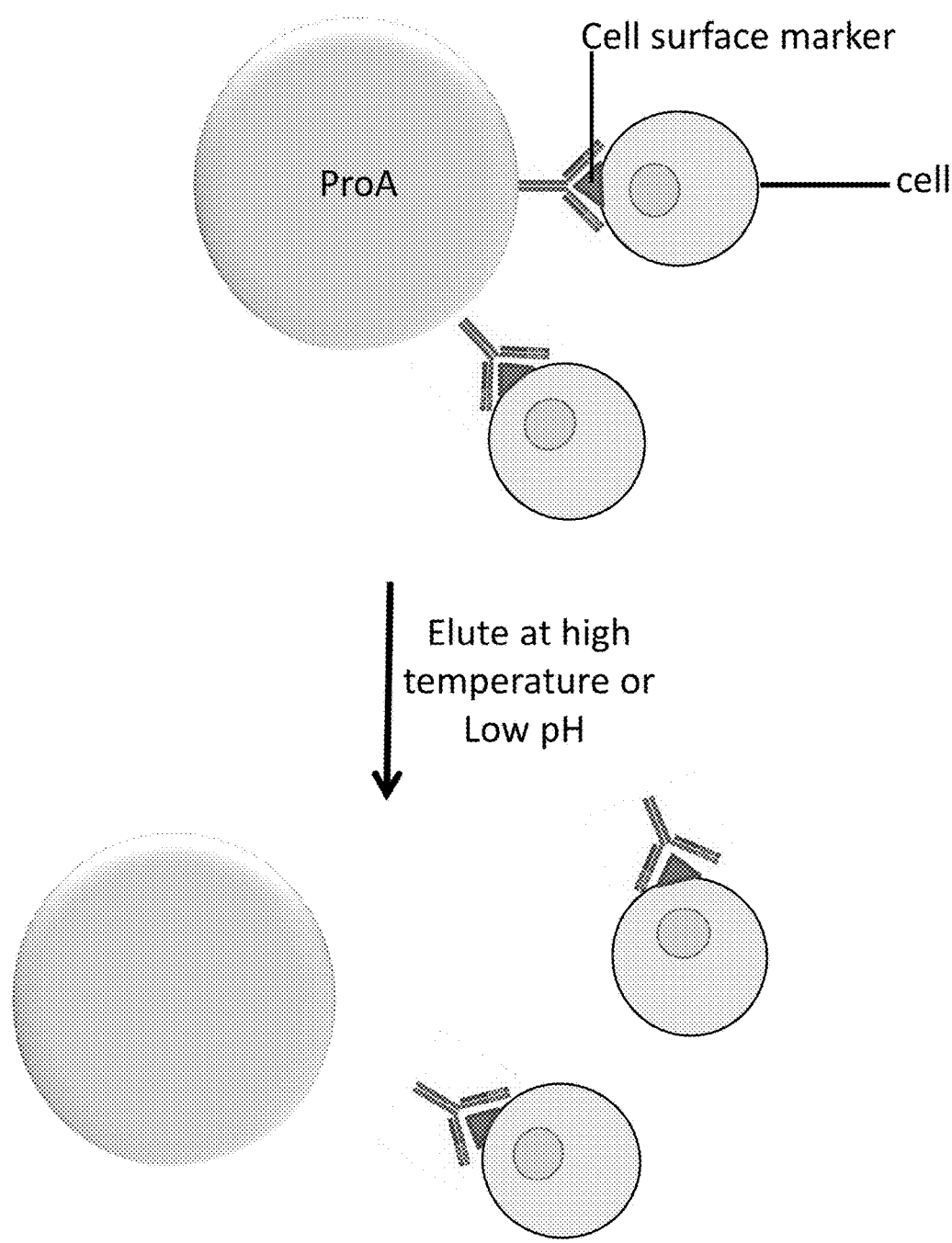
FIG. 5 is a depiction of an embodiment of an antibody capture and release strategy.
Figure 6:
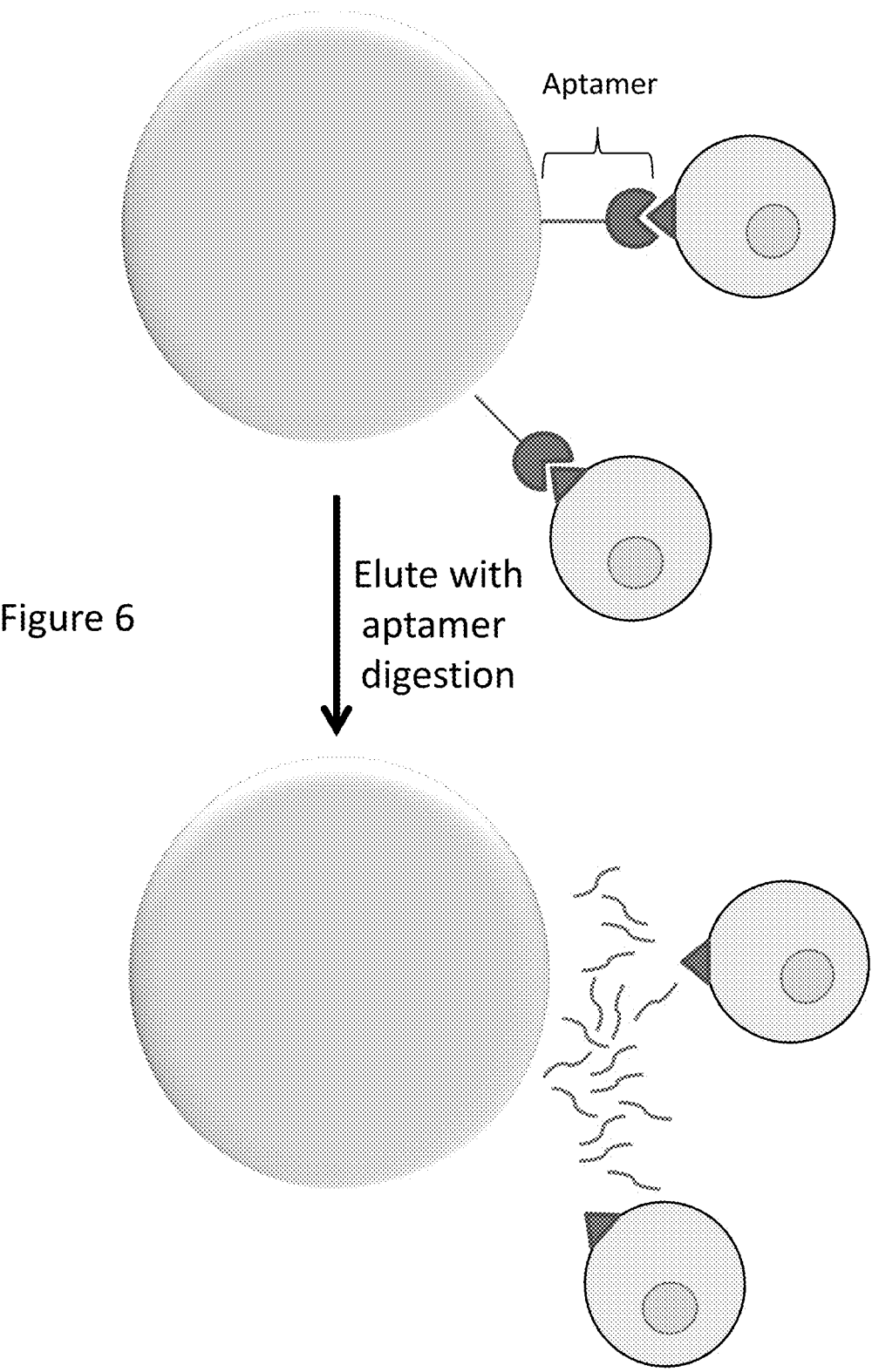
FIG. 6 depicts an aptamer capture and release strategy.

In certain embodiments, the capture entity can be directly bound to the resin. FIG. 5 depicts a bead comprised of an antibody. In FIG. 6, the bead is comprised of an aptamer capture entity. In these embodiments, the column can be packed with a solid phase comprised of a capture entity. Alternatively, the column can be packed and then a capture entity (e.g., an antibody, aptamer, etc.) can be passed through the column and bind the column medium.

Figure 4:
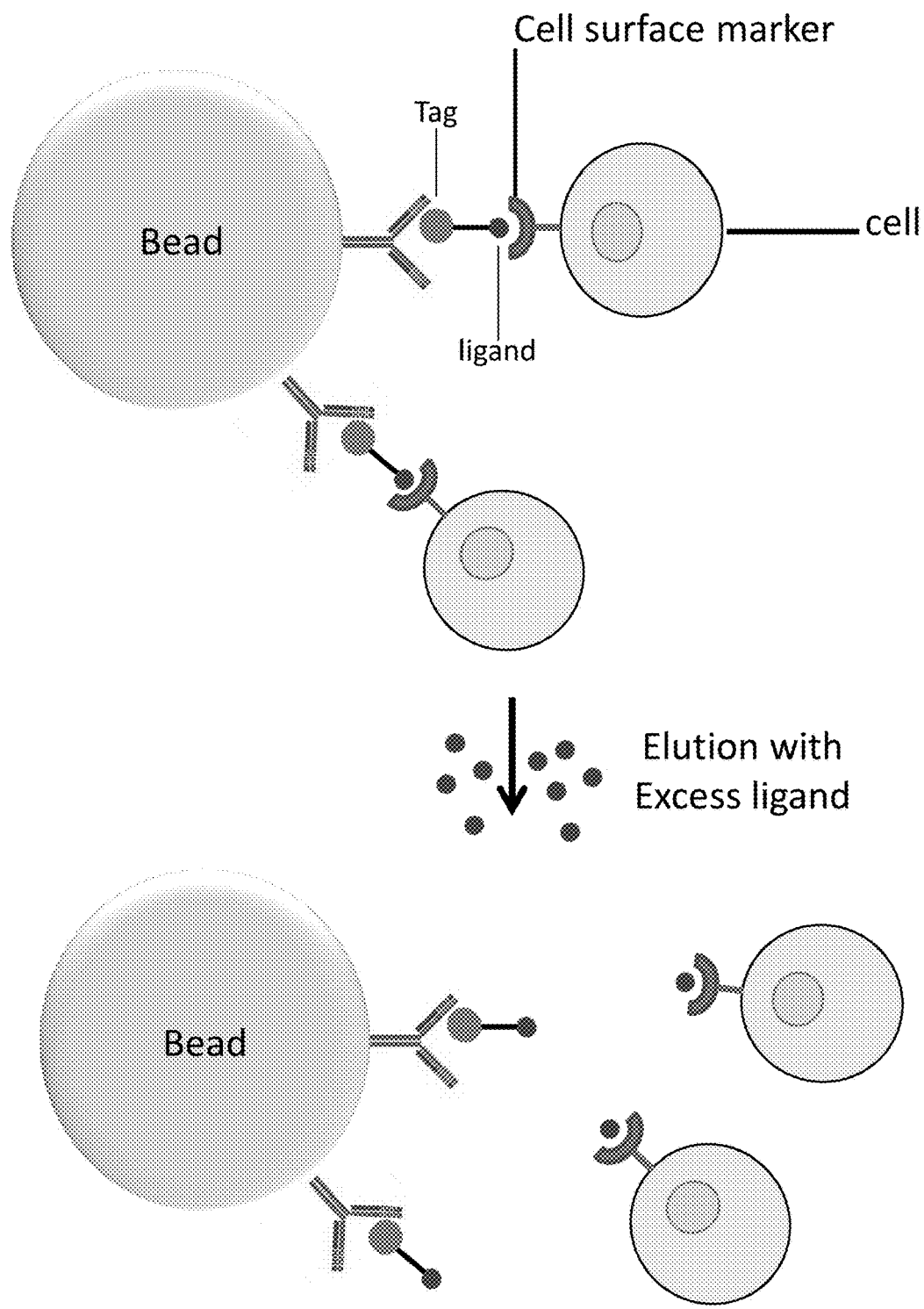
FIG. 4 is a depiction of an embodiment of a competition elution strategy.

In alternate embodiments, the capture entity can be associated with the solid phase via a linker as shown in FIG. 4. In FIG. 4, an antibody on the bead binds a tagged ligand, which in turn, binds a cell surface marker.

The linker can be any length and can be comprised any type of molecule(s). In one example, the capture entity can be a monoclonal antibody which can be associated with the column media via a secondary antibody raised in a different host species, such as goat anti-mouse. In fact, a series of antibodies (raised in a different host species) can be used in the linker.

Any type of linkage can be used to associate the column particles with the capture entity. That is, the capture entity can be covalently bound to the column particles or associated with the column particles using electrostatic interactions, hydrogen bonds, hydrophobic interactions, hydrophilic interactions or combinations of these.

In some embodiments, the linker contains a cleavage site that can be used to elute cells. Cellular surfaces are comprised of a number of components that can be used for cell capture including proteins, glycoproteins, carbohydrates and channels. Cell surface markers are integral membrane proteins that identify the cell as a particular type. A cluster of differentiation or CD is a surface molecule, or antigen on a cell's surface which can associate with the capture entity. Cell-surface receptors are cell surface, or integral proteins that bind to external ligand molecules. Many cell surface markers have been characterized and can be identified by PCR. These include human, murine and rat cell surface markers as well as other genera.

Cell surface markers, receptors and clusters of differentiation can all be used to capture the cells. Interaction between the cell and the capture entity can be by van der Waals forces, hydrophobic forces, hydrophilic forces, electrostatic forces, hydrogen bonds or covalent bonds.

Antibodies used as capture entities can bind cell surface markers. There are thousands of commercially-available antibodies that bind cells. Rituximab is an antibody specific to CD20 and can be used to treat diseases characterized by excessive B-cells including non-Hodgkin's lymphoma. Another antibody, Trastuzumab targets the epidermal growth factor receptor 2 protein. It can be used to treat HER2+ cancers such as breast cancer, stomach cancer and esophageal cancer.

The following is a non-limiting list of human cell surface markers that can be identified by PCR. Similar lists are available for mouse and rat cell surface markers.

CD4 can be by used to capture lymphocytes in immunosuppressed or HIV positive patients. Patients with low CD4 count are at greater risk of opportunistic infections.

Ki-67 is a marker of cell proliferation that and for example can assist diagnosis and guide therapy for Burkitt's lymphoma and other diseases.

S. sanguis OMZ9 and S. mutans serotype a are markers associated with streptococcal bacteria.

Certain stem cells have surface markers including glycolipid SSEA3/4, glycoprotein TRA-1-60 and glycoprotein TRA-1-81.

Activated B-cells: CD28, CD38, CD69, CD80, CD83, CD86, DPP4, FCER2, IL2RA, TNFRSF8, CD70 (TNFSF7).

Mature B-cell markers: CD19, CD22, CD24, CD37, CD40, CD72, CD74, CD79A, CD79B, CR2, IL1R2, ITGA2, ITGA3, MS4A1, ST6GAL1. Other B-cell surface markers: CD1C, CHST10, HLA-A, HLA-DRA, NT5E.

T-Cell Surface Markers:

Cytotoxic T-cells: CD8A, CD8B. Helper T-cells: CD4. Activated T-cells: ALCAM, CD2, CD38, CD40LG, CD69, CD83, CD96, CTLA4, DPP4, HLA-DRA, IL12RB1, IL2RA, ITGA1, TNFRSF4, TNFRSF8, CD70 (TNFSF7). Other T-cell surface markers: CD160, CD28, CD37, CD3D, CD3G, CD247, CD5, CD6, CD7, FAS, KLRB1, KLRD1, NT5E, ST6GAL1.

Natural killer (NK) cell surface markers: CD2, CD244, CD247, CD7, CD96, CHST10, IL12RB1, KLRB1, KLRC1, KLRD1, NCAM1.

Monocyte and macrophage cell surface markers: Activated macrophages: CD69, ENG, FCER2, IL2RA. Other monocyte and macrophage surface markers: C5AR1, CD163, CD40, CD63, CD74, CD86, CHST10, CSF1R, DPP4, FCGR1A, HLA-DRA, ICAM2, IL1R2, ITGA1, ITGA2, S100A8, TNFRSF8, CD70 (TNFSF7).

Endothelial cell surface markers: ENG, ICAM2, NOS3, PECAMI, SELP, TEK, VCAM1, VWF.

Smooth muscle cell surface markers: MYH10, MYH9, MYOCD.

Dendritic cell surface markers: CD1A, CD209, CD40, CD83, CD86, CR2, FCER2.

Mast cell surface markers: C5AR1, FCER1A, FCER2, TPSAB1.

Fibroblast (stromal) surface markers: ALCAM, COL1A1, COL1A2.

Epithelial cell surface markers: CD1D, KRT18, KRT5, KRT8, EPCAM.

In certain embodiments, cells can be captured using an aptamer specific to a cell surface marker. Aptamers can be single-stranded or double-stranded nucleic acid (RNA or DNA) oligonucleotides. Aptamer sequences can be determined using Systematic Evolution of Ligands by Exponential Enrichment (SELEX) or other selection processes (see for example Base Pair BioTechnologies, Inc., Houston, Tex.). The aptamers can contain non-standard or modified bases. As used herein, a "modified base" may include a relatively simple modification to a natural nucleic acid residue, which confers a change in the physical properties of the nucleic acid residue. Such modifications include, but are not limited to, modifications at the 5-position of pyrimidines, substitution with hydrophobic groups, e.g., benzyl, iso-butyl, indole, or napthylmethyl, or substitution with hydrophilic groups, e.g., quaternary amine or guanidinium, or more "neutral" groups, e.g., imidazole and the like. Additional modifications may be present in the ribose ring, e.g., 2'-position, such as 2'-amino (2'-NH$_2$) and 2'-fluoro (2'-F), or the phosphodiester backbone, e.g., phosphorothioates or methyl phosphonates.

Aptamers are useful capture entities that can be chemically conjugated to chromatographic beads. For example, Shen et al. used DNA aptamer-functionalized silicon nanowires to capture and release non-small cell lung cancer cells (Shen, et al. Advanced Materials, Volume 25, Issue 16, pages 2368-2373, Apr. 24, 2013).

Adhirons can also be used as capture entities. Adhirons are stable and versatile peptide display scaffolds to which entities can bind.

The capture entity and linker (if present) can be associated with, or bound to solid phase prior to loading the cell sample on the column. In some of these embodiments, the capture entity is cross-linked to the resin. If a linker is used, the capture entity and linker can also be cross-linked to the resin. In certain embodiments, the resin or solid support can be directly cross-linked to the cell.

One example of cross-linking involves the use of dimethyl pimelimidate (DMP), a cross-linking reagent. The cross-linking procedure can be performed as follows. Protein A or Protein G beads are washed with phosphate buffered saline (PBS). The beads may be in bulk or packed into the column. The antibody or Fab capture entity is added to the beads and bound. Excess capture entity is removed from the beads by washing. A stock solution of 13 mg/ml DMP, pH 8-9 is prepared. DMP is unstable in aqueous solution and is prepared immediately prior to use. Dissolve 1 ml of prepared 13 mg/ml stock of DMP with 1 ml wash buffer wash buffer 0.2 M triethanolamine in PBS. DMP solution is added solution to beads at a 1:1 ratio and reacted for 30 min at room temperature. The beads are then washed with 0.2 M triethanolamine in PBS. The crosslinking procedure can be repeated several times.

Crosslinking reagents generally contain two or more reactive groups that can react with functional groups such as amines, carbohydrate and sulfhydryls. The crosslinking may be chemical or photoreactive. Common crosslinkers contain maleimide or sulfhydryl reactive groups or succinimidyl esters (often referred to as NHS esters), all of which react with amines. Crosslinkers can have a variety of linker lengths and solubilities. Sulfosuccinimidyl esters allow for a more water-soluble crosslinker which can be useful when working with large biomolecules that are not amenable to using organic solvents. Crosslinkers with cleavable linkers such as disulfides are also available for conditions in which a permanent linkage is not desired.

Another amine-reactive strategy that can be used for immobilization involves the use of azlactone. A primary amine will react with an azlactone group in a ring-opening process that produces an amide. An option for immobilizing amine-containing affinity ligands is the use of carbonyl diimidazole (CDI). Coupling can be performed through sulfhydryl groups located on reagent groups or on cells. For example, sulfhydryls exists in the side chain of cysteine. Sulfhydryl groups typically are present in fewer numbers than primary amines. Iodoacetyl-activated supports react with sulfhydryl groups at physiologic to alkaline conditions (pH 7.2 to 9), resulting in stable thioether linkages. To limit free iodine generation, which has the potential to react with tyrosine, histidine and tryptophan residues, these reactions are usually performed in the dark. Pyridyl disulfide supports react with sulfhydryl groups over a broad pH range to form disulfide bonds. As such, conjugates prepared using this chemistry are cleavable with typical disulfide reducing agents, such as dithiothreitol (DTT). Carbonyl-reactive supports can couple carbonyl (sugar) groups. Glycoconjugates, such as glycoproteins or glycolipids, usually contain sugar residues that have hydroxyls on adjacent carbon atoms; these cis-diols can be oxidized with sodium periodate to create aldehydes as sites for covalent immobilization. Hydrazide-activated supports will conjugate with carbonyls of oxidized carbohydrates (sugars) at pH 5 to 7, resulting in formation of hydrazone bonds.

Carboxylic acids may be used to immobilize biological molecules or cells through the use of a carbodiimide-mediated reaction. Supports containing amines (or hydrazides) can be used to form amide bonds with carboxylates that have been activated with the water-soluble carbodiimide crosslinker EDC. Hydrazone bonds can be used immobilize glycoproteins. Aldehyde activated resins or supports can be used to bind amines or ketones on cells. Cyanogen bromide activated supports will react with primary amines on cells.

It is possible to add a capture entity to the column medium after the column is packed. If the capture entity is not bound to the column, it is possible to pass the capture entity through the column so that it becomes associated with the column resin. Next, a cell sample can be loaded.

In alternate embodiments, the capture entity can be mixed with the sample and incubated prior to the capture step. For example, a biotinylated aptamer may be mixed with a sample of T cells and then incubated until the aptamer is bound to the markers on the cell. Then, the aptamer-cell combination may be passed through the column. The aptamer binds the resin and the cells are captured. In this scenario, a linker may also be present. When present, the linker can be bound to the aptamer or bound to the resin. Following cell capture, the column is washed and the cells are eluted by disrupting the aptamer structure physically, chemically or enzymatically e.g. using salt, pH, chelation, temperature (heat or cold), etc.

In another method, the capture entity (with or without a linker) can be mixed with the cells and then passed through the column immediately (or almost immediately) without incubation. For example, a tagged antibody or Fab is mixed with cells and then the mixture is passed through the column without incubation. This process is called flowing-incubation capture. In this example, association and capture of the cells and linker occurs during the same process, flowing of the sample-capture entity mixture through the column. The capture process is performed with a flowing stream. Cells can bind the tagged antibodies or Fabs and then the combination is captured by the column media.

In some embodiments, the capture entity and the cell can be loaded onto the beads simultaneously. For example, a capture entity such as an antibody, Fab or aptamer that is specific for a marker on the cell surface can be added to the sample directly before the column loading process takes place. The capture entity may be tagged to facilitate capture by the column medium. In these embodiments, the capture entity may associate with the column medium either before or after association with the cell.

In some embodiments, capture can be performed with a low affinity functional group using additive effects or hysteresis effects. For example, the capture entity may have a low affinity for any one particular cell marker. But the capture effect can be additive in a several-step process. Multiple capture points of weak capture can be strong enough overall to capture the cell.

Multiple points on the cell surface can interact with the column solid phase. The association between the capture entity and a single point on the cell surface may not be enough to capture the cell, but may lead to a second point of capture interaction, which leads to another point a capture interaction and so on. This multipoint interaction can be called a hysteresis effect or additive effect. When one capture event leads to another event and then another, etc., the cumulative capture points can result in the firm capture of the cell.

The capture equilibrium can be shifted by adjusting a number of parameters. For example, if the sample is dilute, capture might be faster and/or more complete if the sample contains a small number of target cells or the matrix contains a large number of capture entities or if a larger column bed is used.

In some embodiments, the number of cells or cell concentration in the sample is low. For example, a blood sample may contain a small number or low concentration of cancer cells. In some embodiments, it is desirable to capture and concentrate these cells for study and/or quantification. In order to be most useful, the capture of these cells must be predictable and consistent. This does not necessarily mean that every desired cell in a particular sample is captured. But it does mean that if all of the cells are not captured, the percentage of cells captured is reproducible and the standard deviation of capture is low.

For the columns and methods of the invention, the coefficient of variation of the number of cells captured from identical samples is less than 25%, 20%, 15%, 10% or less than 5%. The coefficient of variation is low because cells are not trapped in the column matrix, even when the sample is passed through the column repeatedly using back and forth flow. Repeated passes through the column increase the chances of damaging or killing cells. So intuitively, it is desirable to limit repeated back and forth flow. However, repeating the contact of cells with the column will bring capture to an equilibrium based on the selectivity of the cell for the column. Because cells can be passed through the column multiple times without physical trapping, it is possible to obtain reproducible results.

Cell surface marker density can be exploited to preferentially capture a particular type of cell. For example, cancer cells may exhibit identical markers as normal cells, but at a higher density. Capture entities may take advantage of closer and proper spacing of the cancer cell surface markers to preferentially capture this cell type. One way to accomplish this is to use a resin with multiple capture entities, the spacing of which matches the spacing of cell surface markers on the desired cell type. This higher density/proper spacing of the capture entities may allow the additional contact points during cell capture. That is, the additive effect of additional capture points will result in the successful capture of the desired cells.

This strategy of increasing the capture entity density is especially effective with capture sites that have a weaker affinity for the targeted cell surface marker. Capture is preferential for the cancer cells having a higher density of surface markers because normal cells that possess fewer surface markers are not captured or if they are captured, they do not remain bound due to their weak affinity for the capture entity. Selectivity can be further increased by employing a high stringency wash step.

This approach can be used when the targeted surface marker density of the desired cells (e.g. the cancer cells) is greater than the surface marker density of the comparable (normal) cells. For example, the cell surface marker density can be 20% higher, 40% higher, 60% higher, 80% higher, 100% higher, 150% higher, 200% higher, 300% higher 400% higher or even greater.

Cell capture may be based on correct orientation and/or spacing of molecules. For example, a borate molecule positioned on a resin can capture two cis hydroxyl groups from a carbohydrate positioned on the cell. A carbohydrate molecule with a trans hydroxyl groups does not have the proper positioning for capture by the borate capture entity.

Cells that are undergoing cell signaling may express new markers. Capture entities specific to these new cell surface markers may be utilized to capture such cells.

In some embodiments, several cell surface markers can be exploited. That is, different cell surface markers may have different uses or functions in the methods of the invention. For example, a cell may be captured using one marker and then tagged using another marker. A third marker (or combination of markers) may be interrogated, measured or studied.

Following the capture step, a tag may be introduced into the column to label the cells and in some cases, give a detectable signal to the cell. In these cases, a suitable marker on the cell may be targeted to react with the cell to make the cell detectable. A label or tag may be introduced before or after column washing.

Elution

After cell capture and column washing, the cells may be eluted without removal of the capture entity. Elution of the cells from the column can be accomplished using a variety of strategies. One elution strategy involves competition. Cells can be captured with a ligand that binds a cell surface marker and then eluted with either the same ligand or another entity that binds the same cell surface marker. For example, cells bound to antibodies and captured on ProA resin can be eluted with an antibody (e.g. in excess), ProA or a similar molecule. Other strategies involve temperature, pH or eluents such as low pH solutions, citric acid, glycine buffer or others. After elution, the buffer may be adjusted to a neutral pH, more compatible with the cells.

Another competition strategy utilizes ANTI-FLAG resin. A FLAG-labeled entity, aptamer, antibody fragment, Fab or antibody that binds a cell surface marker can be engineered e.g., in E. coli. The FLAG-labeled Fab or antibody can be coupled to the column resin and cells can be eluted with excess FLAG peptide as shown in FIG. 5.

Many other functional groups can be used for competitive, equilibrium type reactions to capture, elute and recover cells. Hydroxyl or hydronium ions could compete with cells for binding a capture entity comprised of acid or base groups. Other buffer ions that displace complexing ligands may be used in a competitive manner. Imidazole usually can be used to displace His-tagged binding proteins or molecules.

Alternatively, cells can be eluted by a physical change such as a change in pH or temperature as shown in FIG. 6. Preferably, an eluent can be selected that does not harm the cells, particularly when the recovery of viable cells is desired. In one example, a temperature-sensitive ProA resin can be used such as Byzen Pro resin made by Nomadic Bio Science. Using this type of resin, cells can be eluted at neutral pH by increasing the temperature as shown in FIG. 6. In a second example, cells can be captured by antibodies specific to cell surface markers and eluted using a low-pH eluent. In this example, the elution step could be performed rapidly followed by a quick transfer of the purified cells to a neutral-pH solution.

In some embodiments, cells captured on a column can be eluted using enzymatic cleavage. For example, cells can be captured using ProA resin charged with antibodies that bind a cell surface marker. The antibody could then be cleaved with an enzyme (e.g. papain or pepsin) to elute the cells. Other methods include using a chelating agent, salts, pH, small molecules, urea or other denaturing chemicals, organic solvents, cold or heat. In certain embodiments, cells are eluted at temperatures 30-40 degrees C. or higher.

Calmodulin (an abbreviation for calcium-modulated protein) is a multifunctional intermediate calcium-binding messenger protein expressed in all eukaryotic cells. A calmodulin-functionalized resin can be used to capture cells. EGTA, EDTA and other chelators can be used to complex calcium and elute the cell.

In certain embodiments, cells recovered from the column are still associated with the capture entity, the capture entity plus the linker or the capture entity plus a partial linker. That is, these entities can remain complexed with the cells during the elution step. In these embodiments, cells can be eluted from the column using conditions that offer the fastest and most efficient elution process that maintains the health and viability of the cells. Examples of associated capture entities include antibodies, antibody fragments including Fabs, tagged Fab linker molecules, biotin, streptavidin HIS or FLAG-tagged linker molecules containing antibodies or aptamers. For the purpose of this discussion, these materials can be called the eluted capture entities. The solution or suspension of the recovered cells contains these eluted capture entities along with the cells.

In some cases, cells eluted with an associated entity can be diluted to dissociate the entity. That is, the binding or association of the eluted entity can be reversed by dilution. Depending on the strength of the association between the entity and the cell, dilution by a factor of 2 can reduce or reverse the entity-cell interaction by as much as a factor of 2. Similarly, a dilution by a factor of 10 can reduce the interaction by up to a factor of 10. Eluted cells having an entity bound can be diluted by a factor in the range of 2 to 1000-fold. For example, the eluted cells having a bound entity can be diluted 2, 3, 4, 5, 10, 20, 50, or 100-fold or more.

In certain embodiments, the eluted entity can be removed from the eluted cell solution by employing a recapture step of the eluted capture entity but leave the cells in place. In this case, the solution/suspension of the recovered cells is passed through a second column that is selective for the capture entity but not the cells. For example, an eluted capture entity that includes a biotin or similar tag (such as a biotin analog) can be captured with a streptavidin column while the cells pass through the column. Of course, the column must be constructed with unconstrained flow paths so that cells are not trapped or damaged. Only the eluted capture entity is captured. Other examples for removal of the eluted capture entity include capture of HIS-tagged molecules, tagged aptamer molecules, and antibodies or fragments of antibodies, etc.

In some embodiments, the capture entity bound to the column media is not eluted from the column with the cells. In these embodiments, the cell can be dissociated from the capture entity without disturbing the bond or linkage between the capture entity and the column medium. One strategy to avoid elution of the capture entity involves chemically binding the capture entity to the resin. For example, the capture entity can be cross-linked or covalently bound to the resin. In these circumstances, stronger elution conditions can be used to remove cells without removing the cell capture entity. An example of this is the use of dimethyl pimelimidate (DMP) crosslinking of a capture antibody to the beads. An aptamer tag may be chemically bound or attached with a highly selective tag to the media to prevent removal. Another example involves capturing an antibody with Protein A/G agarose resin and covalently immobilizing the antibody to the support by crosslinking is with disuccinmidyl suberate (DSS). In another example, a capture entity comprised of a metal may help an aptamer or protein to form the correct shape for capturing protein. Removal of the metal by a chelator disrupts the shape of the capture entity and therefore removes the ability of the aptamer or protein to retain the cell. The elution may be performed by changing the pH or adding a competitive reagent that will compete for the capture entity but does not interaction with the cells. A chelating reagent or other reagent may be added to the elution solvent to change or deform the capture entity structure and release the cells. Of course, other chemistries can be employed.

The capture entity or linker may contain a cleavage site. The cleavage may be performed by any means including physical, chemical, enzymatic or photochemical. The capture entity can be engineered to cleave a nucleic acid or protein sequence at a specified location causing elution of the cells. For example, Proteins, nucleic acids and organic molecules can be cleaved with enzymes, acids or bases.

Following elution, it may be desirable to determine the proportion of cells that remained viable. One means for determining cell viability is the use of a dye that enter living cells. A nonlimiting list of these dyes includes safranin, Eosin, propidium, Congo red, erythrocin, Trypan blue, nigrosine, and Alcian blue.

Enrichment

In some embodiments, cell capture of the targeted cells may not be desired. In these embodiments, an enrichment step okay you have an issue that is can be performed in which the desired cells pass through the column while other non-desired materials are retained. Enrichment can be used to separate the desired cell type from other cells or from contaminants. In either case, the desired cell type passes through the column while other entities are captured. Cells of interest flow through the column of the invention and are unhindered and undamaged.

A variety of columns can be used for enrichment. Enrichment can be performed by size exclusion, affinity, ion exchange or other chemistries. Regardless of the column type, the targeted or desired cells pass through while the undesired cells or other materials are retained. Enrichment columns can be operated using unidirectional or bidirectional flow.

Cells processed with an enrichment column include any cells described above in the sample section. For instance, the sample can be comprised of cells in a particular metabolic state, viable cells, dead cells engineered cells or naturally occurring cells. Following the enrichment step, cells of interest may be recovered for any type of downstream processing e.g. tagged and studied. In certain embodiments, the cells of interest are alive and viable. In some embodiments, cells of interest are untouched, unactivated or uninduced.

For example, gel filtration (size-exclusion chromatography be used to enrich a particular cell type by separating cells away from non-cell components or by separating cells from each other based on their size. For example, circulating tumor cells (CTCs) are larger than other cell types and can be isolated using size exclusion chromatography. Gel filtration can also be used to clean up a sample. For example, non-cell material can be taken up by the column and thereby removed from a diagnostic sample. In some embodiments, gel filtration can be used for buffer exchange. In other embodiments, buffer exchange can be accomplished using dialysis.

Genetic engineering can be used to change the surface of the cells. Cells that have been engineered using techniques such as CRISPR (or other tools) may express new cell surface markers. In this case the un-engineered cells can be separated from the engineered cells. For example, CRISPR cells may be captured and recovered while un-engineered cells pass through the column.

In other cases, cells can be engineered to eliminate the expression of a surface marker while the un-engineered cells continue to express the marker. An enrichment process could be used to capture a marker on the unmodified cells while the engineered cells pass through the column. Conversely, a capture, wash and release process could be used to capture and recover CRISPR-engineered cells.

Dead or dying cells including cells that are undergoing or have undergone apoptosis can exhibit specific surface markers. For example, Annexin V protein will bind to membrane phospholipid phosphatidylserine in the presence of calcium (II). Phospholipid phosphatidylserine is exposed at the cell surface during the early stages of apoptosis and this marker can be used to remove dead or dying cells while leaving the living cells in solution. In this example, cells undergoing apoptosis could be captured by the column while the living or viable cells pass through.

In some embodiments, two or more columns can be used in series to remove different undesired materials. In some embodiments, an enrichment column is operated as an additional processing step after the use of a cell capture and elution column. In these embodiments, the solution containing the recovered cells may contain additional undesired molecules, groups or entities. These undesired entities can be generated during elution. Depending on the elution process, these undesired entities can include the capture entity and the linker, the capture entity and a partial linker, the capture entity or a partial capture entity. The capture entity can be any capture entity described above including HIS-tagged molecules, tagged aptamer molecules, and antibodies or fragments of antibodies, etc.

Alternatively, enrichment can be used for buffer exchange or to remove elution components such as ions, enzymes, proteins, biological or inorganic molecules, or portions of these molecules. Of course, enrichment columns are constructed with unconstrained flow paths so that cells are not trapped or damaged as they travel through the column.

Adherent Cell Manipulation, Study and Recovery Using Packed Bed Columns

Many cell types need to adhere to a surface or another layer of cells in order to grow and survive. These cells are called adherent. In some embodiments of the invention, cells adhere to the surface or pore of a solid support such as a cell support or microcarrier while they grow and divide. In these embodiments, adherent cells can include viruses. The term "cell support" as used herein represents a support matrix that allows growth of adherent cells or anchorage-dependent cells.

Cell supports can have diameters in the range 10 to 1000 µm. Cell support diameters can be in the range of 20 µm to 500 µm, 30 µm to 400 µm, 50 µm to 350 µm 75 µm to 350 µm, 90 µm to 350 µm, 125 µm to 250 µm, 125 µm to 250 µm, 150 µm to 200 µm, 175 µm to 200 µm, 180 µm to 200 µm or 175 µm to 180 µm. They are generally spherical but may also have an irregular shape. Cell supports can be made from a number of different non-toxic materials that possess the appropriate surface properties that allow cells to adhere and proliferate. Nonlimiting examples include DEAE-dextran, glass, metal (such as stainless steel or titanium), cellulose, dextran, polystyrene, polyethylene, polycarbonate, PVC, Teflon, silica, silicone rubber, polyester, polypropylene, gelatin, glycosaminoglycans, plastic, acrylamide, collagen, Cytodex, alginate and combinations of these. These cell supports along with different surface chemistries, can influence cells in a number of ways including their morphology and proliferation. Surface chemistries can include proteins such as extracellular matrix proteins and recombinant proteins, peptides and a variety of positively or negatively charged molecules. Cell support material can be formed into different shapes including spherical, flat disks, woven discs, fibers, cubes as well as other shapes.

The cell-bead complex can be suspended in a medium allowing adherent cell lines to grow. After cell growth, the beads/particles can be recovered and packed into a column. Such systems can be used for research and development including testing or development of drugs, vaccines, diagnostics, enzymes, hormones and antibodies.

In some embodiments, cell support beads contain a core material and a surface coating chemistry that facilitates cell attachment. The bead material, along with different surface chemistries, can influence cellular behavior, including morphology and proliferation. Surface chemistries can include cellulose, dextran, extracellular matrix proteins, recombinant proteins, attachment proteins, (e.g. fibronectin or variants of the cell recognition site of fibronectin), polypeptides, peptides, positively or negatively charged molecules. For example, Sephadex beads may be coated with collagen.

The culture medium must effectively support cell growth. Important components include sources of carbon and energy (e.g. fructose, pyruvate, glucose or galactose), divalent cations, nucleic acid precursors (adenosine, guanosine, cytidine, uridine, thymidine), retinoids, choline, ascorbic acid, polymers (Ficoll, Pluronic, Dextran, methylcellulose) serum (e.g. fetal calf serum, horse serum, human serum, mouse serum), amino acids, nucleic acids, folic acid and proteins. In addition, the cell culture should utilize medical grade gases (e.g. $CO_2$) of the highest possible quality and the culture should be free of carbon monoxide, nitrous oxide and hydrocarbons. In certain embodiments, a $CO_2$ mixer can be coupled to the incoming air that supplies carbon dioxide and oxygen to the culture. The pH at 37° C. can be in the range of 6.8 to 8.0 is often in the range of 7.2 to 7.4.

Several types of beads or particles may be used to grow the adherent cells. These include alginate-based (GEM, Global Cell Solutions), dextran-based (Cytodex, GE Healthcare), collagen-based (Cultispher, Percell), polystyrene-based (SoloHill Engineering) beads or particles and combinations of these. They differ in their porosity, specific gravity and surface chemistries.

Different types of Cytodex are available to support the growth of anchorage-dependent animal cells for use in a multitude of applications. In Cytodex 1, ionic charges are distributed throughout the matrix. Cytodex 1 is a general-purpose bead formed by substituting a cross-linked dextran matrix with positively charged DEAE groups distributed throughout the matrix. It is suitable for most established cell lines and for production of viruses or cell products from cultures of primary cells and normal diploid cell strains. In Cytodex 3, a collagen layer is coupled to the surface of the bead. Cytodex 3 is made by chemically coupling a thin layer of denatured collagen to a cross-linked dextran matrix. It is used for cells that may be difficult to culture in vitro and for cells with an epithelial-like morphology. Cytopore is composed of cross-linked cellulose (cotton linter) and have a porosity up to 90%.

Adherent cells can be introduced to a column in at least two ways. The resulting columns can be called adhesion columns. In one method, cells are grown on cell supports and then packed into columns. Adherent cells can be inoculated into a suspension of beads and grown on their surface. Gentle stirring allows the beads to remain in suspension while the correct conditions (e.g. temperature, oxygen, buffer conditions, etc.) are maintained for cell growth and viability on the bead surface.

Column packing can be performed without harming the cells for example, by gravity or gentle pumping of the cell/cell support complex into the column. Alternatively, the cell/cell support complex may be drawn up into a pipette and deposited into the column. After the column is packed, the cells can be used variety of methods described herein.

Another method of preparing adhesion columns of the invention is to first provide a column packed with the appropriate material. Cells can be introduced into the columns by pumping a cell suspension through the column bed.

Adherent cells can attach to cell supports, beads or particles such as Cytodex naturally. However, it is also possible to attach cells via the capture entities and mechanisms described herein (e.g. see the section above on capture). Adherent cells can be attached to cell supports by a linking process using a variety of means and molecules including physical attachment, the use of proteins, linking molecules, proteins, nucleic acids, carbohydrates, antibodies, polypeptides, aptamers, adhirons, combinations of these or other (organic) molecules and processes.

After use of the columns, the adherent cells can be recovered from the column. In some media, a collagen layer covers the surface of the microcarrier beads used to capture or grow cells. Because the collagen surface layer can be digested by a variety of proteolytic enzymes, it is possible treat the beads with an enzyme to elute and recover the cells. Examples of proteolytic enzymes include trypsin and collagenase. For example, a Cytopore surface can be dissolved with a cellulose enzyme to release the cells.

In another example, dextranase can be used to digest the microcarrier bead or particle so that cells are released and recovered. Other procedures for elution of the cells include the use of chelating agents, enzymes, exposure to hypotonic conditions, changing the pH, changing the temperature (e.g. cold conditions), the use of sonication, and alteration of the surface tension of the culture medium.

In some embodiments, the cells can be released from the beads while they are in the column bed. In other embodiments, the beads are first removed from the column and then the cells are released and recovered. Examples of processes for cell release include hypotonic treatment, cold treatment, sonication and lignocaine. In some embodiments, the microcarrier is degradable as described above.

Untouched Cells

Untouched cells are defined herein as cells that have not been bound or handled. That is, cell surface markers have not been bound by an antibody or any other type of capture entity. Conversely, touched cells have been bound or captured using a capture entity. Cells that are touched are also referred to herein as activated cells.

For many applications, untouched cells are desirable because binding a cell surface receptor can induce a signal transduction cascade, resulting in the alteration of a cell's anatomy and/or physiology. For example, when a transmembrane cell surface receptor binds a ligand, a conformational change can occur which can in turn, start a signal transduction cascade resulting in gene activation. This conformational change occurs on the intracellular side of the cell surface receptor protein. Once the gene is activated, an mRNA is transcribed and transported from the nucleus to the cytoplasm a ribosome will translate it into protein.

Cells that do not bind a capture entity are untouched; the signal transduction pathway does not occur. The isolation of untouched cells is desirable for studying cells because no artificial, unwanted activation of the cells has occurred. Untouched cells, while desirable, can only truly be obtained using enrichment strategies. The disadvantage to enrichment is that the desired cells are simply enriched; they may not be completely purified away from other cell types or contaminants. After an enrichment step, the sample may still contain additional cell types or other contaminants.

Cells captured by association with a capture entity are said to be touched. For some applications, touched cells are acceptable. In some embodiments, the capture entity is selected for efficient cell capture but it does not alter the cells in a way that is important or relevant to their final use. For example, cells may be touched but not induced; their biological state is unchanged as described below.

Unactivated or Uninduced Cells

In some methods of the invention, it is desirable to isolate cells without changing their physical or metabolic state. When cells are captured via a surface marker, it is preferable that this binding event is not trigger a signal transduction cascade. For the purposes of this discussion, cells that are physiologically and metabolically unchanged following capture and elution will be referred to herein as unactivated or uninduced cells. In certain embodiments of the invention, unactivated/uninduced cells are captured and eluted from a column.

In some embodiments of the invention, it is possible to capture cells and elute them in an uninduced or native state. Any of the capture and elution methods described above can be employed to produce uninduced cells. However, the cell surface marker and capture entity should be selected carefully. Care must be taken to choose a marker that does not activate the marker it binds.

In some cases, it may be necessary to perform gene expression studies to verify that expression is unchanged following cell capture and elution. Other analyses can aid in this verification process such as determining whether cell morphology has changed, performing proteins assays, viability assays and other cell-based assays to examine cell function.

After it has been determined that gene expression is not affected by cell capture, the cell surface marker has been verified and can be used for purification of unactivated cells.

Removal of the Solid Chromatography Medium from the Column

In some embodiments, the resin with cells attached can be removed from the column after the capture and wash steps. In these embodiments, the resin (with cells attached) can be placed in a well. Cell lysis can be performed if desired. PCR can be performed either on whole cells or lysed cells. Nucleic acids can be isolated and analyzed e.g., by sequencing.

Removal of the resin can be performed by piercing the bottom frit of the column and then pushing the resin into a well with air or liquid. A frit piercing tool can be used for this purpose. In some embodiments, the frit piercing tool is comprised of a handle and a piercing point however, a wide variety of geometries are possible. The tool can be used manually by grasping the handle and pushing the piercing point of the tool through the column frit and into the bed. Then the tool is removed and the column is placed above a tube or microplate well which will receive the resin. Air or liquid can be used to push the resin into the well.

In another embodiment, the frit piercing tool can be recessed in a well, handle side down into the well of a microplate. The column is positioned above the well and pushed down into the well to pierce the frit. The piercing tool can be removed or remain in the well. Air or liquid can be used to push the resin into the well. These embodiments can be performed in automated parallel fashion.

On-Column Manipulation, Lysis or Interrogation

After capture, the cells can be examined, manipulated or interrogated on the column. In certain embodiments, the cells can be tagged with an entity or labeled on column. On-column labeling can enhance signal-to-noise ratio which can be useful for diagnostic and other applications. The signal-to-noise ratio can be enhanced by using concentrated labeling reagents, favorable buffer conditions and long reaction times thereby driving the tagging reaction to completion or at least shifting the equilibrium to a higher reaction completion. In addition, the background signal is reduced by washing which removes unreacted label.

Tags and labels are described herein and include any entity capable of binding a cell directly or indirectly. A nonlimiting list of tags/labels includes fluorescent tags, biotin or biotin analogues, avidin, streptavidin, HIS tags, TAP tags, FLAG tags, dyes, radioactive entities, proteins, enzymes, metals, small molecules, polypeptides, carbohydrates, antibodies, aptamers, adhirons and combinations of these.

Ex vivo experiments can be performed on captured cells on the column. That is, the column conditions can be controlled to mimic conditions found in an organ, tissue or biological fluid. Ex vivo conditions can also be used for the capture and elution steps.

In some embodiments, cells can be lysed on column and cell components can be analyzed. In these embodiments, cellular contents can be eluted or washed from the column or analyzed on the column. On-column lysis can be performed slowly and with large volumes of dilute lysis solution to prevent the column from plugging. On-column lysis can be performed in 10 seconds, 30 seconds, 1 minute, 2 minutes, 5 minutes, 10 minutes or more. Lysis can be performed using at least 1 column volume of lysis solution. In some embodiments, 2 column volumes, 3 column volumes, 4 column volumes, 5 column volumes, 6 column volumes, 7 column volumes, 8 column volumes, 9 column volumes, 10 column volumes or even more lysis solution can be used.

In certain embodiments, live versus dead cells can be distinguished and visualized column. Reagents sold by Life Technologies and other companies can be useful for these methods.

In some applications it may be desirable to kill the immobilized cells or a subset of the immobilized cells. Sensitivity to antibiotics and minimal antibiotic inhibitory concentration can be evaluated on column. For example, cells can be selectively killed on the column as described below in example 27. In this example, bacterial cells are captured with an ion exchange medium and a subset of the captured cells are killed as a result of their antibiotic sensitivity. As a control, cells not treated with ampicillin remained viable.

Single-celled organisms can also undergo differentiation. For example, *Bacillus* species can form spores in response to adverse conditions. Spores can be captured on the column and germination conditions can be investigated by exposing the spores to different environmental and nutritional conditions.

Eukaryotic cells have a number of checkpoints in the cell cycle. At these checkpoints, the cell determines whether or not to move forward with division. The cycle can be halted until conditions are favorable (e.g. the DNA is repaired). Factors that influence the determination can include size, nutrients, molecular signals, DNA integrity, environment and others. After capture, it may be desirable to arrest or synchronize the cell cycle. Cell cycle arrest or synchronization can be accomplished by a number of means including nutrient limitation, serum starvation, cyclins, cyclin dependent kinases, colcemid, colchicne, paclitaxel, vincristine and vinblastine, CDK1, RO-3306 (Roche), 2[[3-(2,3-diclorophenoxy)propl]amino]ethanol (2,3-DCPE), thymidine, drugs, viruses and environmental conditions.

In one example, a known number of cells may be attached or captured by the column. Conditions in which the cells are maintained in a viable, non-replicating/dividing state can be established and the cells can be interrogated with increasing concentrations of one or more drugs, molecules or other entities. The cells can be evaluated on column or eluted and tested for any impact on viability. Following administration of the drug or other compound or material, and a fixed time of exposure, cells can be washed free of the drug or material while still bound and arrested, and the impact on cell viability examined. In some embodiments, the cells can be eluted prior to evaluation.

In another example, an anti-cancer drug can be introduced into mammalian cells using a retroviral vector. After introduction of the drug, the resulting mammalian cells can be studied at the cellular and molecular level. These cells can be compared to cells that did not get the drug.

In a third example, cells captured on a column can differentiate. In some embodiments, captured cells can be induced to differentiate. The differentiation process can cause alternative cell surface markers to be expressed. If a subset of captured cells differentiates, these differentiated cells can be captured on a second column using their newly-expressed cell surface markers.

Devices and methods for on-column manipulation and interrogation are further described below in the section below entitled, "Cell-based stationary phase for liquid chromatography".

Cell Therapy

The invention additionally includes devices and methods for treating diseases. In some embodiments, healthy cells can be transferred between organisms. For example, donor cells from a healthy pancreas can be isolated on a column and transplanted into a patient suffering from Type 1 Diabetes. Stem cells are used for bone marrow transplantation will likely have a variety of therapeutic applications in the future.

Stem cells and other cells may be captured, purified with packed bed column technology in an open system or a sealed system and then manipulated using CRISPR type genome editing methodologies and technologies. The cells may be collected for further downstream processing.

CRISPR technology uses the cas9 enzyme with a guide RNA sequence to cleave and edit the genome at specific site while in the cell. This technology allows the researcher to specifically cut and insert/edit the genes at will. One of the major applications for this is gene therapy. Potentially, diseases caused by a single gene mutation can be cured using CRISPR to fix the gene. Another application is the manipulation of stem cells or early stage cells. Defective genes may be edited to control or eliminate disease or other genetic factors.

There are many research applications. Knock out organisms (knock out mice) can be created to facilitate researching genetic pathways. Similar knock out work can be performed with cell lines to create for example cell lines that function to perform specific things.

You can create different strains of plants can be created by changing/editing the genes to create resistant strains, more fertile strains or strains with specific attributes.

Editing of the cells with CRISPR technology may be performed while the cells are captured on columns of the invention or after they have been eluted and recovered from a column of the invention.

Samples containing donor cells can be obtained from a variety of sources including human, animal and cell culture. For example, donor cells can be obtained from cell culture, body fluids such as blood or lymph, organ tissue, bone marrow, etc. Donor cells can be engineered cells.

In other embodiments, cells are used to deliver gene therapies. Genes can be introduced into cells for example, by using a replication-defective adenovirus to produce engineered cells. These cells can perform a variety of therapeutic tasks such as delivering drugs, destroying cancer or regulating the immune system.

In one study, T cells were engineered to produce antibodies that bind cancerous cells (Grupp et al., N Engl J Med. 2013 Apr. 18; 368(16):1509-18). These engineered T cells were introduced into patients with leukemia to achieve remission or tumor size reduction. In this type of application, patients' T cells could be isolated using a column of the invention, engineered and then proliferated in cell culture. After the engineered T cells were grown, they could be isolated with a sterile column prior to introduction into a patient.

Therapeutics can be engineered using other cell types. Cancer-detecting sensors have been built using HEK-293T cells, a common cell line derived from human embryonic kidney cells and human mesenchymal stem cells. When these cancer-detecting cells encounter a cancer cell, a drug-activating enzyme is released, transforming a prodrug into a drug and killing the cancer cells.

The columns and methods of the invention can be used to isolate cells used for cell-based therapy. In these embodiments, sterile columns can be used for cell isolation. One advantage to this approach is that the cell populations obtained will be free of contaminants. In certain embodiments, cells isolated from columns are administered to patients to treat diseases such as cancer, diabetes, heart disease, Parkinson's, Alzheimer's, liver disease and others. Healthy cells can be used to replace cells in damaged or diseased organs. Cells isolated from any source can also be transferred to a different individual or organism. For instance, cells can be transferred to a mouse or other animal model for research, diagnostic, characterization or medical purposes.

Organ Cells on a Column.

Cells isolated from any source can also be transferred to a different individual or organism and contained on a column. Cells contained in columns and the products from columns may be used for research and medical purposes. They may be interrogated chromatographically to determine what interacts with the cells and the manner in which they interact. These experiments may be performed in parallel or serially. The effects on the cells may be studied. The biological products released from the cells may be used for research and medical purposes.

Columns containing captured cells of specific organs can be used for drug testing. For example, a column containing liver cells can be used to study the interactions and the effects these interactions of drug candidates with liver cells infected with hepatitis B, a viral infection of the liver.

Columns of the invention can capture kidney cells, intestine cells, muscle, cells, fat cells, bone cells, skin cells, pancreas cells, blood vein cells, etc. Furthermore, columns containing different organ cells can be studied together. For example, a drug candidate designed to interact with prostate cells might also interact with liver cells in such a way that might produce toxic products. The flow from columns may be collected and analyzed with mass spectrometry, infrared spectrometry, UV spectrometry or other analytical tools. Columns of the invention containing for example, parotid gland cells of the mouth or Eccrine sweat gland cells of the skin can be used to measure the interaction of several molecules. These molecules can be contacted with columns of the invention containing other cells such as liver cells, or kidney cells for example and the interactions and effect of interactions measured. The fluid that is pumped through the column or columns of the invention can be blood-mimicking fluids which bring sustenance to the cells.

Columns of the invention may be used to capture human induced pluripotent stem cells, adult stem cells that are treated to become embryonic state and then encouraged to become many different types of tissue. The use of stem cells on columns of the invention can be used to represent an individual. In this way, columns representing various organs could be derived from a single person. Or cells obtained from a biopsy from an individual can be captured onto columns of the invention. Experiments could then be carried out on the various columns to determine the interactions and effect of interaction of drugs at various concentrations or amounts (dosages), or combinations of drugs at various ratios, concentrations or amounts.

Therapeutics Screening

Columns and methods of the invention can be used to screen drug leads and identify drug targets. Disease cells can be immobilized on the column medium and challenged with pools of drug candidates such as small molecules, engineered proteins (such as engineered T-cell receptors), biologics or other entities. The column can be washed to remove species not tightly bound.

Multiple columns can be interrogated in parallel for example, with different drugs. These methods can be automated.

At this stage, the cells bound to drug candidates can be interrogated. Different solvent conditions can be applied to the column to test binding and dissociation conditions. Alternatively, cells bound to a drug candidate or other entity can be released from the column and studied. For example, cells can be disrupted to create membrane fragments consisting of cell surface components bound to drug targets. The drug targets and the drug leads can be identified using methods such as mass spectrometry.

Drug effectiveness and toxicity can be studied using these techniques. One or more columns loaded with living cells may be subjected to drug candidates of different types, under varying conditions and varying concentrations. Cells may be eluted to determine the relative number of cells affected by the drugs. These drugs include antibiotics or combination of antibiotics.

Certain drug candidates target cellular molecules, organelles, nucleic acids, etc. in the cytosol rather than on the cell surface. The target may be some large functionalized particle, such as a liposome, that can enter cells via endocytosis. In these studies, the cell can be captured by the column via a surface marker. Then, cell cytosol-specific drug candidates can be introduced to the cells on the column. Using this method, the uptake or binding of the drug can be studied. Unidirectional flow or bidirectional flow can be used. Experiments can be performed in parallel comparing variables such as drug type or concentration. The cells may be eluted and the effect of the drug on the cells may be analyzed.

Alternatively, drug candidates can be immobilized on a column and different cell types can be passed through the column to identify and then characterize interaction. In some embodiments, cells can be manipulated prior to passing them through the column. For example, cells can be mixed with a drug candidate and subjected to competition experiments with other drug candidates present on the column.

Cell Clean-Up

The columns and methods described herein can additionally be used for cell clean-up. For instance, it can be desirable to separate cells from contaminants, collect materials from cell populations or perform buffer exchange. Existing methods for cell clean-up include magnetic beads, dialysis and centrifugation which are time-consuming, single equilibrium procedures. The columns and methods of the invention provide a rapid alternative and offer the advantage of being a multi-equilibrium process.

In some embodiments, cells are purified away from contaminants by capturing contaminants on the column while cells pass through unencumbered. Contaminants can be captured on the solid phase using for example, an affinity group, aptamer capture, ion exchange or other strategies. Alternatively, size exclusion can be used to separate cells from contaminants. Using size exclusion, cells might pass through the column quickly while smaller contaminating molecules might enter the solid phase which would cause them to pass through the column more slowly.

Diagnostics

Some requirements of a good diagnostic procedure are that it is rapid, simple, enriches the sample before detection, removes nonspecific materials (that could give a signal), high sensitivity, high signal to noise, and linear signal.

The columns and methods of the invention can be used for a number of diagnostic applications including oncology, virology and infectious diseases. Diagnostic applications include isolation of any cell type and the option of additional cell characterization on column or post column. One application is the identification of pathogens such as viruses, bacteria, fungi and protozoa from a patient sample. Another application is the isolation and characterization of cancer cells, such as circulating tumor cells (CTCs) as described below in Example 3. Isolation of CTCs is useful for early cancer detection, characterization of tumor cells, monitoring disease treatment, monitoring progression or remission.

Diagnostic applications of the invention can be used in a variety of settings. In certain embodiments, diagnostics are utilized in a research setting such as academia, biotechnology or pharmaceutical company. In other embodiments, the columns and methods of the invention can be used in point of care settings including emergency rooms, intensive-care units, patients' bedsides, physician's offices, pharmacies and blood banks. In still other embodiments, diagnostic applications can comprise in-home tests. Diagnostics are also useful in a corporate setting such as the food industry.

Diagnostic target cells can be any cell type listed above. As described above, cells are not defined herein as limited to entities capable of self-replication. Included in the definition of cells are viruses, parasites and exosomes and organelles. A non-limiting list of diagnostic targets include mammalian cells, human cells, cancer cells, circulating tumor cells, viruses, bacteria fungi and parasites. A non-limiting list follows: *Shigella, Salmonella, E. coli, Helicobacter pylori, Campylobacter, Chlamydia, Gonococcus, Streptococcus, Staphylococcus, Mycoplasma, Trichomonas vaginalis, Clostridium botulinum*, HIV, Hepatitis A, B and C, Herpes, Amoeba/parasites, *Entamoeba histolytica, Acanthamoeba* and *Naegleria, Cryptosporidium, Giardia*, Fungi such as Coccidiodomycosis (Valley Fever), blastomycosis, histoplasmosis, yeast—*Candida albicans* and other *Candida* sp. (hospital infections, blood infections) and opportunistic pathogens such as Cryptococcosis and Aspergillosis.

Although it is not required for all diagnostic applications, a label can be employed. For example, cells can be captured and then labelled on the column. Alternatively, cells can be labelled prior to column capture. When cells are labelled prior to capture, the label can aid in cell capture. In some embodiments, the label can actually be the entity captured on the column. Labelled cells captured on the column can be washed, eluted and a detection step performed. In another embodiment, cells can be labelled following elution from the column. An advantage to this approach is that a homogeneous cell population can be obtained prior to the labelling step.

In some embodiments, only a few (or relatively few) particular cell surface markers are used to capture a cell on the medium. For this example, we will call these markers Type A. This leaves most of the Type A on the rest of the cell untouched. The labeling of a cell can be performed by reacting these remaining, excess Type A cell markers. In other embodiments, the labeling of a cell is performed by reacting a cell marker, Type B, which is not used for capturing the cell on the column. This strategy is especially useful for on-column tagging or labelling of the cells. By targeting a different cell marker for labeling, the cell is less likely to be removed or eluted in the tagging process.

In some embodiments, the tagged cells are eluted and then detected. In some embodiments, the elution of the tagged cell is performed by changing the chemical nature of the linking or capture reagent.

Labels can aid in detection. A variety of labels can be used for this purpose. For example, a fluorescent dye-labelled antibody or Fab can be used. In addition, an antibody or Fab can be conjugated with any kind of tag that aids detection. In addition to dyes, non-limiting examples of tags include radioactive labels, proteins, enzymes (e.g., horse radish peroxidase), and metals including rare earth metals. Labels are not limited to tagged antibodies or Fabs; they include anything that can bind the cell surface such as a protein, a dye or other molecule.

Dye-labelled antibodies or Fabs can be used to label specific cell surface markers and viable versus dead cells. Dyes used to label proteins include Ellman's Reagent, Coomassie Blue, Lowry reagents and Sanger's reagent.

Post-column label detection can be carried out using a number of different methods. For instance, detection can be done with flow cytometry, a microscopy, a spectrophotometry, mass spectrometry, a colorimetric reader, a protein assay or a nucleic acid assay.

In alternate embodiments, on-column detection can be utilized. On-column detection can be performed for example, by reflectance (UV or visible), fluorescence, colorimetric detection (e.g., ELISA), chemiluminescence and others.

Cell-Based Stationary Phase for Liquid Chromatography

Columns of the invention can be used to produce and use a stationary phase comprised of cells, referred to herein as the cell-based stationary phase. The cells can be attached to a substrate and used to measure the interaction of analytes with a cell-based stationary phase. The cell stationary phase may be comprised of live or active cells. Active is defined herein as a cell that is not only living, but can undergo biological processes while attached to the column medium. Samples injected into the mobile phase enter the column and interact with the cell-based stationary phase. These interactions can be identified and quantified. Both the mobile phase analytes and the stationary phase will can be analyzed. Retention data and column interaction data can be collected and analyzed. In many cases, the liquid phase flow through the column is unidirectional however, in some cases, bidirectional flow may be employed.

Generally, cells that are placed on the cell-based stationary phase are viable however, it is not mandatory. Cells attached to affinity resins packed into a chromatographic bed have surface groups of various types that can interact with analytes flowing through the column. These groups include proteins, glycoproteins, carbohydrates, lipids, sugars and other groups. The proteins may contain phosphate groups, glycans, etc. Analytes such as drug candidates or antibody-drug conjugates can interact with these groups by pumping them or injecting them into a liquid phase flowing through columns. Examples of interactive entities include antibodies (e.g. from antibody libraries), antibody-drug conjugates, Fabs, proteins, enzymes, sugars, nucleic acids, lipids, ion exchange and other groups. This interaction can be measured in different ways, depending on how the chromatography is performed and the kinetic rate constants of the on/off interaction of the cells with the stationary phase. Properties of the cells can be analyzed after they are removed from the column. For example, cells can be removed from the column after chromatography to characterize their properties. They can be stained to count the numbers of live cells and dead cells.

Any substrate can be used to form the cell-based stationary phase including affinity, ion exchange resins and others. In fact, any chemistry directed to cell surface markers can be used.

With living cell stationary phase chromatography, the types of interaction of an analyte with the cell stationary phase can be characterized. Types of measurement include the kinetics of interaction, the extent or magnitude of interaction, the relative selectivity of the interaction and other parameters. The column may be used to separate analyte materials that have different selectivities. For example, a first and a second analyte material may be associated or bound to a stationary phase. An eluent may be added to the column and the first material may be removed from the column faster or more easily than the second material. This difference in selectivity may be measured.

In one example, cell chromatography may be used to determine which reagents interact with stem cells and the effect of that interaction on the cells. Stem cells are loaded onto a column to make a living cell stationary phase. Then, various analytes are introduced into the column under controlled chemical and physical conditions. Multiple experiments may be performed in parallel. Using chromatography, it can be determined the extent of interaction of a reagent with the stationary phase and how the interaction can be controlled. The relative affinity of two or more analytes can be measured. Then, after the chromatography is performed, the cells can be eluted and analyzed to determine the effect of the interaction on the stem cells.

Chromatography with a living cell stationary phase may be used to examine interaction of a particular type of cell and drug candidates. Cancer cells from a particular patient may be loaded onto a column. Existing drugs may be introduced into the column and the chromatographic interaction measured to determine if a particular drug, series of drugs or a mixture of drugs may be suitable for treatment of the patient. After exposure and chromatography measurement of the analytes, the cells can be removed and analyzed to determine the effect.

The cells are preferably living and stable in flowing fluid through the column. The cells are not sheared from the column beads or media by the stream of liquid flowing through the column. The cells remain alive while attached to the column and remain available for use as a liquid chromatographic stationary phase for at least 30 min, at least 1 hour, at least 2 hours, at least at least 3 hours, at least 4 hours, at least 5 hours, at least 6 hours, at least 12 hours, at least 1 day, at least 2 days, at least 3 days, at least 4 days, at least 5 days, at least 6 days or even longer.

Analytes of various types are introduced to the column of the invention with a mobile phase fluid flowing through the column. The analytes interact with the cell stationary phase to different extents depending on the kinetics and selectivity of stationary phase for the analyte. The extent of interaction can be measured with individual analytes or under competitive conditions with two or more analytes in a matrix of background conditions. In addition, analyte materials of interest may interact with the cell stationary phase and be captured or removed from a complex matrix solution.

There are two general methods to prepare the system for capture of the cells by the column. In one method, the column medium contains sites that interact with the surface of the target cells. The medium may have the sites or may be conditioned to gain the sites that interact with the columns. An example of this is where the column contains nucleic acids, lipids, peptides, antibodies or Fabs that can capture cells through surface markers. In another example, the column contains chelating or ion exchange sites which can interact directly with a cell or may contain a reagent that interacts with cells. In another example, the column contains aptamer sites that interact with the surface of the cells.

Another method may be to treat the cells with antibodies or other reagent(s) that allow the cells to bind the column medium. For example, antibodies can interact with cells in solution. The cells attached to antibodies can be captured by a Protein A or Protein G column. In another example, each antibody molecule may contain another functional group such as a biotin. The biotin entity on the antibody (which is attached to the cell) may be captured by a streptavidin resin in the column.

Different protocols may be used to capture cells for purification. In one embodiment, the resin bead is activated or may be activated with an entity to be able to capture cells. After activation, a sample may be processed to capture the cells in the first step of purification. In another embodiment, cells may be treated or activated and then captured by flow cells through the column.

In order to produce the cell stationary phase columns, the column and substrate must have the same cell accessibility characteristics as columns used to capture and purify cells. That is, the cells are accessible to chemical interactions. Cells are not trapped in dead spaces and cells are not damaged by the frits or resin. The cell stationary phase columns are characterized by low backpressure, low dead volume, and very little dead space.

In one procedure, the cells are attached to the surface of the column packing resin and then the resin containing the cell stationary phase is packed into a column. The cells can be attached to the resin substrate in a slurry. This attachment step can also be accomplished in two ways. The cells may be activated with an antibody or other chemical entity that in turn, can attach to the resin. Or, the resin substrate may be activated with an antibody or other chemical entity that in turn, allows attachment of the cells. The cells are then mixed with the resin and attach to the substrate, producing the cell stationary phase. Once the cell stationary phase is produced, the resin is packed into the column.

Resins can be activated to be able to capture cells to make a cell stationary phase. One example of this is to load an antibody onto Protein A column resin beads. The antibody is selective for surface proteins on the target cells. Alternatively, cells can be activated to be able to attach to resin beads. An example of this approach is the attachment of a His-tagged Fab to cells. After removing excess Fab material by centrifugation, the cells can be introduced to an IMAC resin bead. The cells attach to the beads through the His-tagged Fab.

In a different method, a medium or resin substrate (not containing the cells) is packed into a column. The medium contains an affinity group capable of cell capture. The cells are introduced into the column and the cells attach to the substrate producing the cell stationary phase. This capture step can be accomplished in several ways. For example, the cells may be activated with an antibody, aptamer or other chemical entity that in turn, can attach to the resin. In another method, the resin substrate may be activated with an affinity group such as an antibody, aptamer or another chemical entity that can attach the cells.

In one example, a column was prepared by gluing a frit on one end, packing the column and then gluing a second frit on the top of the column. A 37-micron pore, 60-micron thick Nitex screen frit was attached to the end of an acrylic tube 0.750 inches long, 0.500-inch outer diameter and 0.375-inch inner diameter. Packing was accomplished by standing the column on a stand with deep-well plate beneath the column that allowed liquid to flow out of the lower end. An aqueous slurry of agarose resin, 45-165-micron particle size, was transferred to the column by pipette. The packing material was not compressed. Excess liquid drained away filling the column with resin. Additional slurry was added until the bed of the column reached the top of the column. A Nitex screen of the same material used for the other frit was glued onto the column end using a methylene chloride solvent.

Silicone tape was wrapped round the column to increase the diameter. Then, two 10 mL plastic syringe bodies and male luer connections were cut to the 1 mL volume mark and placed on the end of the column. The column body was wrapped with stretchable silicone tape to seal the column body. Male luer connections were connected to the inside of clear flexible Tygon tubing 0.250-inch outer diameter to connect to the injector and fraction collector.

In a second example, the cells are attached to the column. A His-tagged Fab is pumped through the column loading the column completely with the Fab. The Fab is selective for a surface protein on the HeLa cancer cell line. After washing the column, HeLa cells are pumped into the column loading cells onto the surface of the stationary phase. The column now contains a HeLa cell-based stationary phase.

Figure 7:
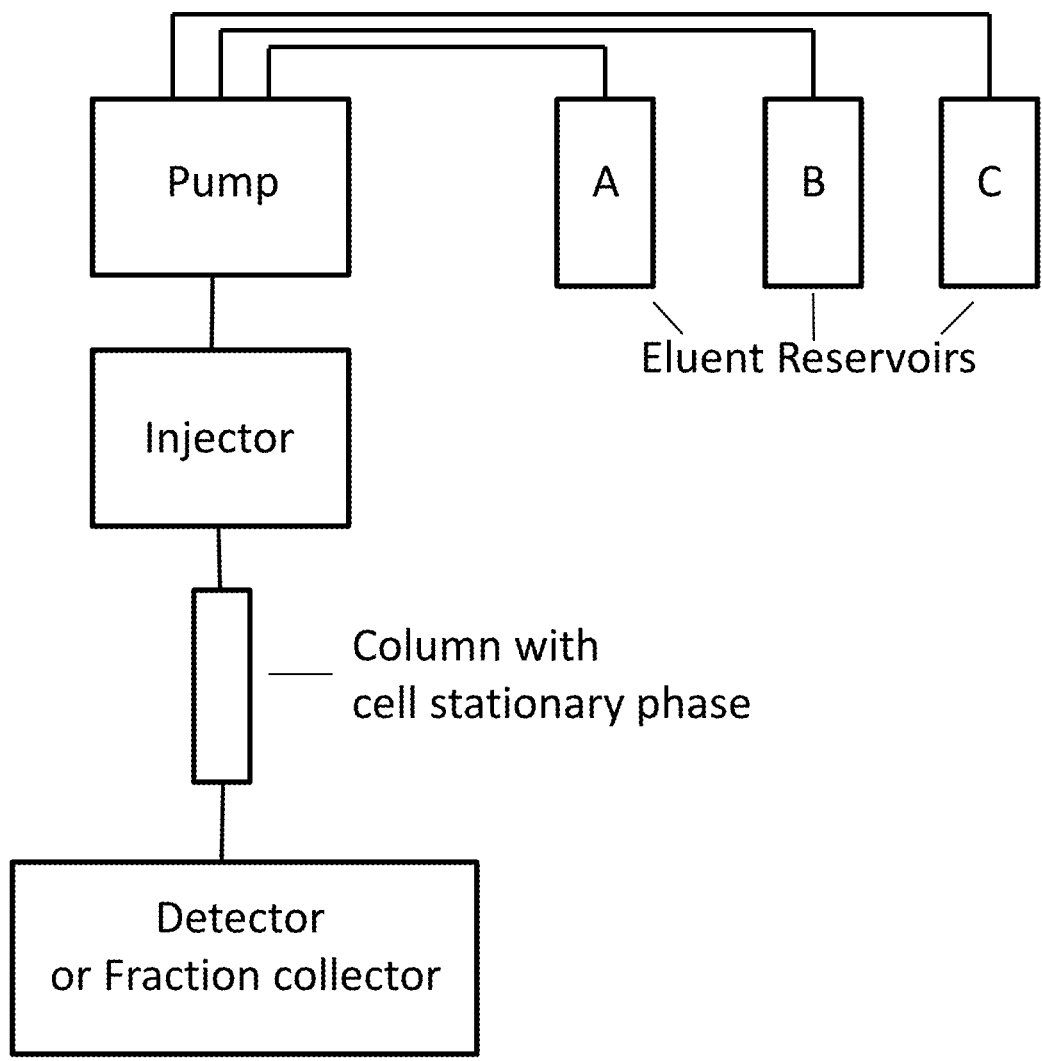
FIG. 7 is a depiction of one embodiment of a column having a cell stationary phase in a chromatographic system.
Figure 8:
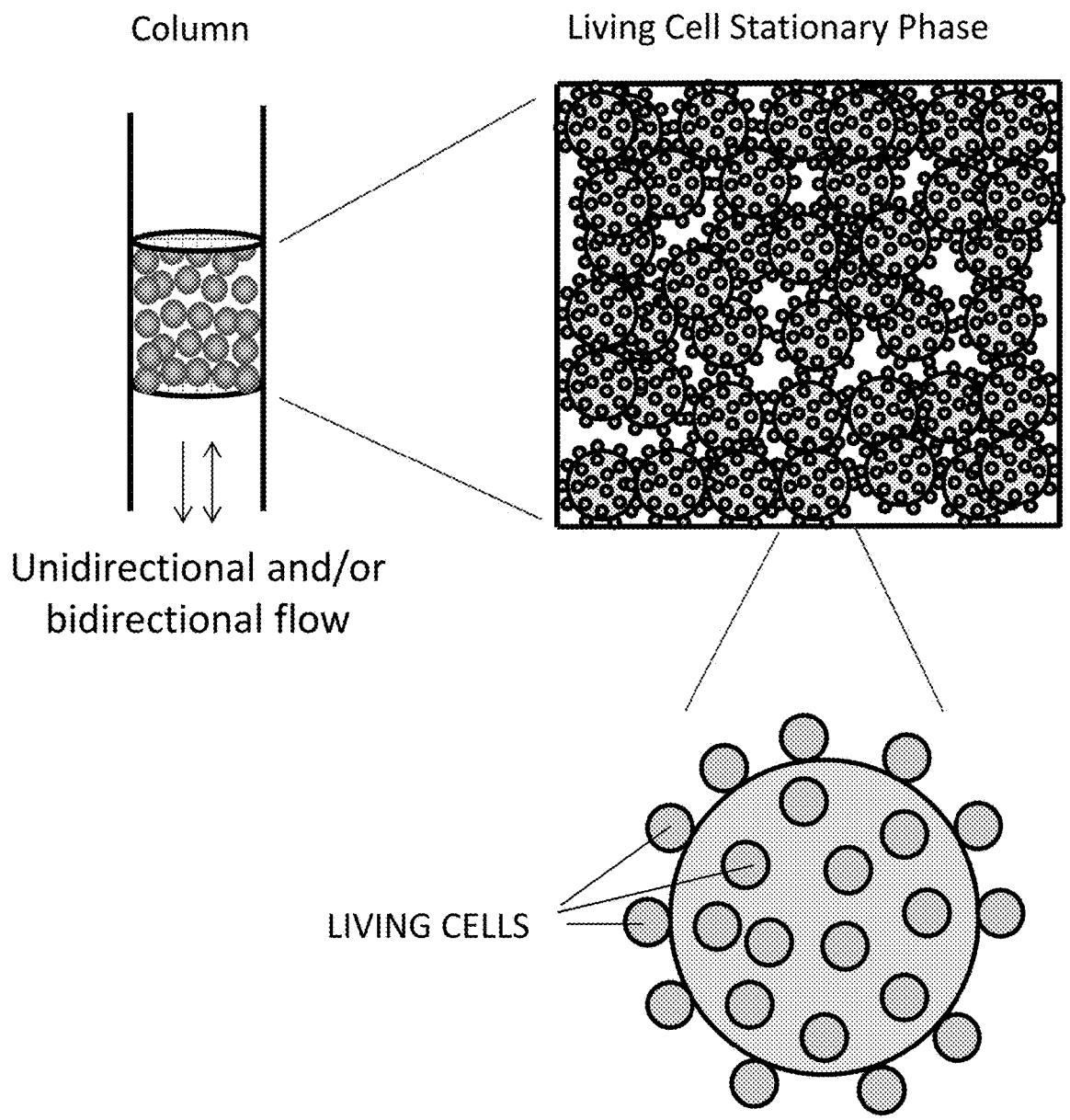
FIG. 8 is depiction of how cells are located on the surface of beads that are packed into a column to form cell stationary phase column.

A chromatographic column in a chromatographic system is shown in FIG. 7. A column comprised of a cell stationary phase is shown in FIG. 8.

Once the cell stationary phase column is prepared, chromatography can be performed. Cells captured on the column can be interrogated with groups of compounds or analytes to identify those that bind cells with the desired affinity. For instance, a library of compounds can be passed through the column to determine which materials in the library have an affinity for the cells on the column. The sample containing the library is added to the column. The column can be washed. The stringency of the wash may be varied to control capture of library materials. Then, an eluent or high stringency wash can be used to elute the compounds alone or the cells with compounds attached.

The identity and concentration of the compounds recovered may be determined by liquid chromatography or mass spectrometry methods. The concentration of the various compounds may indicate the ability of the cells to capture a particular compound.

The interaction of different materials with the stationary phase can be measured using various chromatographic techniques. The extent of interaction under different conditions may be measured. The identity of materials interacting may be determined. The ability of a reagent to bind to the cell may be measured. This measurement may be performed relative to an eluent reagent or may be performed relative to another analyte reagent.

The type of chromatography that can be performed depends on the kinetic rates of the analyte interaction with the cell stationary phase. For rapid kinetic interaction of analytes with the column, partitioning chromatography may be performed. Partitioning chromatography is performed using unidirectional flow. Measurement of the analyte interactions may be performed using retention times or related values such as capacity factors. Partitioning chromatography is performed under isocratic and gradual gradient conditions.

Other types of chromatography that may be performed for rapid analyte kinetic interaction with the cell stationary phase include step gradient chromatography, displacement chromatography and frontal/breakthrough curve chromatography. Step gradient and displacement chromatography can be performed with either bidirectional or unidirectional flow. Frontal/breakthrough curve chromatography is performed with unidirectional flow.

For slower analyte kinetic rates of interaction with the cell stationary phase, step gradient chromatography, displacement chromatography or frontal/breakthrough curve chromatography can be employed. Also in these cases, step gradient and displacement chromatography can be performed with either bidirectional or unidirectional flow. The step gradient may be one step gradient, after an optional wash or multi step gradient. Frontal/breakthrough curve chromatography is performed with unidirectional flow.

Some interactions may be additive. For example, calcium may be added to membrane channels. In this case, the kinetic rate of uptake would be higher than release and breakthrough curve measurement may be more appropriate.

Partitioning chromatography may require an injection of a slug of analyte into a flowing eluent stream, provided the partitioning is rapid. But large injection volumes can be employed if the selectivity of the analyte for the column is high. Breakthrough chromatography requires a continuous uniform (injection) supply of analyte. Injection is at the top or inlet of the column for partitioning or gradual gradient chromatography. Displacement chromatography generally requires a large injection ensuring that the stationary groups are displaced with the eluent. Injection can be at the top of the column or at the bottom of the column for back and forth flow.

Partitioning interaction of analyte and eluent molecules with living cell chromatographic columns is a competitive process that relies on the kinetics of interaction being rapid enough to move analyte molecules down the column. To a certain extent, slow kinetics can be compensated for by using very slow mobile phase flow rates or by the introduction of high concentrations and/or large volumes of the analyte or eluent molecules to the column. Bidirectional flow can compensate for slow kinetics by passing the molecules through the column until the equilibrium of interaction is complete.

If the kinetics of analyte and eluent are rapid, the analyte will move down the column to produce a peak eluting at the end of the column. Peaks may be detected by collecting fractions of materials as they elute and analyzed or in some cases, on line detection may be used.

The peak or peaks that are eluted will be symmetrical when the kinetics of interaction are very rapid. If the kinetics of interaction are slower, the peaks will be broader and in some cases, the peaks will tail.

The following steps are an example of a partitioning chromatographic procedure using a living cell stationary phase column.

1. Treat or activate column or cells to provide suitable conditions for the column media to be able to capture cells.
2. Load cells onto column from a flowing stream. Loading may be performed in a unidirectional or bidirectional mode.
3. Wash nonspecifically in the bound materials from the column using a flowing stream.
4. Pump an eluent through the column and through the detector to ensure that all material has been washed from the column and a stable detection baseline is achieved.
5. Inject a single or mixture of analytes into the column.
6. Pump an eluent solution through the column and measure retention of analyte or analytes.
7. Optionally, recover cells from column stationary phase after exposure to analytes and analyze.
8. Optionally, lyse cells or elute the components of the cells for analysis. The lysis step may be done partially, or over a longer time period using gentle conditions to remove components of the cell for processing and/or analysis.
9. Remove and recover cells for analysis of the cells and/or further research and development processing.

Detection may be continuous or fractions may be collected and analyzed. Analyte measurements include retention time, capacity factory, selectivity coefficient and others.

The bidirectional flow step gradient and displacement chromatography can be can be performed with the pipette, syringe, gas pressure/vacuum chamber, peristaltic pumps and living cell stationary phase columns of the invention. This type of chromatography can be operated with a manual or electronic controlled pipette or automated robotic liquid handler operated as a single channel or multiple columns in parallel or up to 96 channels are operated in parallel.

The following steps are an example of gradient chromatographic procedure using a living cell stationary phase column.

1. Treat or activate column or cells to provide suitable conditions for the column media to be able to capture cells.
2. Load cells onto column from a flowing stream. Loading may be performed in a unidirectional or bidirectional mode
3. Wash nonspecific bound materials from the column using a flowing stream.
4. Pump an eluent through the column and through the detector to ensure that all material has been washed from the column and a stable detection baseline is achieved.
5. Pump a library mixture of analytes into the column.
6. Wash the column with an eluent to remove all excess non-attached analytes.
7. Optionally, recover cells with analytes attached and analyze.
8. Optionally, remove analytes from column with step gradient eluent solution. Recover, detect and analyze the analytes.
9. Optionally, remove analytes from column with continuous gradient eluent solution. Recover, detect and analyze the analytes.
10. Optionally, recover cells from column stationary phase after exposure to analytes and analyze.
11. Optionally, lyse cells or elute the components of the cells for analysis. The lysis step may be done partially, or over a long time period using gentle conditions to remove components of the cell for processing and/or analysis.

12. Remove and recover cells for analysis of the cells and/or further research and development processing.

For slow kinetic interactions, the mobile phase flow rate and the linear flow velocity may be adjusted (lower) if necessary to compensate for the slower kinetic rates. These adjustments are options for all of the various types of chromatography.

The following steps are an example of displacement chromatographic procedure using a living cell stationary phase column.
1. Treat or activate column or cells to provide suitable conditions for the column media to be able to capture cells.
2. Load cells onto column from a flowing stream. Loading may be performed in a unidirectional or bidirectional mode
3. Wash nonspecific bound materials from the column using a flowing stream.
4. Pump an eluent through the column and through the detector to ensure that all material has been washed from the column and a stable detection baseline is achieved.
5. Pump and capture analytes on the sites of the cells in the column.
6. Wash the column with an eluent to remove all excess non-attached analytes.
7. Introduce a second analyte and measure displacement of first analyte from column.
8. Optionally, remove analytes from column with eluent solution. Recover and analyze the analytes.
9. Optionally, recover cells from column stationary phase after exposure to analytes and analyze.
10. Optionally, lyse cells or elute the components of the cells for analysis. The lysis step may be done partially, or over an extended time period using gentle conditions to remove components of the cell for processing and/or analysis.
11. Remove and recover cells for analysis of the cells and/or further research and development processing.

Figure 9:
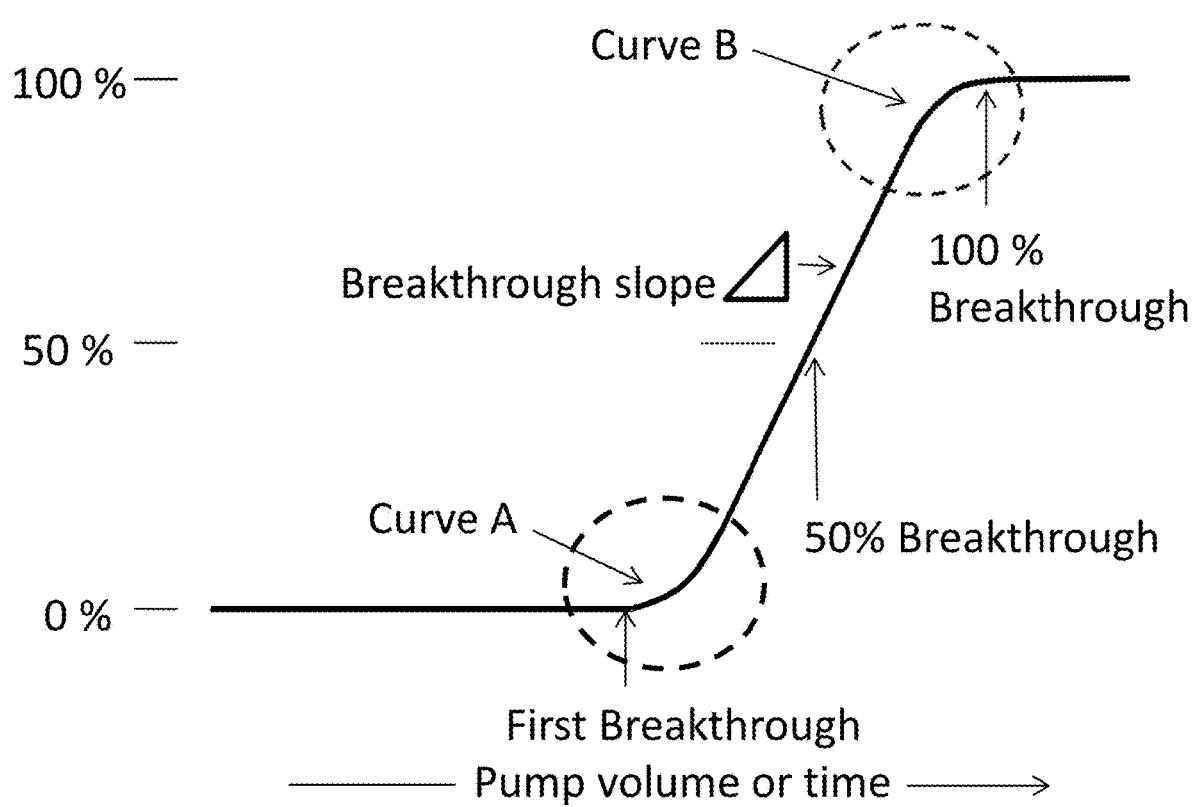
FIG. 9 shows the features of a curve obtained from breakthrough chromatography.

The geometry of a breakthrough curve is depicted in FIG. 9. The x-axis denotes the time the analyte is pumped or the volume of the analyte pumped. The y-axis shows the amount of analyte that exits the column relative the column input concentration. To start, analyte is pumped through the column and is taken up by the stationary phase. The first breakthrough is where the analyte is not completely taken up from the column. The curvature of slope A is an indication how fast the analyte is taken up by the stationary phase. A long, extended slope of curve A indicates a slow on-rate of the analyte. The slope of the breakthrough is an indication of the kinetics of uptake and release and of how the column is packed. An ideal breakthrough is vertical, but in practice, all breakthrough curves have a slope. The 50% breakthrough point shows how much analyte is taken up by the column. This is calculated by multiplying the volume at which 50% breakthrough occurs by the concentration of the analyte being pumped through the column. Curve B is the curve leading into the point at which no analyte is being taken up by the column, 100% breakthrough. A long, extended curve at this point indicates a slow off-rate and/or a slow on-rate of the analyte.

Competing materials can be added while performing breakthrough chromatography. Generally, small-diameter beads packed in columns with low dead volume will give breakthrough curves with steeper slopes. In these cases, the mass transfer and diffusion to the surface of the bead are decreased so that the kinetic interaction and the extent of interaction can be measured.

The following steps are an example of breakthrough chromatographic procedure using a living cell stationary phase column.
1. Treat or activate column or cells to provide suitable conditions for the column media to be able to capture cells.
2. Load cells onto column from a flowing stream. Loading may be performed in a unidirectional or bidirectional mode
3. Wash nonspecifically-bound materials from the column using a flowing stream.
4. Pump an eluent through the column and through the detector to ensure that all material has been washed from the column and a stable detection baseline is achieved.
5. Pump an analyte into the column. The breakthrough of the analyte is measured by the initial breakthrough, shape and slope of the breakthrough, 50% breakthrough point and the shape of the slope to analyte plateau.
6. Optionally, recover cell with analyte attached and analyze.
7. Optionally, remove analyte with eluent solution. Monitor and analyze the removal of the analyte from the cell stationary phase.
8. Optionally, recover cell after exposure to analyte and analyze.
9. Optionally, repeat with a second analyte. Pump a second analyte through the column and measure breakthrough parameters. Measure the difference of selectivity cell stationary phase column of first and second analyte.
10. Optionally, repeat with several other analytes and measure the difference in selectivity of the different analytes.

Breakthrough curves measure effective capacity for a particular analyte, the kinetics of on interaction and the kinetics of off interaction. Analyte measurements include slope, starting and ending breakthrough shape, the breakthrough plateau shape and other parameters. Competing analyte materials can be combined while performing breakthrough chromatography.

When the analytes are dyes that bind to specific cell surface proteins, breakthrough curves can also be used to measure the expression of cell surface proteins. Proteins expressed on the surface of mammalian cells are often universal. Disease cells may express cell surface proteins in concentrations that are different from non-disease cells. In addition, the ratio of one cell surface proteins to another cell surface protein has been shown to be different when comparing diseased versus non-diseased cells. This information can be used to either design new therapeutics directed at detecting the stoichiometry of cell surface proteins, guide the administration of drug cocktails to individual patients, and to diagnose disease.

In the columns and methods of the invention, cells can be captured from rapidly flowing streams. As an example, for columns having diameters ranging from 2 mm-4 mm, capture can be from cells moving through the column at 0.01-20 mm/sec, 0.1-10 mm/sec, 0.2-5 mm/sec, 0.3-3 mm/sec, 0.4-2 mm/sec and 0.5-1 mm/sec. The linear velocity at 0.1-10 mm/sec corresponds to absolute flow rates of about 100 µL/min to 10 mL/min respectively. For columns with diameters ranging from 4 mm-10 mm, capture can be performed from cells moving through the column at 0.05-20 mm/sec, 0.1-10 mm/sec, 0.2-5 mm/sec, 0.3-3 mm/sec, 0.4-2 mm/sec and 0.5-1 mm/sec. The linear velocity at 0.1-10 mm/sec corresponds to absolute flow rates of about 500 µL/min to 5 mL/min respectively. For columns with diameters ranging from 10 mm-15 mm, capture is from cells moving through the column at 0.01-20 mm/sec, 0.1-10 mm/sec, 0.2-5 mm/sec, 0.3-3 mm/sec, 0.4-2 mm/sec and 0.5-1 mm/sec. For these columns, linear velocity at 0.1-10 mm/sec corresponds to absolute flow rates of about 1 mL/min to 100 mL/min respectively. As yet another example, for column with diameters ranging from 15 mm-40 mm, capture is from cells moving through the column at 0.01-20 mm/sec, 0.1-10 mm/sec, 0.2-5 mm/sec, 0.3-3 mm/sec, 0.4-2 mm/sec and 0.5-1 mm/sec. For these columns, linear velocity at 0.1-10 mm/sec corresponds to absolute flow rates of 5 mL/min to 500 mL/min respectively.

The following steps are an example of a chromatographic procedure for purification of cells for recovery and detection.
1. Treat or activate column or cells to make the column suitable to be able to capture cells.
2. Load cells onto column from a flowing stream.
3. Wash non-specific bound materials from the column using a flowing stream.
4. Optionally tag cells with a reagent that reacts with a group on the surface of the cell. The tag reacts with an attachment group or entity that is optional different than the attachment group used to capture the cell to the column.
5. Optionally measure cells with the cells attached to the column. Optional detectors are infra-red, surface and transmission VIS/UV, fluorescence, chemiluminescence spectrophotometers.
6. Optionally lyse cells or elute the components of the cells for analysis. The lysing may be done partially, or over a longer time period using gentle conditions to remove components of the cell for processing and/or analysis.
7. Remove and recover cells for analysis of the cells and/or further R&D processing, growing or transforming of the cells or further research and development and/or therapeutic use of the cells.

Figure 10:
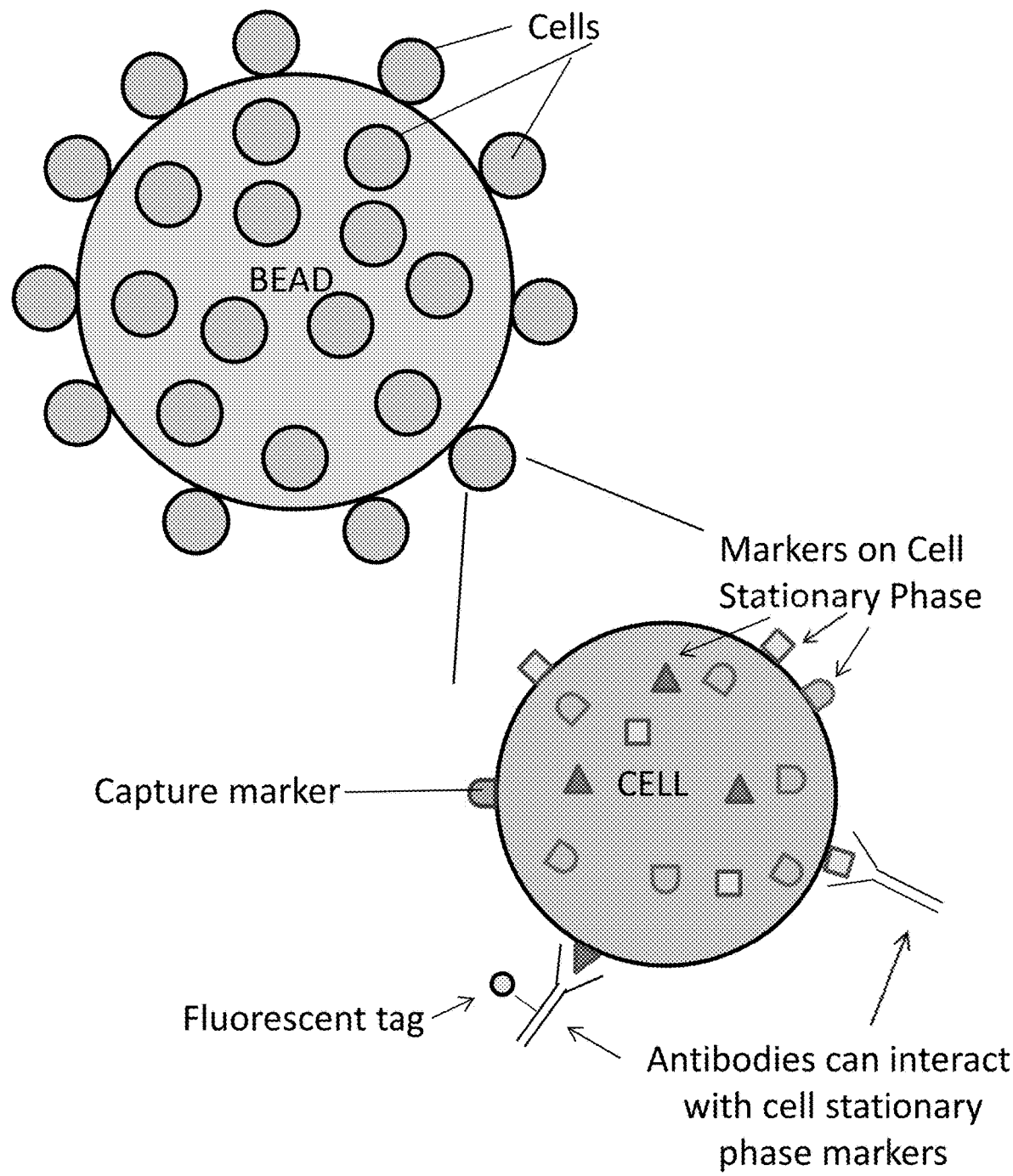
FIG. 10 is a depiction of the different markers on the cell surface.

Cell surface markers can be used in a number of ways in the columns and methods of the invention as shown in FIG. 10. In some embodiments, cell surface markers can be used to attach cells to the column solid phase. Other markers may be used to tag or label the cells. Tagging or labeling cells can be performed prior to capture, on the column after capture or even after cells have been eluted from the column. Other markers can be a source for the interaction of analytes with the cell stationary phase. In some embodiments, different markers are used for different purposes as shown in FIG. 10. For example, one marker may be used for on-column cell tagging while another marker might be used for attaching cells to the bead. In this way, the tagging process is less likely to interfere with the attachment of the cell. Similar strategies are used for cell stationary phase experiments. Cell surface markers can interact with antibodies, aptamers, drugs, reagents, (fluorescent) tags, small molecules, metals, proteins, polypeptides and a variety of other entities.

Figure 11:
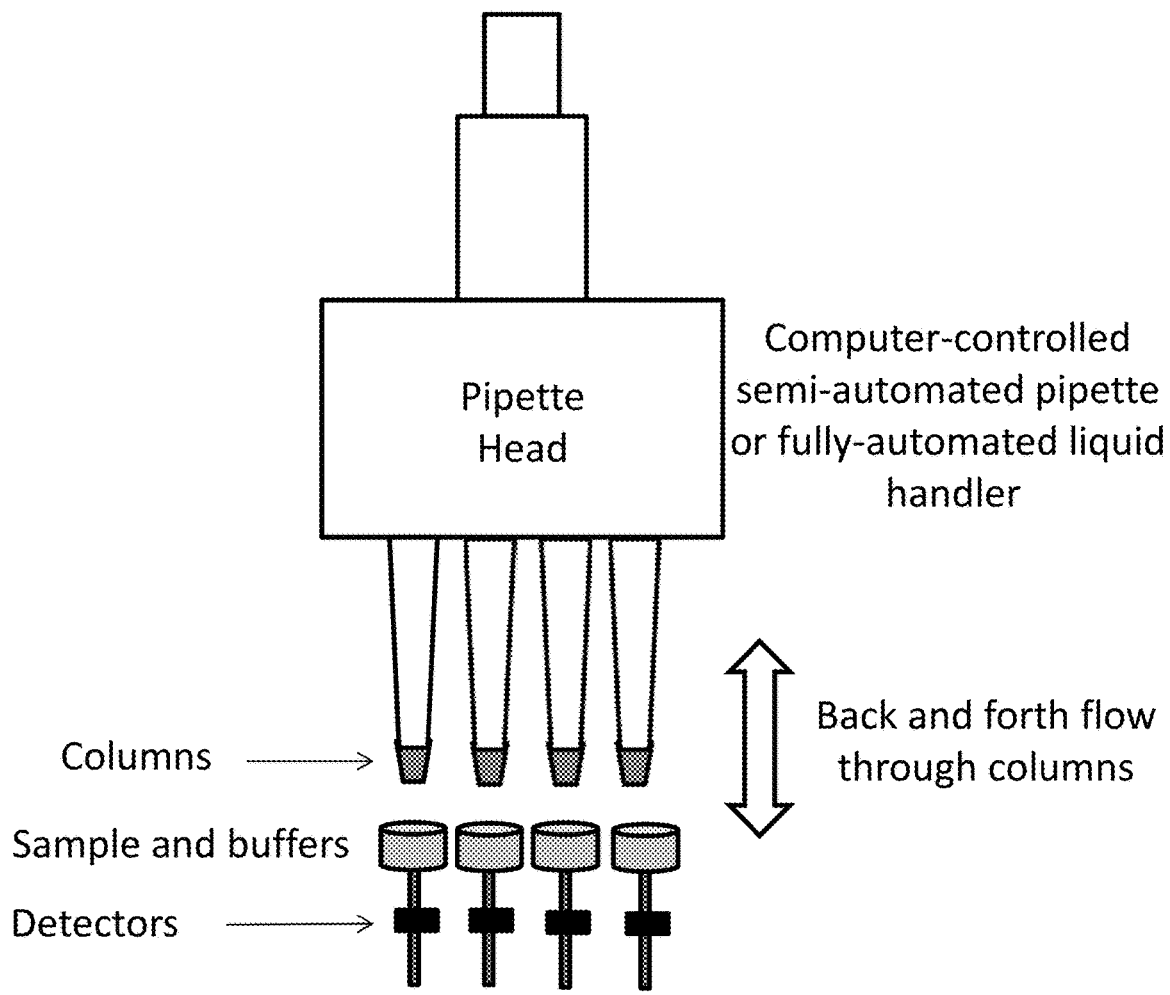
FIG. 11 is a depiction of a pipette tip chromatographic instrument with a pipette tip cell stationary phase column that can operate in a bidirectional mode. The instrument can be used for cell purification and diagnostic applications and cell stationary phase applications.

Columns, instruments and methods of the invention to purify and manipulate cells can be in different forms and configurations. An example of a general configuration is an instrument that operates primarily with back and forth fluid flow is shown in FIG. 11. The instrument may be used for cell purification, cell diagnostics or cell stationary phase chromatography.

In the figure, a pipette is fitted to a column of the invention. In other examples, a syringe pump, gas pressurized/vacuum chamber pump or peristaltic pump can be fitted to a column of the invention. The pipette may be manual or electronic. The electronic pipette may be controlled with firmware and software contained within the pipette or may be controlled by an external computer or control. The pipette may be operated in a free-standing mode. In this mode, it is not necessary to hold the pipette. In addition, the pipette is not held in place with the stand. Instead, the open lower end of column is inserted into a sample-containing well (e.g. in a deep-well plate) or assembly and the pipette is operated electronically and semi-automatically using back and forth flow. The pipette is operated without manual intervention until it is placed into the next solution where the pipette again operates without manual intervention.

The pipette may be a single channel or multichannel pipette. The pipette, syringe pressure chamber or other pumping mechanism may be in the form of an automated robotic liquid handler where a single channel is operated, multichannel are operated in parallel, or up to 96 channels are operated in parallel. Columns of the invention may be operated one at a time or in parallel operation two or more at a time up to 96 at a time and optionally more.

In certain embodiments, the instrument can be controlled or programmed wirelessly. Examples of wireless communication methods include light, magnetic, electromagnetic, sound, wireless USB, Bluetooth, infra-red, radio, optical, sonic and ultrasonic.

In some embodiments, the instrument can be under cordless control. The terms, "wireless" and "cordless" should not be confused. The term cordless is generally used to refer to a powered electrical or electronic device that is able to operate from a portable or contained power source. In these embodiments, the instrument can be controlled by batteries.

The flow of fluids through the column is bidirectional back and forth with optional uni-directional flow for some methods. Semi-automated and automated refer to control of fluid through the column and placement and movement of the columns. Movement of the pipette or other pumping device from well to well can be performed manually. Optionally, the flow can be directed to a detector. The detector may measure a property of a well, or the detector may have flow through capability and a flowing stream is analyzed.

Columns of the invention may also be used with a fully automated liquid handler equipped to engage columns of the invention and process samples containing cells. The flow of fluids through the column is bidirectional back and forth with optional unidirectional flow for some operations. Movement of the column from well to well is performed automatically. Optionally, the flow coming out the end of the detector can be directed to a detector. The detector may measure a property of a fluid with a well where the fluid has been deposited, or the detector may have flow through capability and a flowing stream coming from the column is analyzed.

Figure 12:
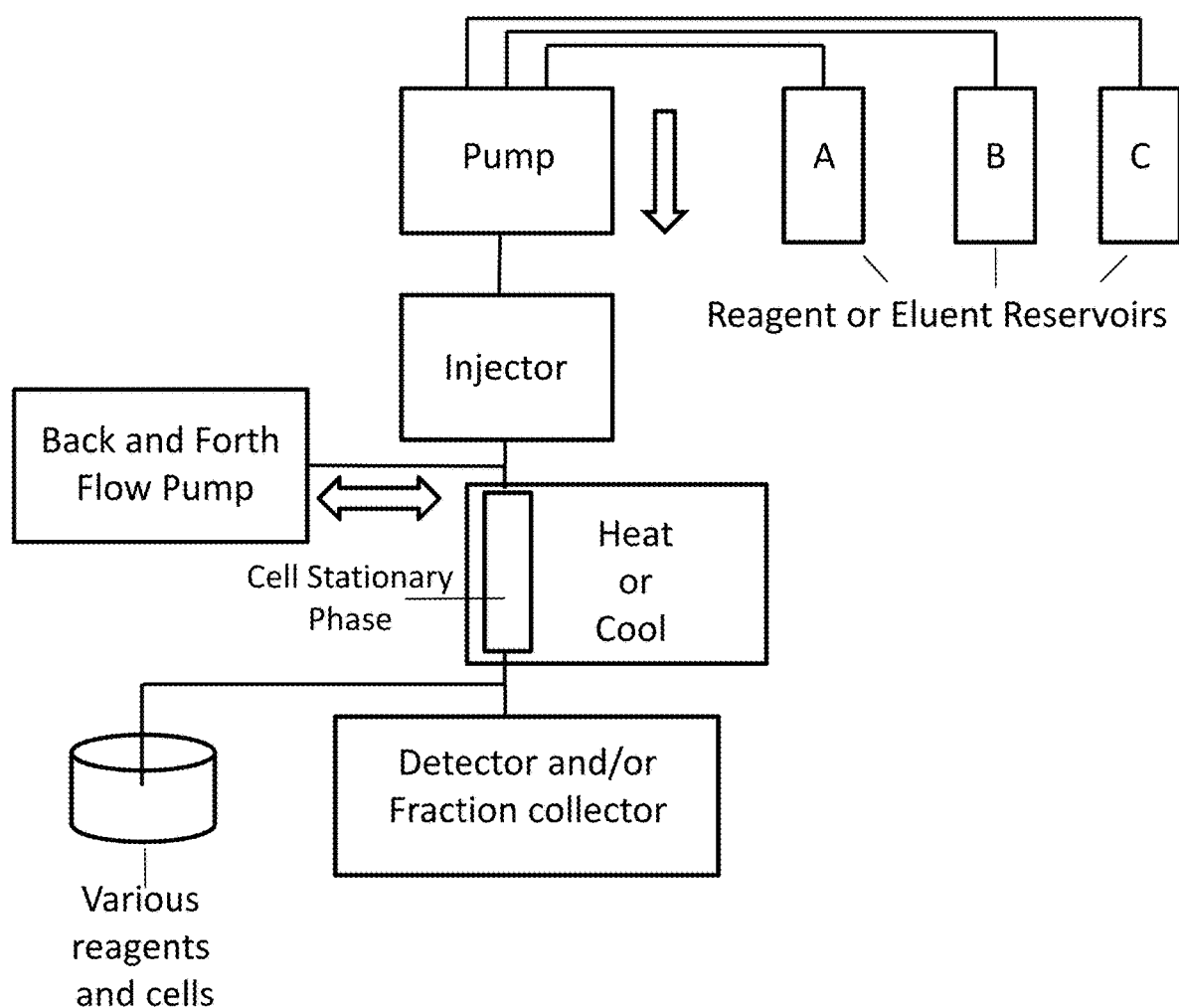
FIG. 12 is a depiction of a unidirectional flow column liquid chromatograph with a cell stationary phase column that operates using unidirectional flow. This instrument also contains a bidirectional flow pump for loading the cells onto the stationary phase. The instrument can be used for cell purification and diagnostic applications and cell stationary phase applications.

A more general instrument where unidirectional flow and bidirectional flow is used is shown in FIG. 12. The instrument may be used for cell purification, cell diagnostics or cell stationary phase chromatography.

The instrument is fully automated with a flow path of eluent reservoirs, pump, injector, living cell stationary column with optional column temperature control, detector and optional fraction or effluent collector. The pump may be a piston, peristaltic, air or gas pressure or syringe type pump. In some embodiments, there are two 3-way valves located at the column inlet and exit in order to optionally incorporate bidirectional flow through the column. Cells may be loaded onto the column and purified in this manner. The liquid chromatography instrument may be used for purification and recovery of cells either with cell sample injected into the column with the injector or loaded using back and forth flow. The cells may be eluted and recovered from the column and detected by changing the eluent pumped through the column. The liquid chromatography system is very useful for studying the differential interactions of analytes with the cell-based solid phase.

The chromatographic purification procedure may include combinations of unidirectional flow and bidirectional flow. For example, in the procedures described above, the cells may be loaded or captured by the column with back and forth flow and then the rest of the procedure performed with unidirectional flow.

In this configuration, not only is the column compatible with the cells so that they are not harmed, the tubing, tubing connections, valves, flow detectors and fraction collector are all cell compatible so that the cells are not harmed. This includes making certain the flow path does not contain any sharp edges or surfaces that may puncture the cell wall. In addition, the flow path does not contain chemicals such as metal oxides that may chemically harm cells or adsorb cells.

The liquid chromatograph may optionally include temperature control of the sample that is captured, fluid that is pumped through the column and/or the column. Fluid may be pumped through the column to provide nutrients and preserving the cells of the stationary phase column. The fluid may contain glycerol and other material to slow metabolism to preserve the cells of the stationary phase column. The temperature may be lowered to preserve the cells of the stationary phase column.

Detection may be continuous or fractions may be collected and analyzed. Analyte measurements include retention time, capacity factor, selectivity coefficient, breakthrough curve parameters. Examples of detectors include cell flow cytometer, UV and fluorescent, refractive index, chemiluminescence, electrochemical detectors, PCR or other nucleic acid measuring detector, and mass spectrometer detector.

Applications of cell-based stationary phase liquid chromatography include drug discovery, drug development (including personal drug development) and cell research. In drug discovery, the interaction of a library of compounds may be studied for a particular type of cell. In drug development, the interaction of a particular drug candidate, class of drug candidates, or analogs of a drug candidate may be studied. In cell research, the interaction of a compound with a particular cell or component of a cell may be measured and studied.

Measurement of Analytes and Cells in Cell Stationary Phase Liquid Chromatography Partitioning, gradient and displacement chromatography with a cell stationary phase may require the presence of competing entities to interact with the cell stationary phase. In the case of an antibody analyte interacting with the marker on the cell surface of a stationary phase, the eluent may contain another antibody or fragment of an antibody or a protein that has an affinity for a cell marker.

Displacement chromatography and frontal/breakthrough chromatography may be performed with or without a competing entity. Frontal chromatography is usually performed with unidirectional flow. These types of chromatography may be performed at different mobile phase ionic strengths, with different buffers and at a different pH to determine the extent of interaction of the analyte with the stationary phase.

Analytes may be small molecules or metabolic materials. These analyte materials may have rapid and reversible interactions with the stationary phase. In these cases, partitioning, gradient, step gradient, displacement or frontal chromatography may be performed. In other cases, the interactions of the small molecule or metabolic materials may be slow and even difficult to reverse. Competitive mobile eluents, having different mobile phase ionic strengths, with different buffers may be used to determine the extent of interaction of an analyte with the cell-based stationary phase.

It is possible to study how analyte libraries interact with cells for drug discovery, drug treatment or drug development.

Both the mobile phase analytes and the stationary phase functional group(s) can be analyzed and measured in this type of chromatography. No previously-described chromatography systems have this capability. Using the system, the interaction between analyte materials introduced into the cell-based stationary phase and the cells themselves can be characterized. For both the analyte and the cells, it is possible to determine whether or not there was an interaction and the extent to which the materials interacted. This examination can determine which material or materials interacted with the stationary phase, the manner in which they interacted, the extent of interaction (or non-interaction), which part of the cell stationary cell the material(s) interacted with and/or the effect of the interaction. This information can be exploited for a variety of downstream applications.

Stationary phase cells can be examined after they are used as a stationary phase. This examination is another means to determine the interaction of materials with a cell.

For example, a cancer cell stationary phase can be used to measure antibody interaction. The antibody may contain another material such as a toxin. The toxin can be delivered to the cell surface or into the cell.

Another example is a stationary phase comprised of bacterial cells used to examine antibacterial agent interaction and outcome.

Another example would be a stationary phase of epithelial cells in which cell signaling materials are used to measure interaction. After exposure to an analyte, the cell could be removed from the column and analyzed.

The interaction of an analyte with a cell may be measured by any type of chromatography. The ability to take up an analyte can be measured. Then, after optional removal of the analyte, the cells that make up the stationary phase may be examined to study the interaction.

After chromatography is performed, cells can be removed from the stationary phase and examined to see if they remain alive or are dead. In some embodiments, cell viability can be determined on column. Stains can be introduced to determine cell viability. The dead cells can be measured individually or together to determine if a reagent remains bound to the cells. The relative number or percentage of dead cells and live cells may be measured. The extent of damage to the cell membrane of a dead cell may be measured optically. A dye can be added that will only enter the cell if it is living. A nonlimiting list of dyes includes safranin, Eosin, propidium, Congo red, erythrocin, trypan blue, nigrosine, and Alcian blue. The ratio of dead cells and live cells may be measured as a function of time after exposure to a material.

Components, such as DNA, RNA, organelles, proteins, lipids, carbohydrates, etc. of the dead cells may be examined to determine the cause of the cells changing characteristics or dying. For example, the cell may be examined to determine if a reagent or portion of the reagent is associated with the cells and if the cells are alive or dead.

The treatment and manipulation of the cells must be gentle, both physical treatment and chemical treatment. Normal physical and chemical manipulation of a cell can cause damage to a cell and cause the cell to die. Measurements of cells loaded onto a resin to make a stationary phase but not used as a stationary phase is considered to be a background killing of cells which can serve as a control. These cells are not measured or their measurement is subtracted from the measurement signal.

These steps can be used for making and using a cell-based stationary phase.
1. Load or pack column with base resin beads.
2. Load column with an antibody or cell binding reagent.
3. Load column with cells. (In some embodiments, attach the cells to the beads and then pack the beads into the column.)
4. Expose column to a material with injection, block treatment, or breakthrough treatment and optionally measure interaction of the material with the cell stationary phase.
5. Optionally, wash the column.
6. Optionally, remove the cells from the column.
7. Analyze the cells for specific properties or characteristics.

Cell Stationary Phases with Controlled Mobile Phase Concentration

Impervious resin may also be used for cell purification. Since antibodies and other affinity reagents that are used to functionalize the resin do not enter the matrix of the bead but are only in the interstitial space and channels of the column, then the concentration of the reagents is effectively much higher when they enter and travel through the column. They are not diluted by that volume of liquid that is within the resin matrix. Higher concentrations of the antibody, aptamer and other reagents is useful because less reagent will be needed to functionalize the resin and the conditions needed to functionalize the resin will be lower. A higher concentration of reagents can make it possible to drive equilibrium reactions to completion.

Cell stationary phase columns can be based on substrates that are swollen with water. These include agarose, Sepharose, dextran, cellulose and other hydrophilic polymers that swell with water. When reagents are introduced or pumped through columns containing these substrates, cells if present will travel to the surface. Cells may not be able to enter the stationary phase matrix because the pores may not be large enough. However, water molecules, buffer molecules and other small size reagents may enter the pores of the resin substrate. Reagents such as aptamers, antibodies, Fabs, and other affinity reagents may enter the stationary phase matrix.

This phenomenon can make it difficult to control of the chemical environment surrounding the cells. Reagents can be concentrated if they do not enter the pores of the substrate while reagents that enter the pore may become diluted. In any case, the concentration of any particular reagent after it enters the column and as it travels down the column is unknown and unpredictable. But it is important to determine the concentration of the reagents in order to practice chromatography in the most predictable manner.

In some embodiments of the invention, the substrate used to contain the cell stationary phase is solid and impervious. Water and buffers do not enter the stationary phase matrix. Examples of this are impervious silica and zirconia and other inorganic materials, solid impervious polystyrene and other polymers. With these materials, the reagents and cells do not enter the matrix or interior of the bead when the bead is exposed to reagents and cells. But rather they reside in the space between the beads or in the interstitial space of the media and channels or they reside on the surface of the media. The concentration of the reagents only changes if they react with the affinity phase and are not diluted or concentrated by water or reagents entering the stationary phase matrix.

In certain embodiments, an impervious resin is utilized. The reduction in non-useable surface area will decrease reagent costs and the rigid structure will facilitate an easier packing procedure. This is shown in Example 18 which describes the synthesis of $E.\ coli$ with water-swollen agarose stationary phase and an impervious silica cell stationary phase. Impervious resins can be used for the capture and recovery of cells as well as for cell-based stationary phase liquid chromatography.

Technology and Methods Using Internal and External Standard Columns

The shape of a chromatography breakthrough curve, displacement curve or peak will depend on mechanical aspects of the columns as well as the kinetic interaction of the analyte with the stationary phase.

The effects of multipath diffusion through the column bed and frits, axial diffusion along the length of the column and kinetic interaction of the analyte and competing materials with the stationary phase all contribute to the shape of the curves. In some embodiments, internal and external standard columns can be used to measure the contributions of multipath diffusion and axial diffusion. As a result, kinetic interactions can be more easily compared and quantified.

The shape of a peak or frontal curve flowing through a column will depend on three general factors: the column multipath diffusion through the column bed and frits, axial diffusion along the length of the column and kinetic interaction of the analyte and competing materials with the stationary phase. This can be shown by the equation $S=A+(B/F)+CF$ where S denotes the sharpness of the chromatographic peak or breakthrough curve, A denotes multipath diffusion, B denotes axial diffusion, C denotes the rates of kinetic interaction and F denotes the mobile phase linear velocity.

The kinetic rates of interaction, the C term, of analytes and competitive materials with the living cells are of interest. In the case of frontal chromatography, the position and shape of the breakthrough will give information on the kinetic interaction and selectivity of the analyte for the chromatographic column. The same is true for displacement and partitioning chromatography. The kinetic interaction and selectivity will change depending on the presence, type and concentration of competitive components in the mobile phase. It can be difficult to quantify these rates when the rates of multipath diffusion (the A term) and axial diffusion (the B term) are unknown. The dead volume and packing of the column as well as the tubing connections and many other variables affect the shape of the breakthrough curve. It can be difficult to quantify the contribution of each of these variables. It can also be difficult to measure the differences in kinetic rates of interaction of multiple analytes and other competitive materials with the living cells.

Internal Standard Column System

An internal standard can be used to determine the A term and B term effects. In some embodiments, the column can contain sites that have rapid interaction kinetics in addition to the cell stationary phase. In other embodiments, a solution that does not interact with the stationary phase can be passed through the column as an internal standard. Since the beads are packed into the same column hardware, the dead volume, packing, frit, connections, and all parameters that contribute multipath dispersion and axial dispersion are the same or similar to the living cell column. Once the A and B terms have been determined, their effects can be subtracted, allowing determination of the kinetic rate of interactions of analytes with the cell-based stationary phase.

For example, a column could possess both ion exchange sites and a cell-based stationary phase. In this situation, the same column can be used to generate two data sets (e.g. an ion exchange breakthrough curve, displacement curve or chromatographic peak), one data set from interaction of a first analyte with the ion exchange sites and the second data set from interaction of a second analyte or analytes with the living cell stationary phase. The additional ion exchange sites have relatively rapid kinetics of interaction, term C, but would have similar multipath diffusion, term A and axial diffusion, term B. Differences in shape of the curves can be attributed to kinetic interactions of analytes with the cell stationary phase.

Columns having an internal standard must be designed carefully. In some embodiments, these columns possess a dual stationary phase. The dual stationary phase can be created using any group or site that has rapid interaction kinetics. Examples include ion exchange sites, normal phase, reverse phase or hydrophobic interaction sites. In these embodiments, an additional analyte that binds these rapid interaction sites is passed through the column. This additional (internal standard) analyte can be passed through the column prior to loading the analyte(s) intended to interact with the cell-based stationary phase. In some cases, the internal standard analyte can be passed through the column simultaneously.

In other embodiments, a solution having no interaction with the stationary phase can be used as an internal standard. In these embodiments, the standard should be chosen carefully to mimic the analyte(s) without interaction or interfering with the cell stationary phase. Parameters to be considered in choosing the standard include size, shape, charge, polarity. The standard could be comprised of protein, nucleic acid, lipids, carbohydrates other biological molecules, non-ionic molecules, salts, acids, bases, solid particles, polymeric particles, etc.

With the use of an internal standard, the breakthrough curve, displacement curve or peak can be determined and the effects of the column hardware and packing can be quantified. Then, curves or peaks of analytes interacting with the living cells can be quantified and compared and distinguished from the column hardware, packing multipath dispersion and axial diffusion.

External Standard

In another embodiment, an additional, external standard column is used to measure interaction differences. Two columns are packed with identical column hardware, fluid connections, bead substrate, etc. In one example, the two columns are identical in all ways.

A salt or molecule is chosen that does not interact with the stationary phase substrate or functional groups. A frontal, displacement breakthrough or a peak chromatography can be performed with this column to determine the diffusion terms, B and A. A breakthrough curve, displacement curve or chromatography peak curve with the second living cell stationary phase column is compared to the first column to determine the effect of the kinetic interactions, term C, with the column. Additional living column experiments can be performed to study the relative interaction rates of different analytes and competitive materials.

In another example, a functional group is chosen for the reference external standard column that has rapid kinetic interactions, term C. A salt or molecular solution is pumped through the column, terms A and B are measured and compared to the living cell stationary phase column.

Drug Development

The cell-based stationary phase can be used for drug development applications. In some embodiments, cells can be immobilized on a column and then challenged with different entities such as libraries or pools of molecules (e.g., small molecule drug leads or biologics). In other embodiments, cells can be immobilized on a column and the interaction with other cells can be examined. Conversely, drug candidates can be immobilized on the column and challenged with different cell types.

In one example, a library of small molecule drug candidates labeled for identification can be exposed to cells immobilized on a column. A wash step can be performed and the cells can be eluted from the column. Those cells that have a drug candidate bound can be identified. Mass spectrometry can be used to identify the drug candidate and its target on the cell.

A number of techniques can be used to screen for potential drug leads. As mentioned previously, target cells can be immobilized on a column. When done in multiplex, multiple cell-immobilized columns can be screened in parallel. Capture or treatment experiments may be performed in parallel with two or more columns up to 96 columns. Examples of parallel experiments include a control or reference sample side-by-side with cells that have undergone different treatments or are from different sources. In another example, bacteria can undergo parallel treatment with antibiotics/drugs or simultaneous treatment with multiple drugs, either before loading or after capture by the column. A single type of drug per column or a combination of drugs directed to cells on a column may be studied.

Multiplex operation can be performed with between 2 and 1536 columns simultaneously. Each column can be subjected to a different drug lead to screen for the desired cell interaction or signaling event.

The following techniques can be used.

1. Eluting the cells and performing qPCR (e.g., to measure a change in gene expression or particular mRNA). For example, expression of genes involved in programmed cell death could be measured.
2. Use cells transfected with a reporter gene such as GFP or luciferase. The reporter gene would be engineered with a promoter region corresponding to the desired cellular event. If the promoter is induced by a drug lead, the cell would express the reporter. Detection of the reporter gene expression can be performed on column or after cells are eluted from the column. As an example, differentiation of stem cells could be measure with a reporter gene.
3. If the drug is designed to induce a regenerative cellular event, cell growth and doubling can be monitored as the final assay. Cells could be eluted and grown in cell culture.

In one example, cells having a known drug target could be used to identify potential drug as follows.

Put cells having a validated target on the column.

Challenge the cells on the column with library of fluorescently-labeled drug candidates.

Wash

Elute cells

Count/separate the labeled cells in a cell sorter.

Analyze cells or components of cells by mass spectrometry by LC/MS, MALDI, etc.

As an alternative to fluorescent labels, drug candidates could be labeled with DNA barcodes. PCR could then be used to identify particular candidates able to bind cells.

In another example, an unlabeled library can be used and drug candidates can be identified using a cell viability assay.
  Put cells having a validated target on the column
  Challenge with library of drug candidates
  Wash
  Add live/dead cell stain on column
  Wash
  Elute cells
Alternatively, the cells can be stained after elution. The results could be evaluated using fluorescence microscopy or flow cytometry. A column in which the cells were not challenged with the drug candidate could serve as a negative control.

A variety of detection methods can be applied to the methods described herein. Non-limiting examples follow.
  cell sorter or flow cytometry
  fluorescence microscopy
  light microscopy (e.g., to examine cell capture, viability or morphology)
  mass spectrometry
  PCR
  sequencing
  On-column or in-line detection
  electrophoresis In another example it may be desirable to investigate the response of different cell types to a drug. For example, a known cancer drug effective on one cell type may also bind to or be effective against another cell type. The following experiment could be performed.
  Attach labelled drug to the column (or could attach cells)
  Add cancer cells of a different type
  Wash
  Elute
  Count/separate labelled cells in cell sorter As mentioned above, partitioning may be useful in some instances. For example, partitioning can be used to distinguish between several promising drug candidates, all of which bind the cells with relatively low affinity.
  Immobilize cells on a column
  Add mixture of several labelled drug candidates
  Collect fractions or use in-line detection In this experiment, the relative binding efficacy of each drug candidate is determined by its elution order. This technique can also be used to characterize the relative binding efficacy of different monoclonal antibodies. Cells can be immobilized on the column and challenged with different monoclonal antibodies. In some embodiments, a known drug might be tweaked for instance by mutagenesis or synthesis. The relative binding of different drug analogues could then be investigated using partitioning.

In another embodiment, the following experiment could be performed to simultaneously identify drug targets and drug leads.
  1. Immobilize cell of choice on column
  2. Screen DNA bar-coded small molecule drug libraries, antibodies or antibody derivatives
  3. Present drug libraries to cell-immobilized columns
  4. For a negative control, do not present drug libraries
  5. Wash
  6. Release negative control cells and cells in complex with drug leads
  7. Disrupt negative control cells and cells in complex with drug leads to generate membrane fragments consisting of cell-surface proteins and cell surface proteins bound to drug leads
  8. Run non-denaturing gels of negative control membrane fractions and experimental membrane fractions.
  9. Identify, through gel shift, membrane protein-drug complexes.
  10. Extract leads and use mass spec to identify membrane protein and drug lead.

In certain embodiments, cells can be immobilized on the column and displacement chromatography can be used. For example, it may be desirable to compete off a naturally-occurring ligand with a drug for a pathway blocking drug application.

Breakthrough or frontal chromatography can be used in some instances, particularly for drug maturation studies. Breakthrough curves such as the one shown in FIG. 9 can aid in identifying entities having the desired binding kinetics, regardless of whether they're fast or slow. Several drug candidates or analogues can be compared in this manner.

The use of columns is advantageous for sequential additions of different molecules or compounds. For example, to examine calcium-dependent interactions, calcium could be added to the cells immobilized on a column, followed by the addition of a library.

Liquid-Sealed Chromatographic System

The sealed chromatographic system is a liquid chromatography column that operates without exposure to ambient conditions. Once sealed, the components of the chromatographic device and liquids within the device cannot be contaminated by materials outside the sealed system. Ambient conditions are defined herein as the conditions of the surrounding environment. The sample, wash and elution solutions are passed through the column in a closed environment. The column can be sterile and can be used to isolate cells or enrich cells in a sterile environment. The column itself and the solutions passed through the column can be sterile. The entire chromatographic process is performed under sealed or closed conditions including sample loading onto the column, column washing, and column elution. The purified product is recovered in a closed receiving container. The sealed format prevents contaminants from entering the system. The system may contain one or more vents or check valves. However, the vents must operate in a way that materials may only leave the system and not enter the system. Examples of vents may include check valves that only let material out, or a 0.2-micron filter that lets gases leave or enter but does not let bacteria or other contaminants enter the system.

As with other embodiments described herein, cells can be captured using affinity, hydrophobic interaction, reverse phase, normal phase, ion pairing, ion exchange or other strategies. Alternatively, an enrichment can be performed in which the desired cell types pass through the column while other non-desired materials are retained.

Liquids flow from a feed bag or reservoir to a receiving bag/reservoir. Flow through the column can be bidirectional or unidirectional. Bidirectional or back and forth flow can optionally be used for any or all of the equilibration, capture, wash and elute processes. The sealed system does not contain flow restrictions or backpressure to flow that will restrict the flow of liquid with the pumps used by the system. Of course, restrictions that provide backpressure that stop or slow the flow are harmful. But even small restrictions to flow are harmful because they could make the flow through the system unpredictable and unreliable. A pump may appear to work with a sealed system, but changing a parameter such as the tubing, column or fitting may marginalize the system to render the sealed system unreliable. Sealing the inlet reservoir may allow the pump to work for a time period, but may stop working if a negative pressure develops preventing feed of the liquid into the pump.

Likewise, sealing the outlet reservoir may allow the pump to work for a time period, but may stop working if a positive pressure increases the resistance of flow out of the system.

Figure 14A:
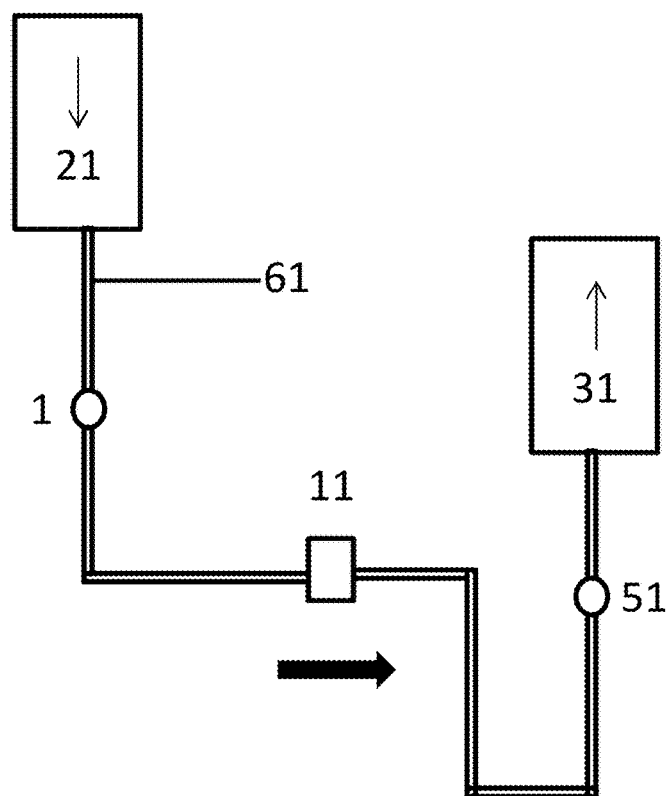
FIGS. 14A and 14B depict an embodiment of a closed column system for capture of cells with a back and forth flowing system.
Figure 14B:
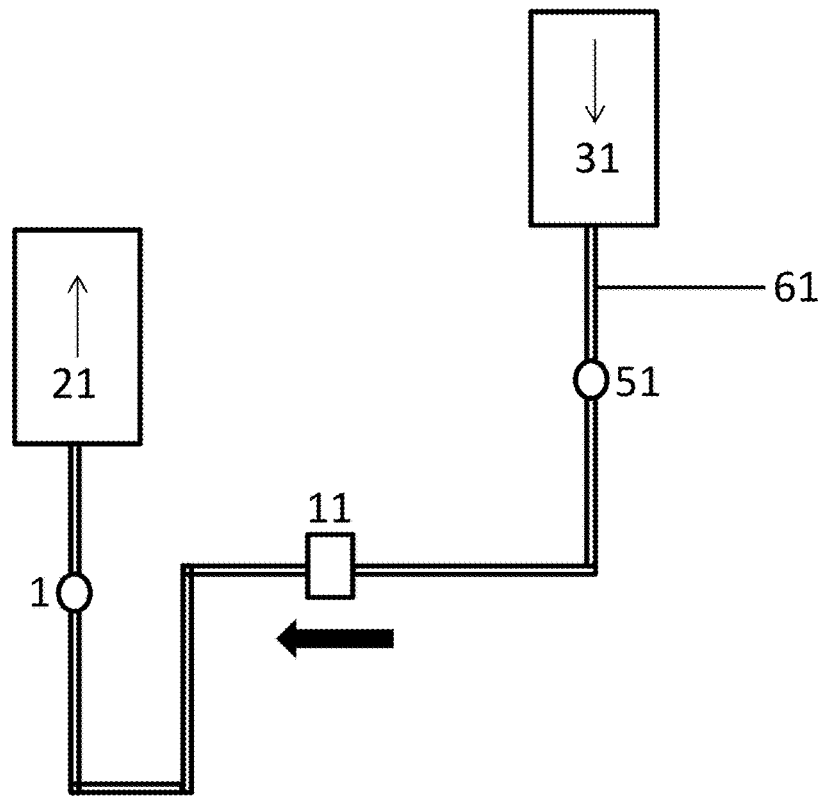

FIGS. 14A and 14B provide a stylized depiction of a sealed column system for cell capture with a back and forth flowing system. The flow is controlled by the relative differences in the height of the feed and receiving closed containers. The system contains column 11 and reservoirs, 21 and 31. Depending on the direction of flow, a given reservoir can either be a feed to column 11 or the reservoir can receive flow from column 11. In some embodiments, the sealed column system may also contain on/off valves 1 and 51 to allow flow or stop flow. Reservoirs 21 and 31 are connected to valves 1 and 51 and column 11 with flexible tubing 61.

The flow through column 11 can be controlled by several different options. In one method, the relative difference in height of feed and receiving sealed containers will apply a positive pressure on one side of the column and a negative pressure on the other side of the column. In FIG. 14A, reservoir 21 is positioned above column 11 and reservoir 31 is positioned lower than reservoir 21. This will cause flow from reservoir 21 through the column 11 and into reservoir 31 as depicted by the arrow below column 11. The flow rate can be increased by changing the relative position of the two reservoirs, for example by increasing the height of reservoir 21 or lowering reservoir 31. Reservoir 31 may be placed below column 11 or above the height of column 11.

Reversing the positions of the two reservoirs as shown in FIG. 14B will reverse the flow through column 11 as shown by the arrow going from right to left below the column. Flow will stop when the feed reservoir is depleted or the receiving reservoir is full.

In some embodiments, flow through sealed column 11 may be powered by peristaltic pumps. For example, valve 1 and/or 51 may be replaced with a peristaltic pump or pumps. When a peristaltic pump is used, the tubing can remain sealed. Flow through the sealed column may also be performed with syringe pumps. For example, reservoirs 21 and/or 31 can be replaced with syringe pumps. In this embodiment, feed and receiving chambers 21 and 31 remain sealed.

Figure 15A:
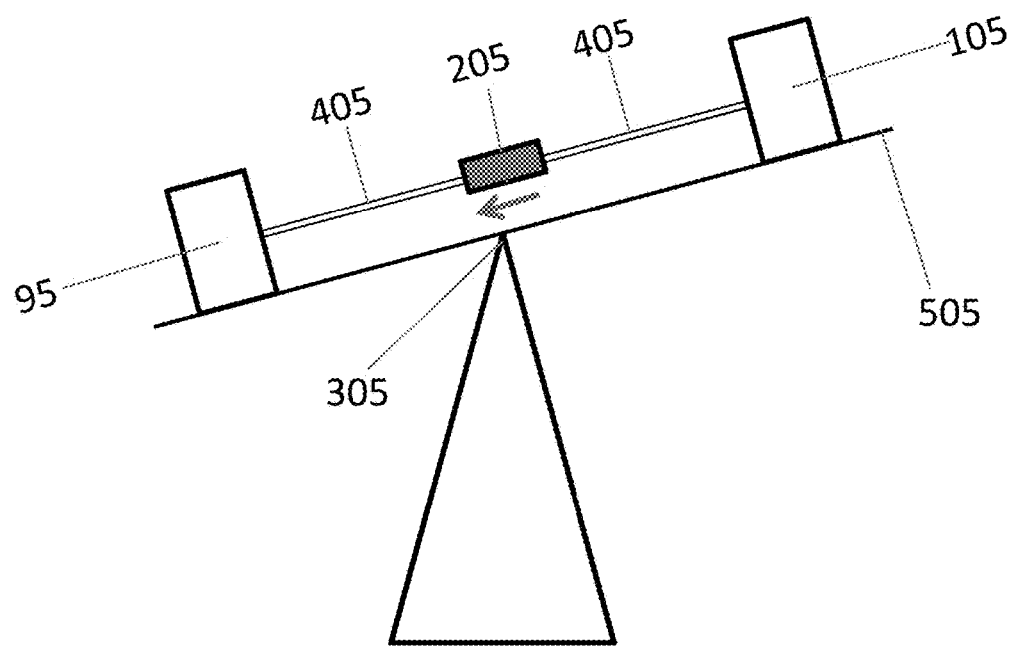
FIGS. 15A and 15B depict an embodiment of a closed column system for capture of cells with a back and forth flowing system with two each feed and receiving containers on each side of the column.
Figure 15B:
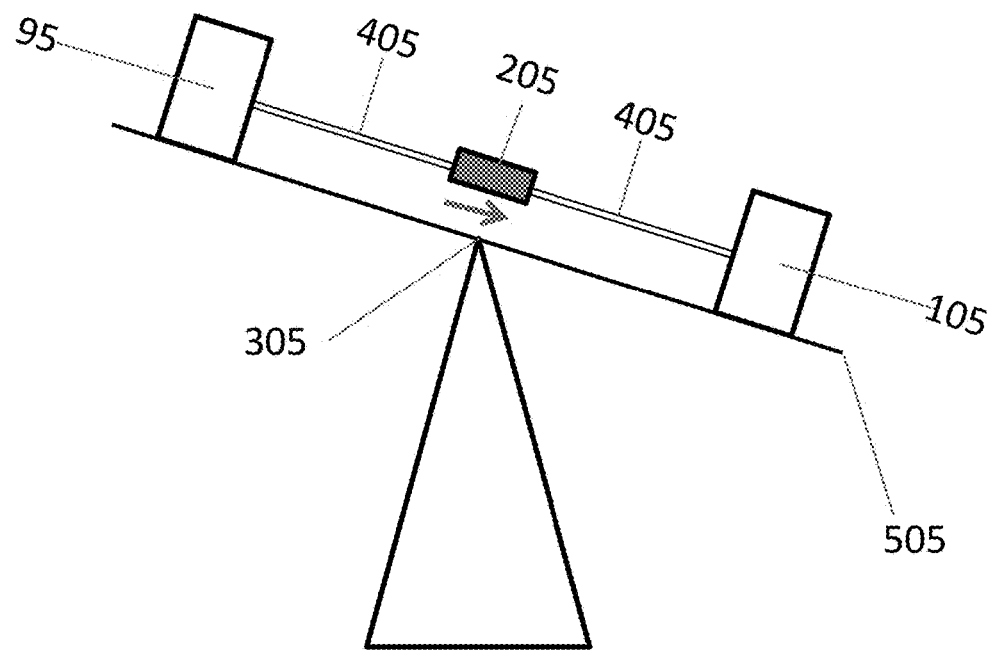

FIGS. 15A and 15B show stylized depiction of an alternate embodiment of a sealed column system for capture of cells with a back and forth flowing system. The system contains column 205 and reservoirs 95 and 105. Depending on the direction of flow, a given reservoir can either provide feed to column 205 or receive effluent flow from the column. The reservoirs are connected to the column through tubing which can be flexible sealed tubing. The flow through the column 205 is controlled by placing the reservoirs and column on platform 505 where fulcrum 305 is positioned at or near column 205. The reservoirs are raised and lowered relative to each other by tilting platform 505 at fulcrum 305.

The relative difference in height of the feed and receiving sealed containers will apply a positive pressure on one side of the column and negative pressure on the other side of the column. In some embodiments the positive pressure of the feed reservoir can be in the range of 5 psi, 4.5 psi, 4 psi, 3.5 psi, 3 psi, 2.5 psi, 2 psi, 1.5 psi, 1 psi, 0.5 psi, 0.25 psi, 0.1 psi, 0.01 psi or 0.001 psi. Likewise, the pressure in the receiving reservoir can be in the same range, however it is also possible for the pressure of in the receiving reservoir to be 0. Flow will stop when the feed reservoir is depleted or the receiving reservoir is full.

Figure 16A:
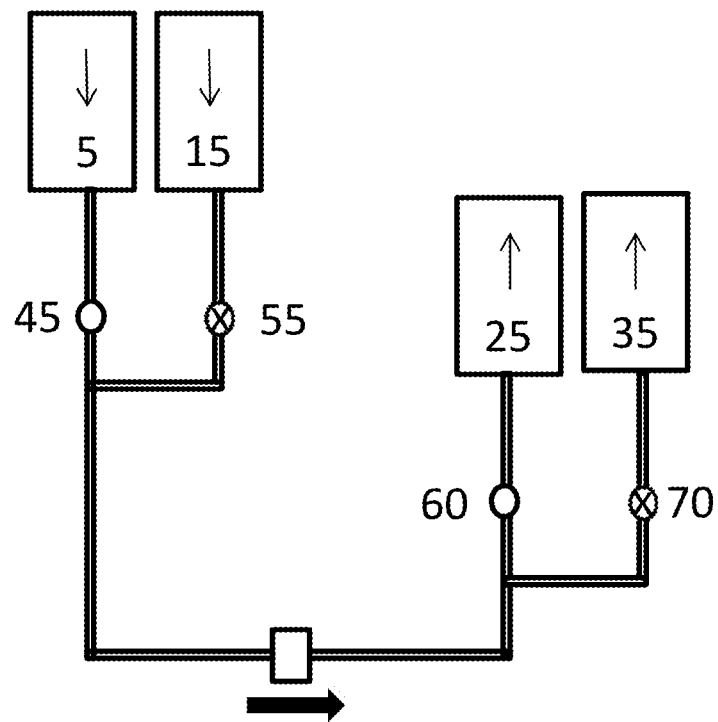
FIGS. 16A and 16B depict an embodiment of a closed chromatography column system for capture of cells with a back and forth flowing system with two each feed and receiving containers on each side of two optionally closed system columns.
Figure 16B:
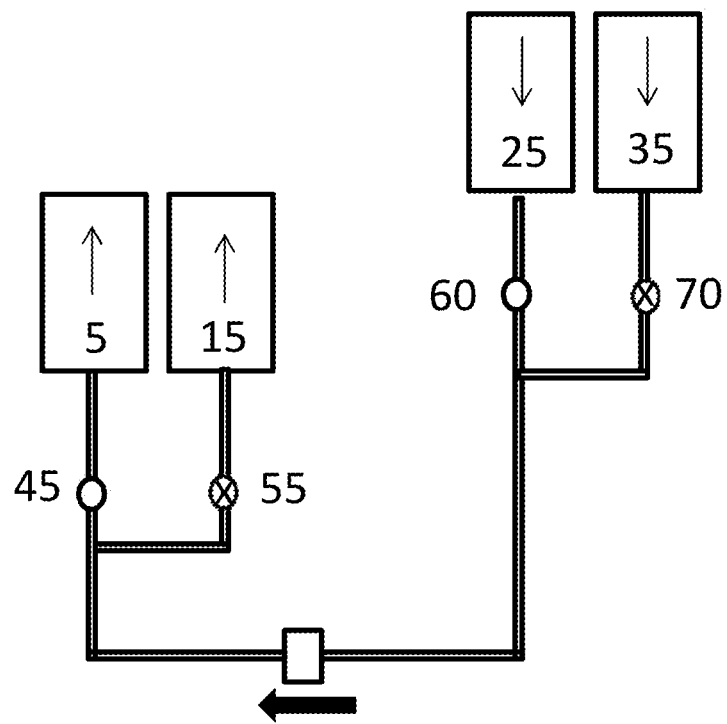
Figure 17A:
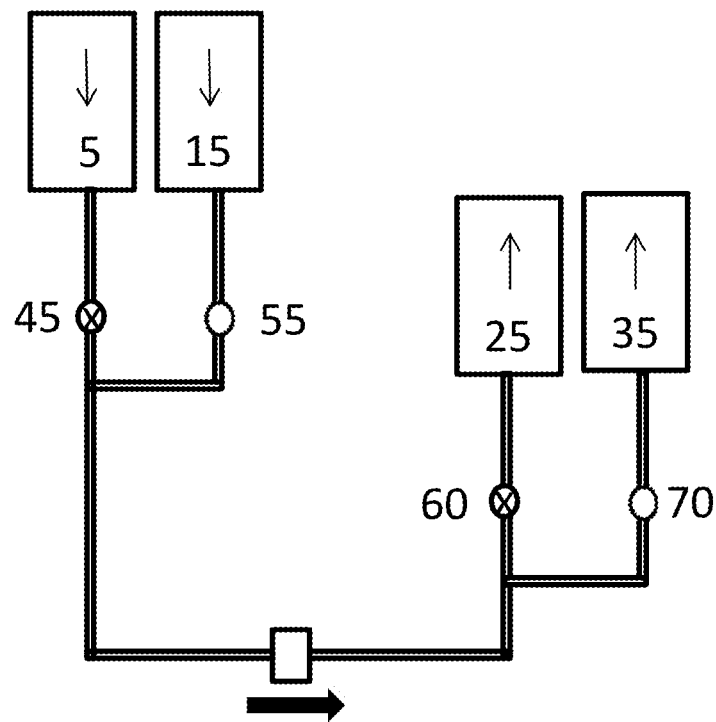
FIGS. 17A and 17B depict an embodiment of a closed chromatography column system for capture of cells with a back and forth flowing system with two each feed and receiving containers on each side of two optionally closed system columns.
Figure 17B:
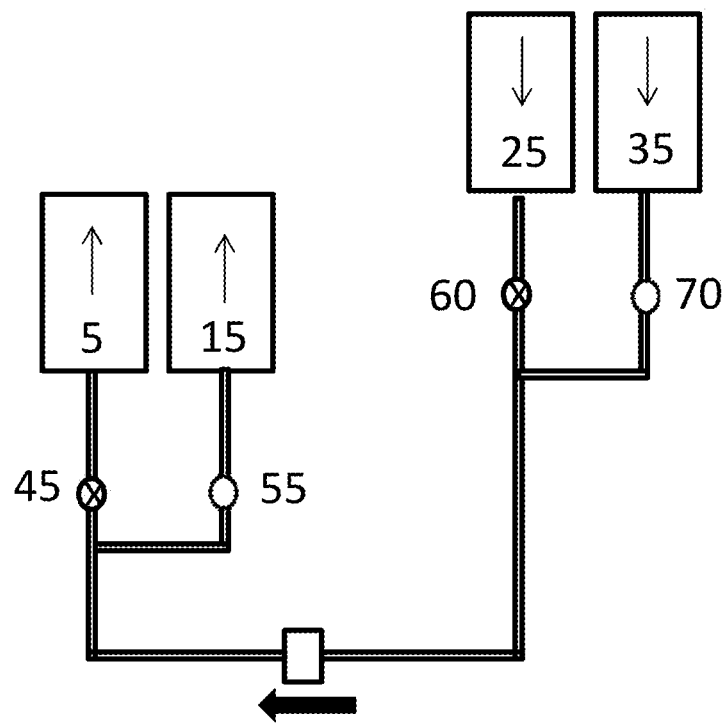

FIGS. 16A and 16B depict a sealed column system for capture of cells with a back and forth flowing system with two feed containers and two receiving containers on each side of the column. The on/off valves control the flow into and out of a particular container. In FIGS. 16A and 16B, valves 55 and 70 are closed and flow is between closed containers 15 and 35. FIGS. 17A and 17B depict the same system architecture in an alternate configuration in which valves 55 and 70 are open while valves 45 and 60 are closed.

Figure 18:
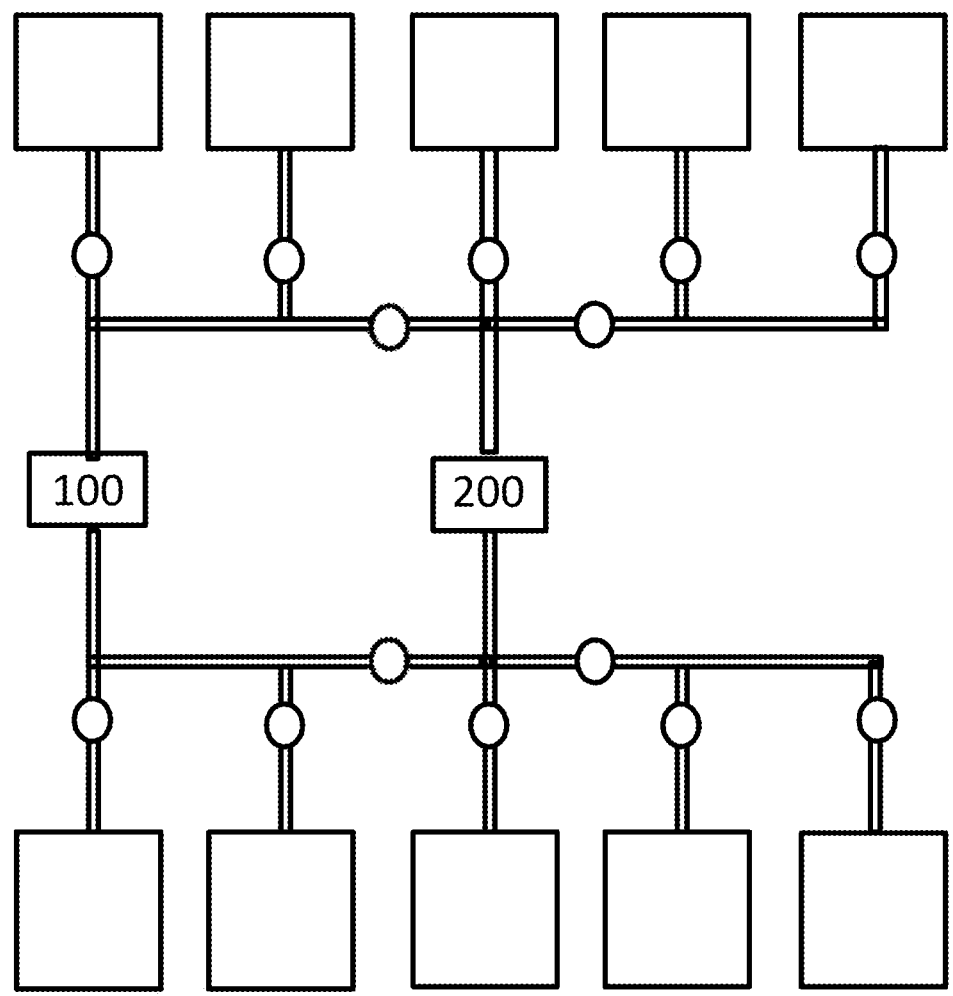
FIG. 18 depicts an alternative configuration of a sealed liquid chromatography column system for capturing cells using a flowing system with five each feed and receiving containers. The system may be used with unidirectional flow or back and forth flow. The pumping system may be gravity, pressure, vacuum, or peristaltic pumping.

FIG. 18 depicts an alternative configuration of a sealed liquid chromatography column system for capturing cells using a flowing system with five each feed and receiving containers. The system may be used in unidirectional flow or back and forth flow. The pumping system may be gravity, pressure, vacuum, or peristaltic pumping. In this configuration, there are two columns 100 and 200. Column 200 has five feed containers and five receiving containers on each side of the column. The on/off valves control the feed and receiving container that is in use and the particular column that is used as described in FIGS. 15A and 15B. A specified purification, washing and recovery method uses a controlled sequence of valves (pictured as small ovals) opening and closing. Second column 100 gives the option of using a second chemical treatment on purified and recovered cells from column 200. The sealed chromatography system is described in more detail below in Example 22.

In some embodiments, a manifold can be used to introduce other liquid into the column in a sealed system including wash and elution solutions. A third bag or container can be configured to receive purified cells. A second column can be configured to clean the purified cells for materials including antibodies, biotin, etc. with the cells received into a fourth container. In some embodiments, the system can be used to remove cancer cells or pathogens from blood. In all cases, back and forth flow can be used if necessary to achieve a complete reaction processes.

Figure 22:
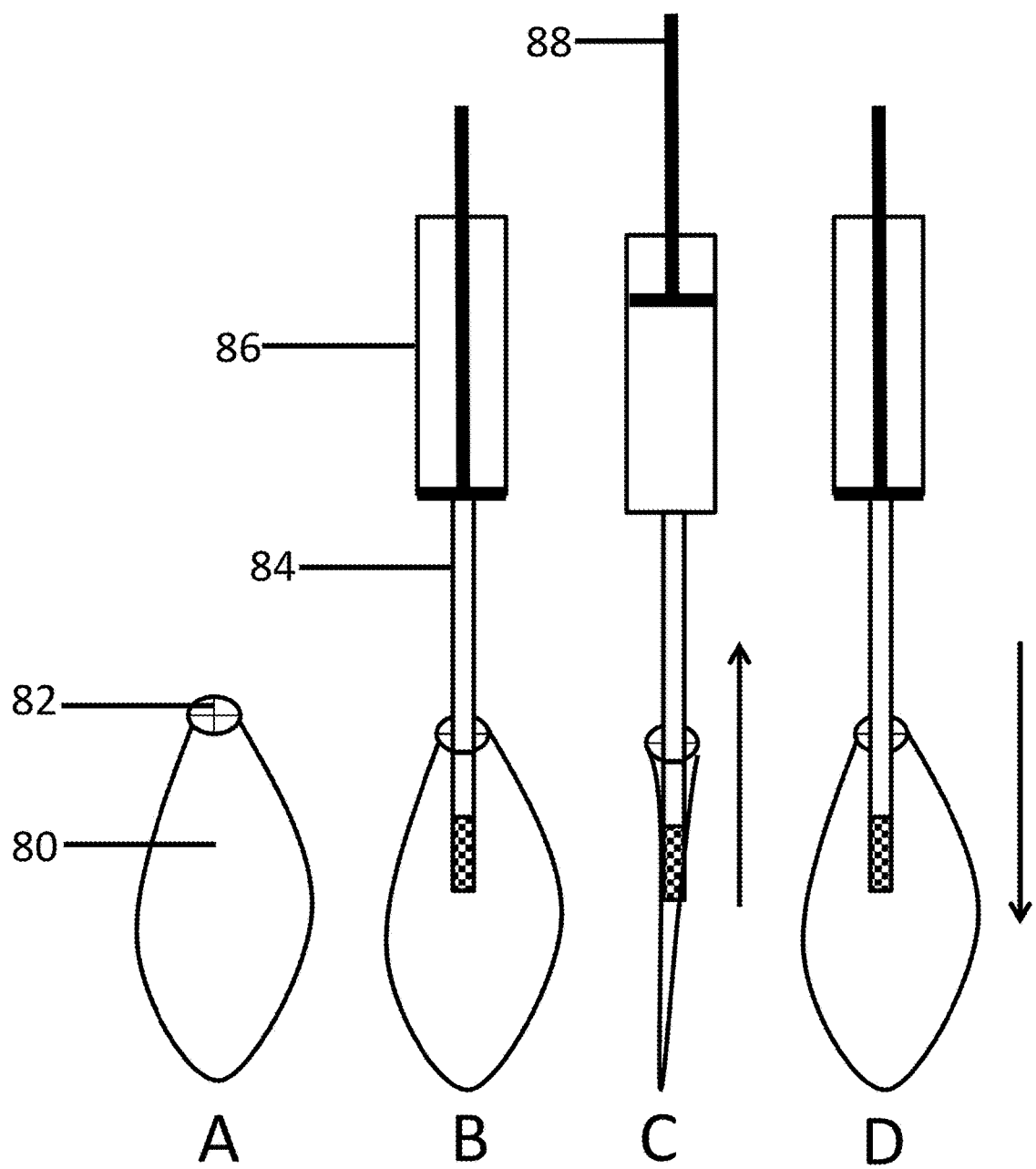
FIG. 22 is a depiction of a sealed chamber with a column and a pump.

FIG. 22 shows an embodiment of a sealed chamber with a column and pump. Sealed chamber 80 contains a liquid which may be a sample, a wash solution, an eluent or another solution. Seal 82 at the top of chamber is comprised of a soft or flexible material into which a column or tubing may be inserted.

Examples of suitable materials include silicone, rubber, neoprene, poly olefins, PVC, polypropylene, polyethylene, Teflon, polyurethane, nylon, polystyrene and any other flexible polymer or material. In step B, column 84 engaged with pump 86 is inserted through seal 82 into chamber 80. The entire flow path is sealed including chamber 80, column 84 and pump 86.

As plunger 88 is retracted in step C, the liquid is pulled from chamber 80 through column 84. Depending on the pump type, the liquid can be pulled all the way into pump 86. The system remains sealed. In step D, plunger 88 is pushed down and the liquid is expelled from pump 86 (if present), column 84 and back into chamber 80. The volume of chamber 80 expands again and the system remains sealed. The steps can be summarized as follows.

A. A sealed chamber contains a liquid. The seal at the top may be silicone or another soft material into which a column or tubing may be inserted.

B. A column with pump is inserted into the chamber. The entire flow path is sealed including the chamber, column and pump.

C. The plunger is retracted pulling the liquid through the column and possibly into the pump. In some embodiments, the pump is a syringe. In these embodiments, the volume within the pump becomes greater as the plunger/piston is retracted. The chamber contracts. The system remains sealed.

D. The plunger is pushed down moving the liquid through the column and into the chamber. In some embodiments, the pump contracts (not shown).

Pressures applied to a sealed chromatography system column and reservoirs are complex. The separation column has an additional backpressure or resistance to flow force exerted upon it. This is due to the eluent flowing out of the column which is in direct fluid contact with the reservoir of fluid collected from the column. The backpressure will change depending on the relative volumes of liquid above and below the columns (inlet and outlets) and the positions of the inlet and outlet volumes. It is not possible to predict the pressures as they are variable. It is surprising that that flow of fluids can be initiated (in either direction), maintained and established with the column configuration and design constraints. It is also surprising that the capture, washing and recovery of cells can be accomplished with variable flow rates and variable pressures. It is also surprising that the process can be performed reproducibly and predictably (predictable purity, concentration and volume).

In the sealed system, resistance of liquid and cell flow through the column is caused not only by the column but also by the receiving container which is in intimate contact with the fluid. A positive pressure is needed to expand the receiving container as it is filled from the column effluent. There may also be a pressure pushing back against or resisting the flow caused by the receiving container attempting to contract rather than expand. This resistance to flow through the column is in addition of the liquid attempting to flow through the column and the cells themselves having a resistance of traversing the column. Thus, the positive force needed to pump the cells and liquid through the column must overcome all of these forces in a sealed system. The positive force pushing the liquid through the column will be variable and, if gravity is used, will become exceedingly small, as the amount of liquid on top of the column approaches zero force with depletion of the liquid above the column. Nevertheless, all of the liquid can be pumped through the column.

The pumping force for a sealed system can be any peristaltic pump, positive pressure pump, piston pump, diaphragm pump, negative pressure pump, syringe pump, pipette pump, or gravity pump. The pump may force the liquids to flow through the system in back and forth flow bidirectional modes, unidirectional flow modes, single pass unidirectional mode, circulating pass mode or combinations of these flow modes.

EXAMPLES

Example 1. Sperm is Captured, Separated from Cells and DNA Analysis is Performed In forensics, it is often desired to obtain DNA profiles from old stains, crime scene, body fluid samples and other possible samples. The primary goal is to preferentially separate sperm from vaginal cells and other materials, a necessity for DNA analysis in rape cases, for example.

DNA aptamers which are short strands of DNA were developed by SomaLogic (Boulder, Colo.) to bind sperm heads, and used to both identify and immobilize the sperm heads for purification and later DNA analysis. These aptamers are used in a column bed system of the invention with biotin and Streptavidin linkers to selectively capture sperm cells. The aptamer sequences bind preferentially to both the outer protein membrane and the stripped perinuclear calyx of sperm cells in the presence of non-sperm epithelial cells.

Sperm cells (research vials, prepared by density gradient centrifugation and subsequent washing) are purchased from California Cryobank. Washed sperm cells are prepared using three washes and suspension in a buffer supplemented with Triton X100 detergent and NaCl to final concentrations of 1% v/v and 600 mM HeLa cells to simulate non-sperm epithelial cells are added and the mixtures are incubated for ten minutes.

Cotton swabs are used to simulate capturing the sperm sample. The sample is removed from the cotton swab with a buffer. Aptamers with biotin linkers are added to the solution and incubated. After washing the sample, the mixture is passed through a streptavidin packed bed column of the invention. The sperm is captured and subsequently washed by passing wash buffer through the column.

The sperm is eluted from the column by passing a buffer through the column breaking up the aptamer/sperm column. Eluted aptamer DNA are purified and then amplified for DNA analysis.

Example 2. Antibody Purification of Sperm

This example uses antibodies rather than aptamers to capture sperm cells in the presence of other cells. A cocktail of antibodies specific to sperm cell surface antigens are anchored to Protein A affinity beads packed into a column of the invention. The specificity of antibody-antigen binding selectively captures sperm cells from samples that are comprised of a mixture of sperm cells, white blood cells, epithelial cells, cell lysates, etc. Alternatively, the antibodies are added to the sample mixture first and then captured by the column. After washing with a neutral buffer, the sperm cells are eluted with low pH or high pH buffers and the DNA is analyzed.

The antibodies may be tagged with His tags for example. In this case, IMAC beads may be packed into columns of the invention to capture the antibodies which are used in turn, to capture the sperm. In this case, the antibody sperm combination may be eluted, the cell lysed and the DNA analyzed. Other tags may be used such as FLAG-ANTIFLAG, etc.

Peptide tags are used for capture. These include AviTag, a peptide allowing biotinylating by the enzyme BirA so the protein can be isolated by streptavidin, Calmodulin-tag, a peptide bound by the protein calmodulin, FLAG-tag, a peptide recognized by an antibody, HA-tag, a peptide recognized by an antibody, Myc-tag, a short peptide recognized by an antibody, SBP-tag, a peptide which binds to streptavidin, Softag 1, for mammalian expression, Softag 3, for prokaryotic expression, V5 tag, a peptide recognized by an antibody, and Xpress tag. Nonlimiting examples of covalent tags tags include Isopeptag which binds covalently to pilin-C protein and SpyTag which binds covalently to SpyCatcher protein.

Protein tags include BCCP (biotin carboxyl carrier protein), a protein domain recognized by streptavidin, glutathione-S-transferase-tag, a protein which binds to immobilized glutathione, green fluorescent protein-tag, a protein which is spontaneously fluorescent and can be bound by nanobodies, maltose binding protein-tag, a protein which binds to amylose agarose, Nus-tag, Strep-tag, a peptide which binds to streptavidin or the modified streptavidin called Strep-Tactin and Thioredoxin-tag.

Example 3. Circulating Tumor Cells

A cancerous tumor sheds small numbers of tumorous cells into its immediate vasculature. These cells then make their way into the circulatory system, and are thus called circulating tumor cells (CTCs). CTC information is used cancer prognosis, therapy monitoring and metastasis research.

Circulating tumor cells (CTCs) are important targets for study to understand, diagnose, and treat cancers. However, CTCs are found in blood at extremely low concentrations which makes isolation, enrichment and characterization challenging. A typical concentration in a human cancer patient is approximately 1-100 CTCs per mL of blood.

CTC purification with the columns of the invention capture many or most of the CTCs in the blood sample (high capture efficiency) and are selective with very few other cells accidently isolated. The samples are processed with sufficient speed and without battering of the cells so that cells remain viable in many cases.

The columns of the invention operate by coating the column media with an antibody (anti-EpCAM) and then bonding the antibody to the epithelial adhesion molecules (EpCAM) of CTCs. After capture of anti-EpCAM labeled CTCs from a blood sample, CTC identification and enumeration are achieved using immunostaining.

During one experiment 2 to 80 spiked breast cancer cells are isolated from 1 mL of mice blood sample with 90% capture efficiency. A 200 µL bed column with a 1 mL pipette tip body is used for one experiment. Whole blood is processed through the column with bidirectional flow for 5 cycles at 200 µL/min flow rate. The column is washed with buffer and then the cells are eluted with 500 mM citric acid.

Example 4. Capture of Cells from Blood

The purification and analysis processes used in example 3 are used for other cell types including white blood cells, stem cells, T cells, B cells and others. In this example, the medium used can be capable of capturing each cell type. Alternatively, the medium may capture other sample components, thereby enriching for the desired cell type.

Example 5. Capture of Cells from Blood

The purification and analysis processes used in examples 3 and 4 are used except the pumping methods for flowing the fluids through the column are changed as follows.

The pumping method is bidirectional, unidirectional, gravity flow and gravity flow plus vacuum and/or pressure.

In addition, the method is performed with two different column configurations. In one configuration, there is an air gap above the column bed, while in the other configuration, there is no air gap above the column bed.

Example 6. Capture of Cells from Blood

The purification and analysis processes used in examples 3, 4 and 5 are used except the column has a bed volume of 1 mL inside a 10-mL pipette body. The flow rates are approximately 10 times faster with this column so samples sizes approximately 10 times greater are processed in approximately the same time.

In this example the cells are released from the column by enzymatic and chemical cleavage of the linker. The cells are collected and counted.

Example 7. Capture of Cells from Tissue

For tissue samples composed of different types of cells, heterogeneous cell populations will be present. To obtain as much information as possible about an individual cell type, biologists have developed ways of dissociating cells from tissues and separating the various types. A mild procedure is used to collect whole, intact cells. Homogenized cells are kept at low temperatures to prevent autolysis and kept in an isotonic solution to prevent osmotic damage.

The first step in isolating cells of a uniform type from a tissue that contains a mixture of cell types is to disrupt the extracellular matrix that holds the cells together. For example, viable dissociated cells are obtained from fetal or neonatal tissues. The tissue sample is treated with proteolytic enzymes (such as trypsin and collagenase) to digest proteins in the extracellular matrix and with agents (such as ethylenediaminetetraacetic acid, or EDTA) that bind, or chelate, the $Ca^{2+}$ on which cell-cell adhesion depends. The tissue can then be teased apart into single living cells by gentle agitation to make a cell suspension.

Columns of the inventions are loaded with antibodies that have an affinity for fetal cells. The suspension is passed with bidirectional flow through the column to capture the cells. After washing, the cells are released with by treatment with trypsin to digest the antibodies. The cells may be visually tagged by using an antibody coupled to a fluorescent dye to label specific cells.

Given appropriate surroundings, most plant and animal cells can live, multiply, and even express differentiated properties in a tissue-culture dish. The cells can be watched continuously under the microscope or analyzed biochemically, and the effects of adding or removing specific molecules, such as hormones or growth factors, can be explored. In addition, by mixing two cell types, the interactions between one cell type and another can be studied. Experiments performed on cultured cells are sometimes said to be carried out in vitro (literally, "in glass") to contrast them with experiments using intact organisms, which are said to be carried out in vivo (literally, "in the living organism"). These terms can be confusing, however, because they are often used in a very different sense by biochemists. In the biochemistry lab, in vitro refers to reactions carried out in a test tube in the absence of living cells, whereas in vivo refers to any reaction taking place inside a living cell (even cells that are growing in culture).

Example 8. Capture of Bacterial Cells

An *E. coli* culture is grown at 37° C. The *E. coli* strain is engineered using recombinant DNA techniques so that surface proteins on the cell contain histidine tags. A spike of *Salmonella* is added to the sample so that the sample contains 10% *Salmonella* cells, 90% *E. coli* cells, media and other materials.

A 1 mL bed size column containing Ni form IMAC affinity media is used to treat or process a 3-mL sample with unidirectional single pass flow under gravity. Some air pressure is used to push the last remaining solution through the column. The *E. coli* cells are removed from the mixture and are captured on the column while the *Salmonella* cells remain in the sample.

Example 9. Capture of Cells from Culture

Most plant and animal cells can live, multiply, and even express differentiated properties in a tissue-culture dish. The cells can be watched continuously under the microscope or analyzed biochemically, and the effects of adding or removing specific molecules, such as hormones or growth factors can be explored. In addition, by mixing two cell types, the interactions between one cell type and another can be studied. After growing the cells, the specific cells are captured according to processes similar to those described in examples 7 and 8.

After capture, the column is washed and optionally reacted with a dye to label the captured cells. The resin may be removed from the column and plated or spread on a surface. The resin beads containing attached cells may be sorted and counted or analyzed by any means.

Example 10. Companion Diagnostic to Antibody or Fab Based Drug

Often it is unknown whether a particular antibody or Fab drug will be effective against a particular cancer case. The treatment process can be trial and error, trying one drug and then if it is not effective, trying the next drug and so on. Columns of the invention may be used to determine the potential effectiveness of a series of drugs. Tagged drug antibodies and Fabs are prepared. A series of columns of the invention are prepared each with a single antibody bound through the tag to the media of the column. In this way, each available drug is represented by a column. Then a blood sample from a cancer patient is treated by the series of columns in an attempt to capture circulating tumor cells. The columns are washed and the cells, if present, are recovered and analyzed by fluorescence, DNA, microscopy or any suitable analytical technology. Specific drugs that may be effective against the cancer are captured containing drug based affinity media. Then a treatment program is designed using the antibody/Fab drugs that have the highest affinity for the tumor.

Example 11. Nickel-IMAC Column Sterilization 1-ml pipette tip columns containing 80 μL of Ni-IMAC resin were manufactured and 100% glycerol was added to the columns so that the glycerol filled the resin bed up to several millimeters above the bed. The columns were placed in a pipette tip box and the box was autoclaved at 132° C. for 45 minutes.

To verify column sterility, the column resin and a piece of the column body were placed on an LB plate and the plate was incubated at 37° C. After 3 days, no bacterial growth was evident.

The performance of the autoclaved columns was compared with identical columns that had not been autoclaved. His-tagged enhanced green fluorescent protein (eGFP) was purified on the columns using an E4 XLS pipette (Mettler Toledo) as shown in Table 1.

After the sample was loaded onto the columns, two washes were performed. The column was washed with 10 mM $NaH_2PO_4$, 5 mM Imidazole, 0.3 M NaCl, pH 7.4 followed by 10 mM $NaH_2PO_4$, 0.3 M NaCl, 20 mM Imidazole, pH 7.4. Next the eGFP was eluted with 10 mM $NaH_2PO_4$, 0.14M NaCl, 0.25M Imidazole, pH 7.4.

TABLE 1

E4 XLS pipette settings:

| | Volume mL | Cycles | Speed |
|---|---|---|---|
| Equilibration | 0.50 | 1 | Medium |
| Sample | 0.50 | 4 | Medium |
| Wash 1 | 0.50 | 2 | Medium |
| Wash 2 | 0.50 | 2 | Medium |
| Elute | 0.24 | 4 | Medium |

The absorbance of the eluate was read at 488 nm and the yield of purified eGFP was determined. Both the autoclaved column and the column that had not been autoclaved were able to capture eGFP as shown in Table 2 below.

TABLE 2

Columns 1 and 2 were autoclaved and columns 3 and 4 were not autoclaved.

| Column | eGFP excitation peak | Absorbance | Concentration mg/mL | Volume mL | Yield mg |
|---|---|---|---|---|---|
| 1 | 488 | 0.075 | 0.331 | 0.733 | 0.242 |
| 2 | 488 | 0.074 | 0.326 | 0.741 | 0.242 |
| 3 | 488 | 0.081 | 0.357 | 0.753 | 0.269 |
| 4 | 488 | 0.079 | 0.348 | 0.740 | 0.258 |

Example 12. Protein-A Column Sterilization 1-ml pipette tip columns containing 80 μL of ProA resin (PhyNexus, Inc., San Jose, Calif.) were placed in a pipette tip box and the box was autoclaved at 132° C. for 45 minutes. Some of the columns contained glycerol while others did not.

To verify column sterility, the column resin and a piece of the column body were placed on an LB plate and the plate was incubated at 37° C. After 3 days, no bacterial growth was evident.

IgG was loaded on the columns and the columns were operated with an E4 XLS pipette (Rainin) as shown above in Table 1. After the sample was loaded, the columns were washed with phosphate buffered saline (Wash 1) and 140 mM NaCl (Wash 2). The protein was eluted with 200 mM $PO_4$, 140 mM NaCl @ pH 2.5.

The protein yield from the autoclaved columns was compared with the yield obtained from identical columns that had not been autoclaved. The yield of purified IgG obtained the autoclaved proA columns was comparable to those columns that had not been autoclaved.

Example 13. Column Sterilization

Four, 1-ml pipette tip columns containing 80 μL of agarose resin were autoclaved at 132° C. for 45 minutes. Two different agarose resins were used; agarose 1 and agarose 2. Prior to autoclaving, glycerol was added to one column of each resin type. After autoclaving, it was observed that the resin dried out in the columns that did not contain glycerol while the two columns with glycerol added remained wet as shown in Table 3.

TABLE 3

Column sterilization

| Resin | Glycerol | Autoclaved | Dried Out |
|---|---|---|---|
| Agarose1 | No | Yes | Yes |
| Agarose1 | Yes | Yes | No |
| Agarose2 | No | Yes | Yes |
| Agarose2 | Yes | Yes | No |

Example 14. Negative Isolation of Stem Cells

In this example, a sample is enriched for stem cells by removing other cell types. A column is assembled in which the medium is comprised of antibodies that bind undesired cells. The sample is loaded onto the column and the undesired cells are captured on the column. The column flow-through is collected and shown to be enriched for the desired cells.

Example 15. Negative Selection of T Cells from Peripheral Blood Mononuclear Cells T cells are isolated by depletion of all non-T cells such as B cells, macrophages, and natural killer cells. Peripheral blood mononuclear cells (PBMC) are incubated with a mixture of monoclonal antibodies to coat unwanted cells. The suspensions are then loaded onto a column comprised of IgG, which binds the antibody-coated cells. The column flow-through is collected and shown to be enriched for the T cells.

Example 16. Negative Selection of T Cells

The method from Example 15 is applied to different samples such as cells from spleen, lymph node, tumor, and peritoneal fluid.

Example 17. Purification of Sperm Cells by Aptamer Binding

An RNA aptamer having the following sequence is synthesized.

```
Ggcagtccgt ccgtcAZCGA CGCGZGZGZG ZZZGZCZZCZ
ZGZZZGZZGZ CGZGCgccag aagcagaagg acg
```

Z is the modified base, 5-(N-benzylcarboxyamide)-2'-deoxyuridine. A photocleavable linker is conjugated in between the beads and the aptamer to elute the bound cells from the RNA aptamer in one step by UV irradiation The synthesized aptamer is incubated with streptavidin beads in a 1 ml pipette-tip column containing 80 µl of streptavidin resin. A 1 ml sample comprised of sperm cells mixed with other cells is eluted from a swab obtained from sexual assault evidence and diluted in 40 mM Hepes pH 7.5, 350 mM NaCl, 1 mM EDTA, 0.5 mM EGTA, and 0.1% Triton X100 detergent.

The sample is aspirated and expelled from the pipette tip column three times at a rate of 150 µl/min. Non-specifically bound material is removed from the column by washing the column three times with 1 ml of 40 mM Hepes pH 7.5, 350 mM NaCl, 1 mM EDTA, 0.5 mM EGTA, and 0.1% Triton X100. To cleave the aptamer and cells from the resin, the column is subjected to UV irradiation at 1050 mW/cm2 for 5 min. The cells are eluted by aspirating and expelling two times with 500 µl of 40 mM Hepes pH 7.5, 350 mM NaCl, 1 mM EDTA, 0.5 mM EGTA, and 0.1% Triton X100 detergent.

Example 18. Biotinylated Silica Resin

The procedure outlines the creation of antibody conjugated silica beads for capture of *E. coli*. Silica beads were conjugated to biotin. Subsequently, the beads were reacted with aqueous avidin and then *E. coli* antibody tagged with biotin.

Piranha Solution Treatment
Goal: Adding hydroxyl groups to surface of silica.
SIGMA g4649-100G 106 µM silica beads acid washed
95% sulfuric acid stock
30% peroxide stock
Methanol
1. Slowly add 13.1 mL sulfuric acid to 11.9 mL water to make 50% sulfuric acid.
2. Slowly add 25 mL 30% peroxide solution to 50% sulfuric acid solution to make Piranha solution.
3. Add 25 grams of silica beads to solution and mix every 15 minutes for 60 minutes at room temperature.
4. Add silica bead solution to Buchner funnel with #2 filter paper.
5. Wash with dH$_2$O.
6. Wash with methanol.
7. Store powder in beaker at room temperature to dry.

Silanol Conjugation
Goal: Adding amine groups to surface of silica by reacting silanol with hydroxyl groups.
Toluene
APES (3 aminopropyl triethoxy silane)
Alcohol (Anhydrous Reagent 97% Isopropanol)
1. Add glass beads to round bottom flask.
2. Mix 10 mL APES with 90 mL toluene and add it to flask.
3. Rotate intermittently on rotary evaporator for 2 hours at room temperature.
4. Add to Buchner funnel with #2 filter.
5. Wash with alcohol (Anhydrous Reagent 97% Isopropanol).
6. Store powder in beaker at room temperature to dry.

Biotin Conjugation
Goal: Adding biotin to surface of silica by reacting NHS with amine groups.
CAYMAN CHEMICAL COMPANY Item 13315 Biotin NHS (Biotin N-Hydroxysuccinimide Ester)
DMSO
Alcohol (Anhydrous Reagent 97% Isopropanol)
1. Dissolve 500 mg biotin NHS in 100 mL DMSO.
2. Add glass beads to 250 mL round bottom flask.
3. Add 50 mL biotin solution to round bottom flask.
4. Mix by hand every 8 minutes for 2 hours at room temperature.
5. Add to Buchner funnel with #2 filter
6. Wash with alcohol (Anhydrous Reagent 97% Isopropanol).
7. Store powder in 50 mL conical tube in refrigerator.

Example 19. Packing Pipette Tip Columns

Column Packing—Antibody Pipette Tip Columns
1. Add powdered biotin-conjugated resin to tip body.
2. Dispense alcohol (Anhydrous Reagent 97% Isopropanol) into pipette tip column. 3. Store in 50 mL conical tube at room temperature Column Packing—Ion Exchange Tip Columns Strong Base Anion Exchange Resin Tip Columns
1. Suspend strong anion exchange agarose resin in water.
2. Aliquot into reservoir
3. Mix with pipette then pipette 500 µL into Eppendorf tube.
4. Continually add resin to column body and allow to drain until 500 µL has been added
5. Keep in 50 mL tube with dH$_2$O at room temperature

Example 20. Capturing and Eluting E. coli Cells on Pipette Tip Columns

Figure 13:
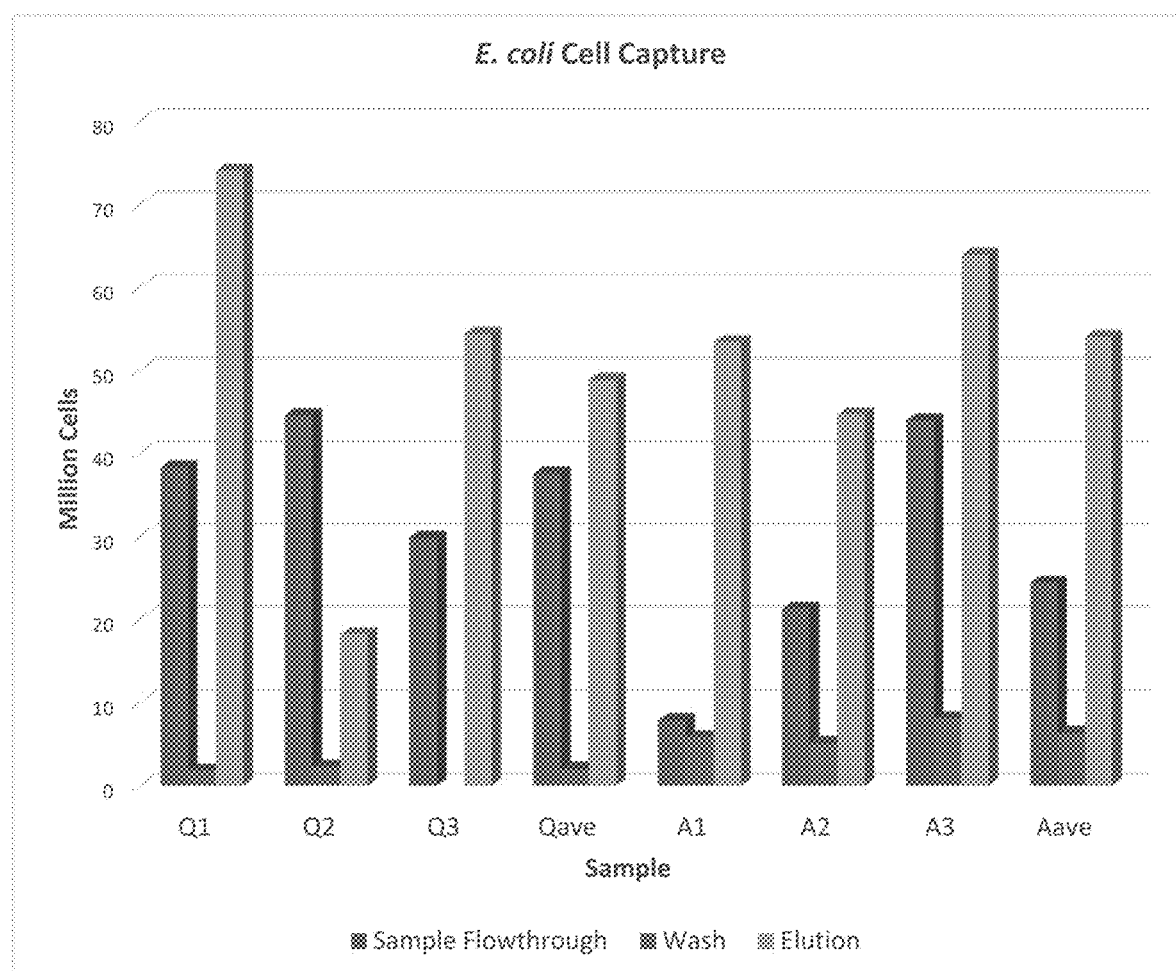
FIG. 13 is a graph showing the number of E. coli cells that are captured on an agarose quaternary ammonium resin (Q) and a silica solid resin (A).

Loading E. coli Cells onto the Column Substrates
Experiment
Using pipette tip columns packed with experimental avidin resin, determine whether DH5á E. coli cells can be captured. Compare purification process with pipette tip columns packed with ion exchange agarose.
Prepare Sample
1) Inoculate 5 mL TB medium with single colony of DH5α.
2) Incubate at 37° C. for approximately 16 hours with shaking at 350 rpm.
3) Measure absorbance at 600 nm until reading reaches 2.4.
4) Aliquot 1 mL culture into 1.5 mL microfuge tubes.
5) Centrifuge at 5,000 rpm for 5 minutes or until medium is clear.
6) Discard medium with a pipette tip.
7) Wash cells—resuspend in 1 mL $H_2O$, centrifuge at 5,000 rpm for 5 minutes, and discard water.
8) Repeat wash two more times for a total of 3 washes.
9) Resuspend cells in 0.5 mL water.
10) Measure absorbance at 600 nm.
11) Make a dilution to a concentration of $1 \times 10^9$ cells/mL or OD 1.4. Label "Concentrated Cells"
12) Sample=100 µL of Concentrated cells+400 µL $H_2O$, or 100 million cells.
Conjugate Avidin to Biotin Pipette Tip Columns
1) Equilibrate pipette tip columns with 500 µL phosphate buffered saline (PBS), 1 cycle, 0.5 mL/min, 20 second pauses.
2) Prepare avidin
   Avidin is supplied as lyophilized 5 mg powder (Prospec, pro-500-a)
   The molecular weight of avidin is 68 kDa, the bottle contains 73.5 nmoles of avidin
   Use a syringe needle to vent the bottle
   Use another syringe and needle to resuspend the powder in 735 µL $H_2O$ to make a 100 µM solution. Make 100 µL aliquots and freeze.
   Make 100 µL of 10 µM avidin: 10 µL 100 µM avidin+90 µL $H_2O$.
   Load 100 picomoles per pipette tip column: 10 µL 10 µM avidin+240 µL $H_2O$
3) Load avidin onto biotin-derivatized pipette tip columns
   Capture with 4 cycles, 0.5 mL/min, 20 second pauses
4) Wash pipette tip columns with 500 µL PBS, 1 cycle, 0.5 mL/min, 20 second pauses.
5) Load biotin-antibody (Pierce, PA1-73035)
   Antibody is supplied as 1 mL solution at 4 mg/mL
   The molecular weight of IgG is 150 kDa
   The solution is 0.0267 µM
   Make 200 µL aliquots and freeze.
   Load 0.5 picomoles of Antibody per pipette tip column: 18.7 µL of 0.0267 µM IgG+231.3 µL $H_2O$
   Capture with 4 cycles, 0.5 mL/min, 20 second pauses
6) Wash pipette tip columns with 500 µL PBS, 1 cycle, 0.5 mL/min, 20 second pauses.
Load Cells
1) Equilibrate pipette tip columns with 500 µL PBS, 1 cycle, 0.5 mL/min, 20 second pauses.
2) Load pipette tip columns with 500 µL Cell Solution, 4 cycles, 0.5 mL/min, 20 second pauses.
3) Wash pipette tip columns with 500 µL PBS, 1 cycle, 0.5 mL/min, 20 second pauses.
4) Elute
   Avidin pipette tip columns: 300 µL Buffer C (200 mM phosphate pH 2.5, 140 mM NaCl), 3 cycles, 0.5 mL/min, 20 second pauses
   Ion exchange pipette tip columns: 300 µL 1M $Na_2SO_4$, 3 cycles, 0.5 mL/min, 20 second pauses
Analyze
1) Visual inspection
   Note sample turbidity after each capture cycle
   Note turbidity of elution
2) Measure absorbance at 600 nm on disposable plastic 1.5 mL cuvettes.
E. coli Column Capture Loading Experiment Results The results indicated that cells can be captured and eluted with pipette tip columns. Six samples were run through the columns using the MEA workstation (PhyNexus, Inc. San Jose, Calif.) as described above. There were three ion exchange columns (Q1-Q3) and three antibody-based columns (A1-A3). Each column was exposed to 100 million cells during the capture cycle and the average number of cells eluted was in the range of 50 million (FIG. 13). The concentration of each individual sample was measured via $OD_{600}$ reading which was then converted to concentration per mL via a ratio calculated from previous experiments. E. coli is captured on a strong anion exchange resin due to surface markers on the cell that contained anion exchange groups.

Six samples were run through the six columns and the number of cells in the sample flow-through, wash, and elution were counted via OD reading for each column. Very few cells were released in the washing stage indicating that both resins were able to retain cells until the elution step.

TABLE 4

The total number of cells counted is in the range of 95 million.

| Sample | Total Million Cells Counted |
|---|---|
| Q1 | 114 |
| Q2 | 65 |
| Q3 | 84 |
| A1 | 67 |
| A2 | 71 |
| A3 | 116 |
| Original | 95 |

The data indicate that the creation of a cell capture pipette tip column was successful. The cell stationary phases are now ready to be used for chromatography.

Example 21. Evaluation of Stem Cell Multi-Potency

One method to evaluate stem cell multi-potency is to measure expression cell surface antigens e.g. CD105, a positive marker for hMSC. These surface antigens can be used to purify multipotent stem cells from a mixture of non-multipotent stem cells and other material. An antibody to CD105 or other specified surface markers can be attached to the affinity resin. The cell culture is passed through the column to capture the multipotent stem cells. Non-specifically bound materials, cells and reagents, are washed from the column. Finally, the purified multipotent stem cells are eluted from the column. The cells are viable and ready for use for therapeutic or research applications.

Example 22. Step Gradient Liquid Chromatography with Pipette Tip Cell Stationary Phase Columns An eight-channel E4 pipette (Mettler Toledo) is fitted to pipette tip column outfitted with adapters that allows them to fit into a 96-well deep well plate. The pipette is programmed with firmware and software to be about to operate with back and forth flow while freestanding in the well. The pipette is moved manually from well to well for the various operations. The 1000 mL pipette tip columns are packed with 100 µL bed volume of PS/DVB resin beads with an average diameter of 50 µm. The beads are surface reacted with streptavidin functional groups.

Cancer cell lines are used as a model for anti-cancer drug testing. A panel of cell lines derived from lung cancer is tested systematically. The panel consists of cells that grow in suspension such as COR-L26. The cells are biotin tagged for immobilization to streptavidin-derivatized beads. Terminal amines of cell surface proteins are labeled, on average of one label per cell, using NHS biotin tags available from Thermo Fisher Pierce (Cat. #20217).

An antibody or biomolecule library is screened for binding to the cell stationary phase columns. The library is injected on the column with bidirectional flow. Step gradient chromatography is used to elute the antibody or biomolecule from the cell stationary phase with increasing stringency steps. The antibody drug leads or biomolecule are selected through their stringency binding properties. Antibodies with the lowest selectivity for the column are eluted first. The strength of the eluent is increased to elute or displace tighter binding antibodies or antibodies or other molecules that have a higher selectivity for the stationary phase. The highest selectivity or the tightest binding antibodies or biomolecule are eluted last. The relative affinity of the molecules is measured and compared.

Pipette tip columns are equilibrated in 1 mL of PBS buffer using two cycles of back and forth flow. A cycle consists of aspiration of the buffer volume minus 50 µL at a flow rate of 250 µL per minute, pause of 20 seconds, dispense of the buffer volume minus 50 µL at a flow rate of 250 µL per minute, pause of 20 seconds, while maintaining the end of the pipette tip column 1 mm above the bottom on the 96-well deep-well plate.

Pipette tip columns are moved to wells containing 1 mL of biotin-labeled COR-L26 cells. The cells are immobilized to the beads using 4 cycles of capture to form the cell stationary phase column. The pipette tip columns are moved to wells containing 1 mL of PBS buffer and the resin is washed using 1 cycle.

The pipette tip columns are next moved to wells containing a 1 mL solution consisting of a commercially available antibody library. The pipette tip columns are loaded with antibody using 4 cycles of capture.

Stringency elution is performed by subjecting the pipette tip columns to a step gradient chromatography, each buffer with a lower pH. The pipette tip columns perform 4 cycles in 300 µL of PBS buffer adjusted to pH 7.2, 7.0, 6.8, 6.6, 6.4, 6.2, 6.0, 5.8, 5.6, 5.4, 5.2, and 5.0 in a step-wise manner. Each condition will be analyzed by mass spectrometry to identify antibodies released under those conditions. The eluted antibodies may be analyzed with MALDI mass spec, or they may be digested with an enzyme and analyzed with LC-MS. In another set of experiments, the elution gradient is a single step gradient after an optional wash step.

In another set of experiments, a living cell stationary phase column is subjected to a potential binding antibody or biomolecule under specified capture conditions or a specified set of capture conditions. The after capture of the antibody or biomolecule, the column is washed and the antibody or biomolecule is eluted and the amount measured. The ability to capture the antibody or biomolecule under different chemical conditions is a measure of the affinity of the antibody or biomolecule for the cell stationary phase.

Example 23. Step Gradient Liquid Chromatography with Flow Through Cell Stationary Phase Columns Experiments described in example 22 are performed with flow through cell stationary phase columns and apparatus as described in the specification.

Example 24. Sealed Chromatographic System

A column was assembled by gluing a frit on one end, packing the column and then gluing the frit on the top of the column. A 37-micron pore, 60-micron thick Nitex screen frits was attached to the end of an acrylic tube 0.750 inches long, 0.500-inch outer diameter and 0.375-inch inner diameter. The tube with frit side down was placed on a deep well plate for packing. Packing was accomplished by standing the column on a stand with hole beneath that allowed the flow of liquid out of the lower end. An aqueous slurry of agarose resin, 45-165-micron particle size, was placed into the column by pipette. The packing material was not compressed. Excess liquid drained away filling the column with resin. Additional slurry was added until the bed of the column reached the top of the column. The end frit of a Nitex screen of the same material was glued onto the column end using a methylene chloride solvent.

Silicone tape was wrapped round the column to increase the diameter. Then two 10-mL plastic syringe bodies and male luer connections were cut to the 1 mL volume mark and placed on the end of the column. The column body was wrapped with stretchable silicone tape to seal the column body.

Male luer connections were connected to the inside of clear flexible Tygon tubing 0.25-inch outer diameter with pinch valve. The tubing was connected to 1000 mL Kendall (cat. no. 763656) adapted to be flexible closed feed/receiving container. 250 mL of DI water was added to one of the containers and sealed. At this point, no air remained in the system and the entire column and receiver/feed system was closed to the outside.

The feed container was filled with 250 mL of DI water with the tube pinch valve pinched closed and placed on a stand. The receiving container was placed on stand 10 inches below the feed bad. The pinch valve was opened and the fluid flowed from the feed container through the feed container into the receiving container in a closed system. Flow was controlled by the relative difference in height of the two bags or containers. Flow as low as 10 µL/min was all employed to as high as 20 mL/min for this particular column. Higher flow rates are possible with greater height differences, lower backpressure columns or the use of peristaltic or bag (or container) compression pumping.

After the flow through the column was completed, the relative position of the feed container and receiving container was reversed by simply lowering the feed container (now the receiving container) and raising the receiving container (now the feed container), reversing the flow through the column. This can process can be performed as often as necessary to provide complete capture of the cell or other process.

In another set of experiments, the flow through the column is performed with a peristaltic pump or other type of pumping device. In this apparatus, the relative positions of feed and receive reservoirs is not important.

Example 25. The Use of Ion Exchange Pipette Columns to Capture and Elute E. coli and S. aureus A strong anion exchange resin was chosen as the column matrix to provide a positively charged surface to which the negatively-charged bacterial cell capsule and lipopolysaccharides could bind. After binding the cells to the column, they were eluted and their viability was assessed by plating dilutions onto solid media. Elution was carried out using NaCl. The chloride anions successfully displaced the bacteria off the column, without compromising cell viability.

Procedure

1. The pipette tip column containing 100 μL of an agarose-based strong anion exchanger was placed onto a computer-controlled E4 XLS (Mettler Toledo) automatic pipette.
2. The column was equilibrated by aspirating 500 μL of 10 mM phosphate buffered saline solution (PBS), pH 7.4, at a rate of 0.75 mL/min from a 96 well plate or Eppendorf tube. After 10 seconds, 400 μL of the PBS solution was expelled from the column.
3. Two bacterial suspensions were grown in LB, one with 100,000 and second a with 600,000 cells/mL. Two different bacterial strains were used. The first strain was E. coli BL21 harbouring an ampicillin resistant plasmid and LB supplemented with ampicillin was used for growth. The second strain was Staphylococcus aureus SH1000.
4. 500 μL of the bacterial suspension (either 50,000 or 300,000 cells) was taken up at a rate of 0.75 mL/min. After 10 seconds, 500 μL were expelled at the same rate.
5. To remove non-specifically bound bacterial cells from the column matrix (or other areas of the column such as the exterior of the tip), the column was washed with 25 consecutive fractions of LB. 500 μL of LB was aspirated from and immediately expelled back into an Eppendorf tube containing a total volume of 1 mL LB, ensuring the outside of the column tip is fully submerged in order to wash bacteria from the outside of the column, as well as washing them from the inside. These fractions were collected and frozen in glycerol for subsequent analysis. Four replicates of the 25$^{th}$ fraction were plated on LB agar, incubated for 16 hours at 37° C. and the resulting colonies were counted.
6. After 25 consecutive LB washes, bacteria bound the column were eluted by washing the column with LB containing increasing concentrations of NaCl from 50 mM to 1M. 500 μL of LB broth, containing the appropriate concentration of NaCl, was aspirated at a rate of 0.75 ml/min and then immediately expelled.
7. Eluted bacterial fractions were plated on LB agar and incubated for 16 hours at 37° C. before being counted. For each eluted bacterial fraction, four replicates were plated.

TABLE 5

E. coli—300,000 cells.

| [NaCl] (mM) | Colonies | | | |
|---|---|---|---|---|
| | Replicate 1 | R2 | R3 | R4 |
| 25$^{th}$ Wash Fraction (0 mM) | 984 | 804 | 863 | 973 |
| 50 | 3704 | 1984 | 2345 | 2764 |
| 100 | 4128 | 3682 | 4032 | 4256 |
| 150 | 5728 | 4893 | 5409 | 5610 |
| 200 | 5936 | 4690 | 5537 | 6109 |
| 300 | 4902 | 5783 | 4723 | 5267 |
| 400 | 1928 | 1423 | 1746 | 2105 |
| 500 | 1112 | 812 | 1092 | 1273 |
| 750 | 416 | 444 | 321 | 492 |
| 1000 | 146 | 128 | 113 | 182 |
| TOTAL | 28000 | 23839 | 25318 | 28058 |
| Approx. % Cells bound | 9.33% | 7.95% | 8.44% | 9.35% |

TABLE 6

E. coli—50,000 cells

| [NaCl] (mM) | Colonies | | | |
|---|---|---|---|---|
| | Replicate 1 | R2 | R3 | R4 |
| 25$^{th}$ Wash Fraction (0 mM) | 213 | 173 | 167 | 193 |
| 50 | 693 | 478 | 435 | 528 |
| 100 | 1363 | 1223 | 1290 | 1309 |
| 150 | 1765 | 1545 | 1368 | 1573 |
| 200 | 1492 | 1145 | 1092 | 1390 |
| 300 | 579 | 431 | 675 | 545 |
| 400 | 331 | 359 | 202 | 298 |
| 500 | 132 | 123 | 98 | 105 |
| 750 | 108 | 93 | 65 | 43 |
| 1000 | 27 | 83 | 40 | 7 |
| TOTAL | 6190 | 5478 | 5265 | 5798 |
| Approx. % Cells bound | 12.38% | 10.96% | 10.53% | 11.59% |

TABLE 7

S. Aureus—300,000 cells

| [NaCl] (mM) | Colonies | | | |
|---|---|---|---|---|
| | Replicate 1 | R2 | R3 | R4 |
| 25$^{th}$ Wash Fraction (0 mM) | 444 | 509 | 549 | 465 |
| 50 | 2965 | 2305 | 2789 | 2340 |
| 100 | 3520 | 3109 | 3356 | 3271 |
| 150 | 4509 | 3756 | 4137 | 3987 |
| 200 | 3229 | 3912 | 3547 | 3730 |
| 300 | 1732 | 1907 | 1809 | 1869 |
| 400 | 902 | 933 | 810 | 758 |
| 500 | 630 | 739 | 548 | 586 |
| 750 | 214 | 312 | 253 | 201 |
| 1000 | 89 | 119 | 133 | 79 |
| TOTAL | 17790 | 17092 | 17382 | 16821 |
| Approx. % Cells bound | 5.93% | 5.70% | 5.79% | 5.61% |

TABLE 8

S. Aureus—50,000 cells

| [NaCl] (mM) | Colonies | | | |
|---|---|---|---|---|
| | Replicate 1 | R2 | R3 | R4 |
| 25th Wash Fraction (0 mM) | 145 | 136 | 146 | 123 |
| 50 | 489 | 462 | 507 | 424 |
| 100 | 798 | 875 | 806 | 693 |
| 150 | 1232 | 1156 | 1178 | 1098 |
| 200 | 920 | 815 | 904 | 722 |
| 300 | 789 | 642 | 736 | 634 |
| 400 | 334 | 309 | 312 | 298 |
| 500 | 145 | 136 | 176 | 117 |
| 750 | 98 | 78 | 102 | 86 |
| 1000 | 46 | 67 | 56 | 60 |
| TOTAL | 4851 | 4540 | 4777 | 4132 |
| Approx. % Cells bound | 9.70% | 9.08% | 9.56% | 8.23% |

Example 26. Impact of the Ion Exchange Pipette Tip Column on Cell Viability

In order to determine the suitability of the column for capturing and then eluting bacteria, the impact of the loading and release process on the cells was investigated. The cells must be able to undergo the process of passing through the frit and being captured and released from the resin in high salt conditions without any significant impact on the overall viability of the bacterial population.

To you tomorrow determine the impact on viability, 0.5 ml of a dilute suspension of *E. coli* was plated onto LB agar and incubated. 0.5 ml of the same suspension was aspirated and immediately expelled from the column 25 times. The bacteria bound to the column were then eluted by washing the column with the bacterial suspension, now containing 100 mM NaCl, over 10 consecutive cycles to comprehensively remove effectively all bacteria. The resulting bacterial suspension was then plated and allowed to incubate in the same conditions as the *E. coli* suspension that had not passed through the column. A flow rate of 0.75 ml/min was used for all aspirations and expulsions.

TABLE 9

The effect of the column process on viability

| | Number of colonies | |
|---|---|---|
| | Replicate 1 | Replicate 2 |
| Sample without washing through column | 1304 | 1258 |
| Sample washed through column | 1239 | 1185 |
| % Viable after washing | 95.02% | 94.20% |

These results show that the overall process of capture, washing and elution using the ion exchange resin has very little effect on the viability of *E. coli* cells. The difference in colony number between the washed and unwashed samples may be due to some cells still being retained on the column. These data show that when the column is operated at 0.75 ml/min the method is highly suitable for eluting and subsequently growing viable bacterial cells.

Example 27. On-Column Selection of Bacterial Species Based on Antibiotic Resistance A mixed population of two bacterial species were separated in a pipette tip column based on their resistance to ampicillin. A mixed population of *Staph aureus* SH1000 and *E. coli* BL21 were loaded onto the column. *E. coli* BL21 contains a plasmid which confers ampicillin resistance while *S. aureus* SH1000 is ampicillin-sensitive. The cells were exposed to ampicillin on the column and then eluted and plated.

A mixed suspension of the two bacterial strains was prepared that contained approximately 25,000 cells of each species per mL. 0.5 mL of the suspension was aspirated through the open lower end of the column and 25 wash steps were performed with LB to remove unbound bacterial cells. 0.5 mL of LB broth containing 100 μg/mL ampicillin was then aspirated into the column, and allowed to remain in the column for 10 seconds before expulsion. Cells were eluted from the column using 0.5 mL LB broth containing 200 mM NaCl and the resulting eluent plated on LB agar.

After incubation for 16 hours for 37 C the number of cells of each species was counted.

SH1000 and BL21 cells can be distinctly recognized on a plate due to the difference in the color of their colonies. SH1000 colonies are a dark yellow/orange color on an LB agar plate and appear more opaque than the *E. coli* colonies.

As expected, a much larger number of *E. coli* cells were viable after elution of the cells from the column. Only a small number of *S. aureus* cells were present.

TABLE 10

Number of colonies of each species after washing with LB broth containing ampicillin

| | Number of colonies | | |
|---|---|---|---|
| Bacterial Species | Replicate 1 | Replicate 2 | Replicate 3 |
| *E. coli* BL21 | 824 | 922 | 809 |
| *S. aureus* SH1000 | 12 | 21 | 15 |

Example 28. Measurement of Cell Viability

Cell viability may be measured using a dye exclusion process. A blue solution is prepared in PBS (4 mg/mL). Approximately 0.9 mL of diluted cell suspension is mixed with 0.1 mL trypan blue pH 7. After 5 min at room temperature, the viable (unstained) and nonviable (stained) cells are counted in a hemocytometer or microscope.

I claim:

1. A method for making and using an adhesion column, comprised of:
    (a) growing cells in a suspension of beads or particles, wherein the suspension is comprised of a growth medium, and wherein the cells attach to the beads or particles to produce adherent cells;
    (b) providing a column;
    (c) introducing the adherent cells into the column to produce an adhesion column;
    (d) providing at least one analyte;
    (e) passing the analyte through the adhesion column, wherein the analyte interacts with or binds to the adherent cells in the adhesion column.

2. The method of claim 1, wherein the analyte is passed through the adhesion column in a mobile phase.

3. The method of claim 1, wherein following step (e), an eluent is passed through the adhesion column.

4. The method of claim 3, wherein the eluent is directed to a detector.

5. The method of claim 1, wherein the cells are recovered and analyzed.

6. The method of claim 1, wherein the cells are lysed following step (c) or step (e).

7. The method of claim 6, wherein components of the lysed cells are recovered and analyzed.

8. The method of claim 1, wherein the column is a pipette tip, syringe or cartridge.

9. The method of claim 2, wherein the mobile phase is passed through column using back and forth flow.

10. The method of claim 3, wherein the eluent is passed through the column using back and forth flow.

11. The method of claim 2, wherein the mobile phase is passed through column using unidirectional flow.

12. The method of claim 1, wherein the eluent is passed through the column using unidirectional flow.

13. The method of claim 1, wherein the method is automated.

14. The method of claim 1, wherein the method is performed with a plurality of columns operated in parallel.

15. The method of claim 1, wherein the cells are stem cells, mammalian cells, human cells, cancer cells, natural killer (NK) cells, monocytes, macrophages, endothelial cells, smooth muscle cells, dendritic cells, mast cells, fibroblasts or epithelial cells.

16. The method of claim 1, wherein following step (c), a library of compounds is passed through the column.

17. The method of claim 1, wherein the analyte is a drug or drug candidate.

18. The method of claim 1, wherein the sample or analyte is a tag.

\* \* \* \* \*